United States Patent [19]

Sandland et al.

[11] Patent Number: 4,644,172

[45] Date of Patent: Feb. 17, 1987

[54] ELECTRONIC CONTROL OF AN AUTOMATIC WAFER INSPECTION SYSTEM

[75] Inventors: Paul Sandland, Gilroy; Kenneth Levy, Saratoga; Russell M. Singleton, Sunnyvale; Michael L. Hodgson, San Jose; Gerald R. Cutler, Santa Clara, all of Calif.

[73] Assignee: KLA Instruments Corporation, Santa Clara, Calif.

[21] Appl. No.: 582,583

[22] Filed: Feb. 22, 1984

[51] Int. Cl.$^4$ .................. G01N 21/86; G01V 9/04
[52] U.S. Cl. .................... 250/548; 356/400
[58] Field of Search .......... 250/548, 557, 561; 356/400, 401; 358/106; 364/507

[56] References Cited

U.S. PATENT DOCUMENTS

| | | | |
|---|---|---|---|
| 3,890,508 | 6/1975 | Sharp | 250/548 |
| 4,255,056 | 3/1981 | Peterson | 356/401 |
| 4,531,060 | 7/1985 | Suwa et al. | 250/548 |

*Primary Examiner*—David C. Nelms
*Assistant Examiner*—William Oen
*Attorney, Agent, or Firm*—Hamrick, Hoffman Guillot & Kazubowski

[57] ABSTRACT

A system for automatic micro and macro inspection of patterned wafers, including a X-Y stage for supporting and positioning a wafer at a macro inspection station and a micro inspection station, a plurality of cassettes for storing a plurality of patterned wafers before and after inspection, a transfer arm and apparatus for transferring a wafer from the cassettes to a predetermined location on the X-Y stage, apparatus for centering the wafer on the macro inspection station, apparatus for aligning the wafer to obtain a preselected orientation for macro inspection, an optical system for effecting macro inspection of the wafer and storing a unique image thereof, apparatus for moving the wafer from the macro inspection station to the micro inspection station so that the area of the wafer corresponding to the stored unique image is in a micro optical path, autofocus apparatus for automatically focusing the lowest magnification objective lens on the area of the wafer to derive a real time image, a comparitor for comparing the stored unique image to the real time image, apparatus responsive to the comparison of the stored unique image and the real time image and operative to more precisely position the wafer in the micro optical path, apparatus for using areas of the wafer displaced one from the other to obtain more precise alignment of the wafer, apparatus for performing a pre-established micro inspection of selected areas of the wafer and apparatus for returning the wafer to a storage cassette.

8 Claims, 54 Drawing Figures

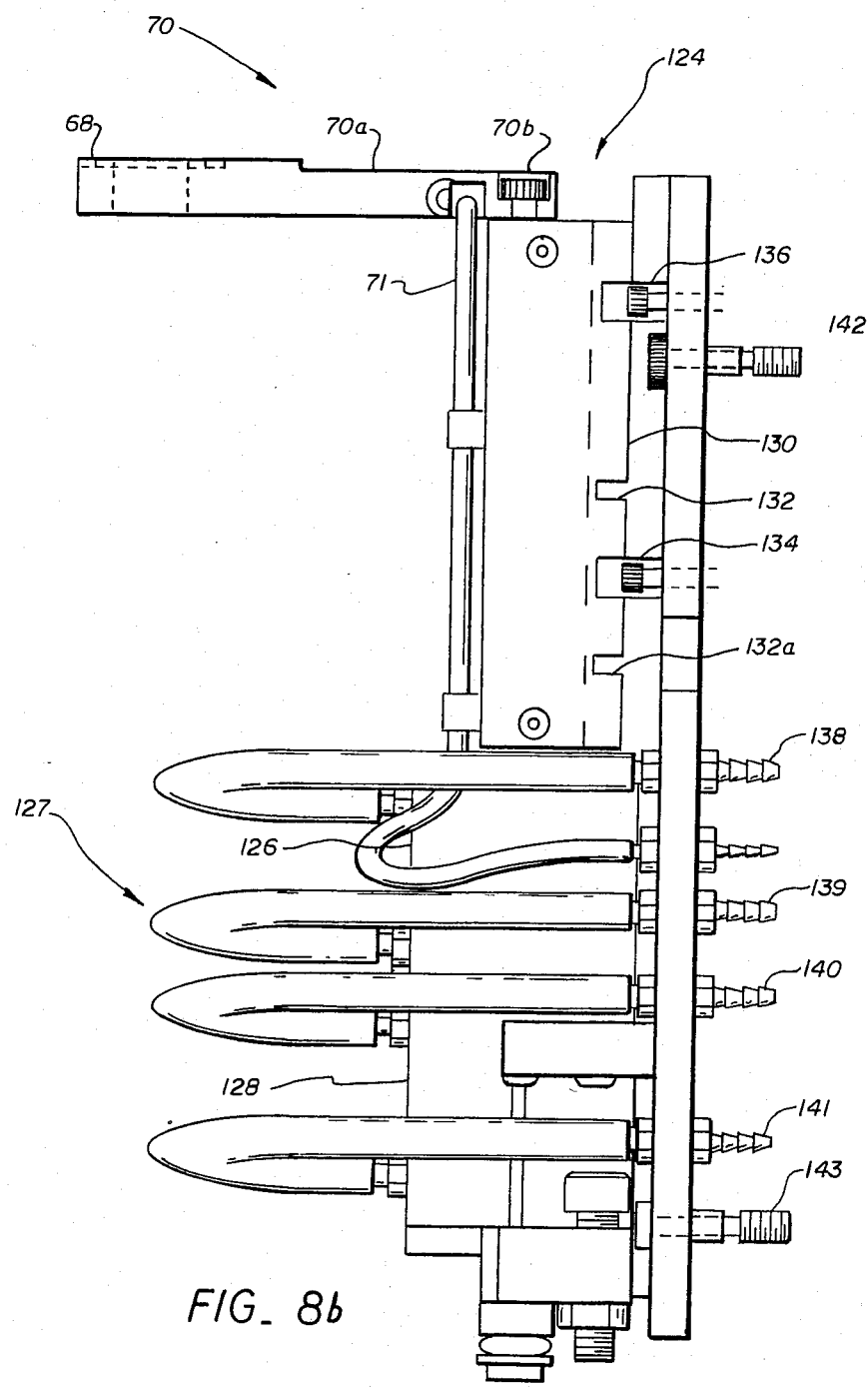
FIG_ 8b

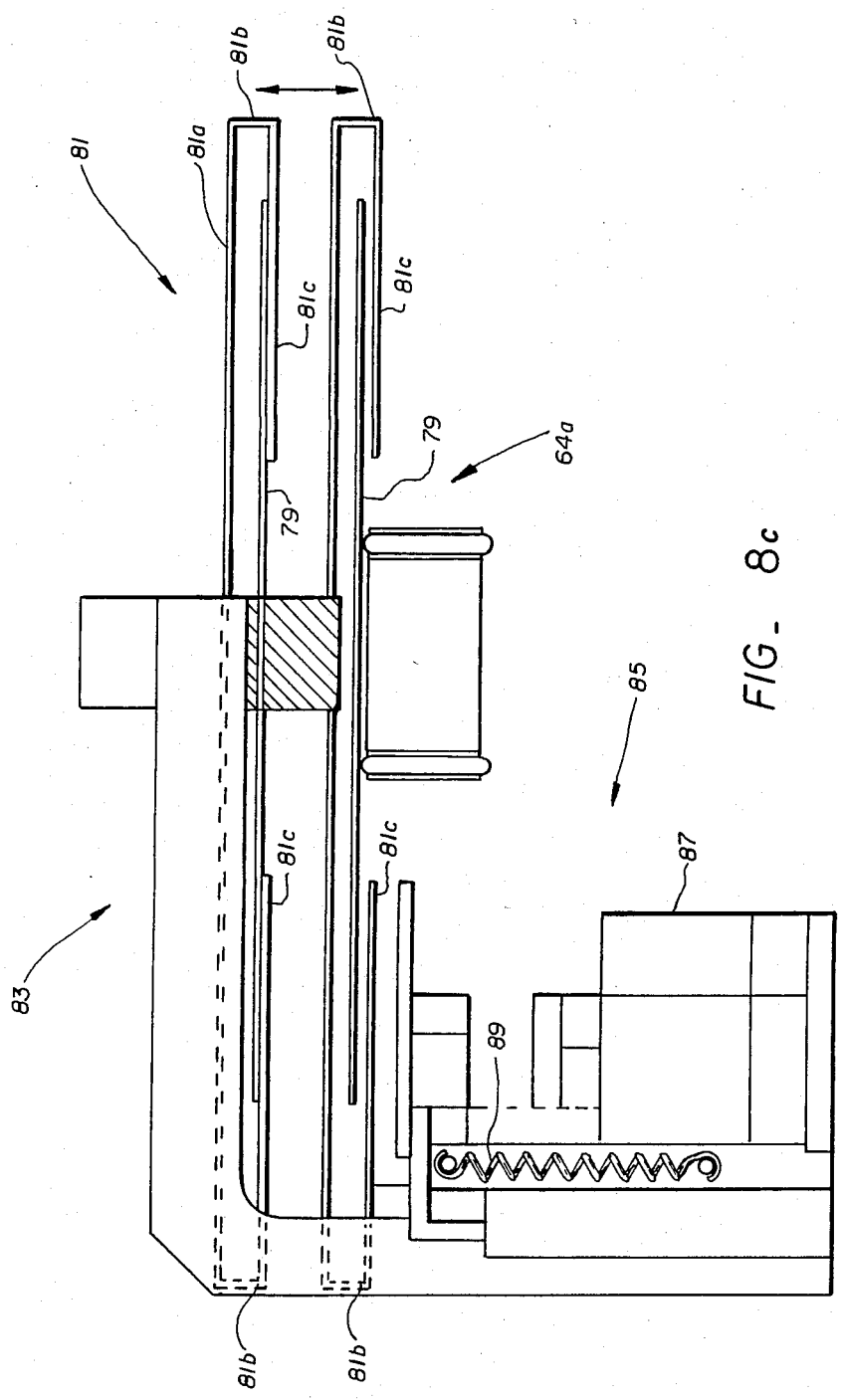

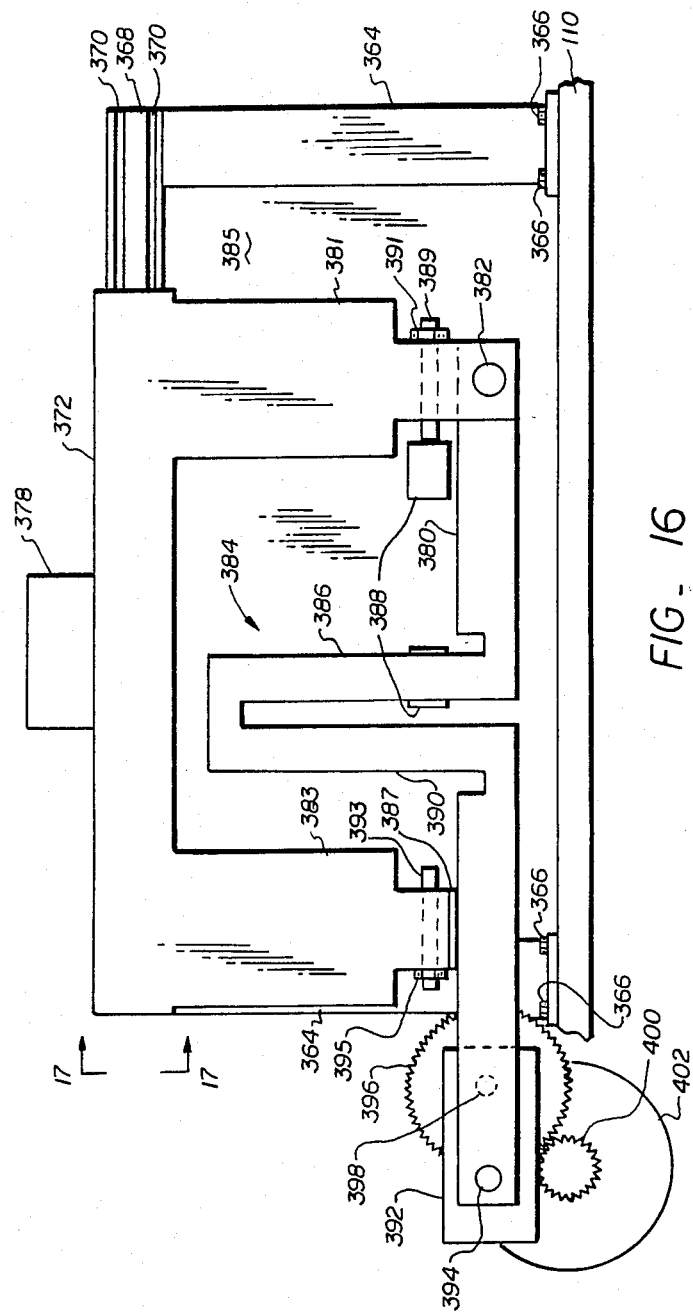

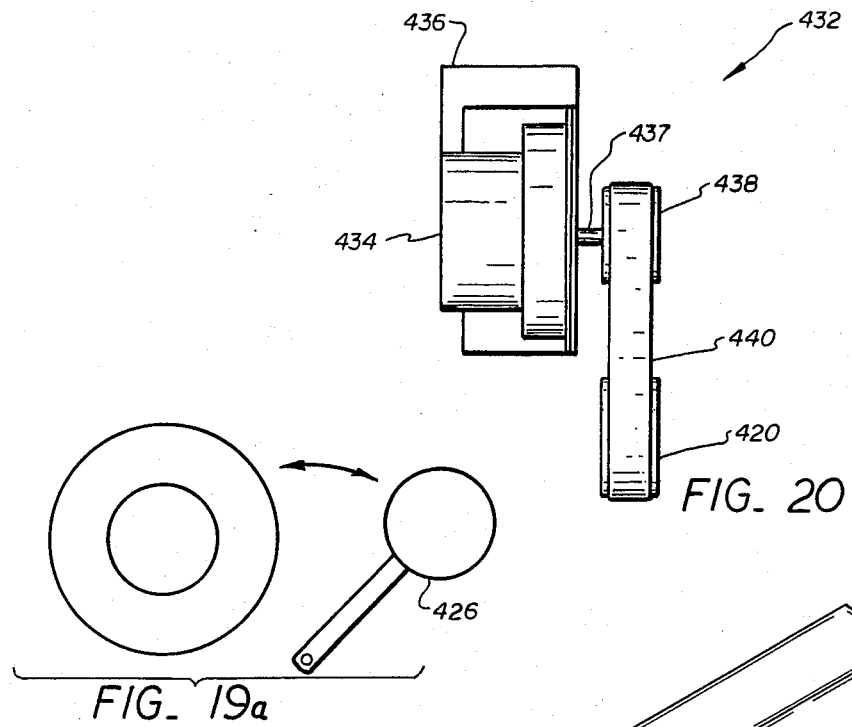
FIG. 20
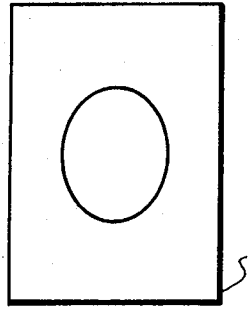
FIG. 19a
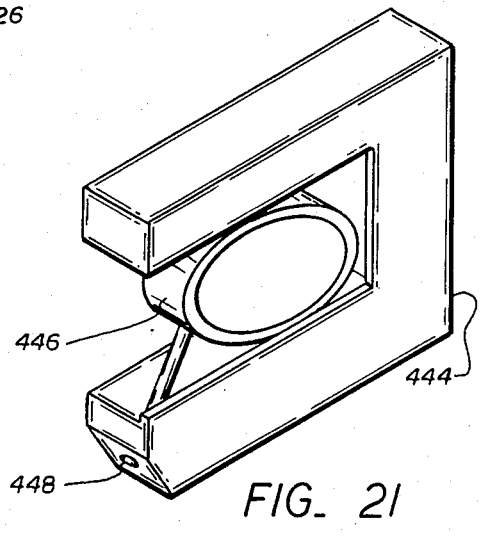
FIG. 19b
FIG. 21

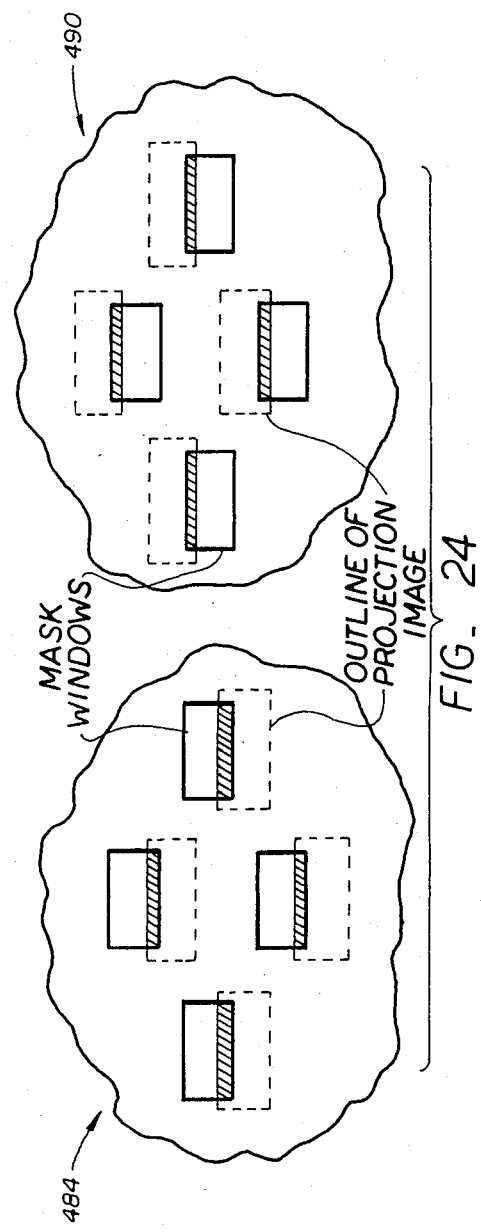
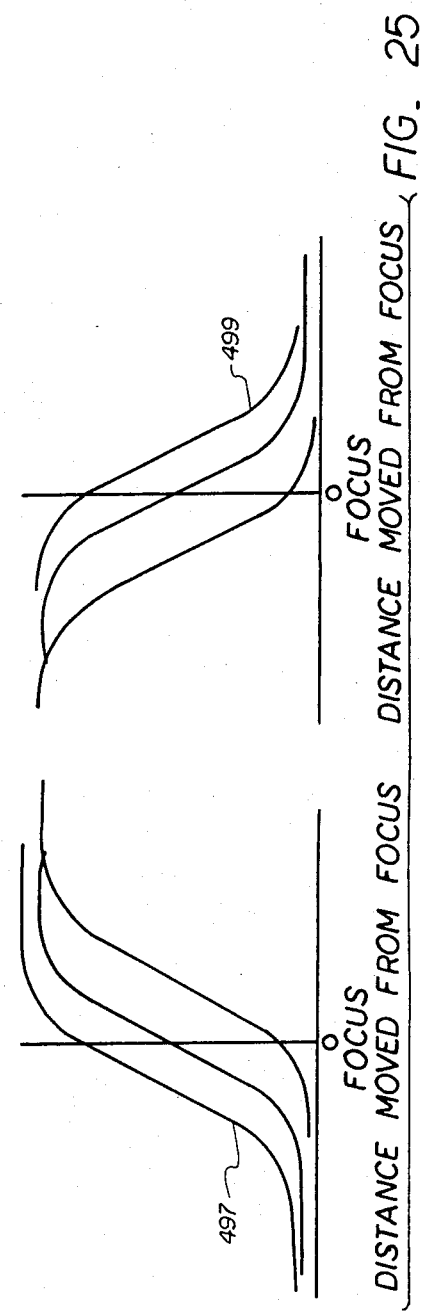

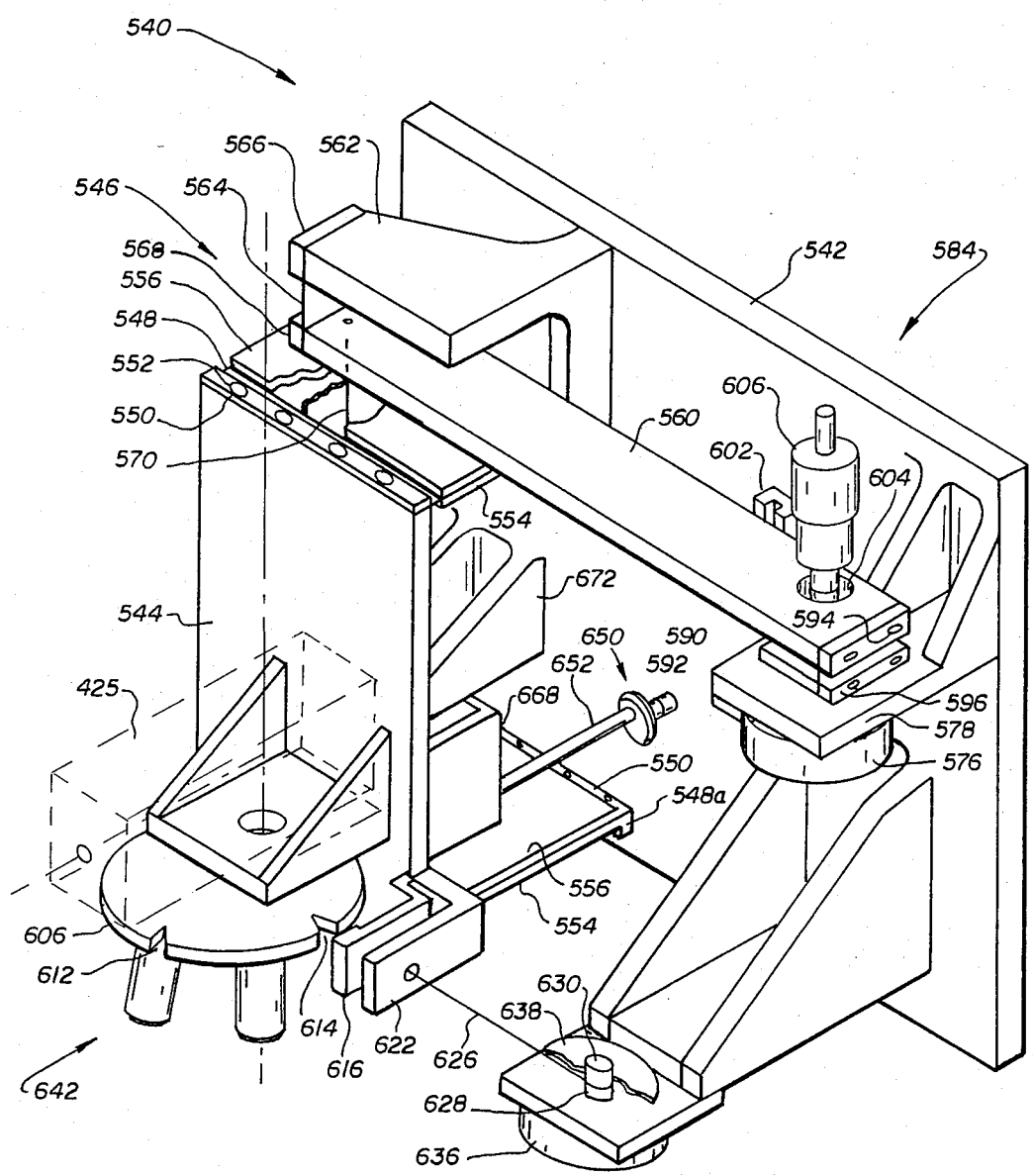
FIG_ 30

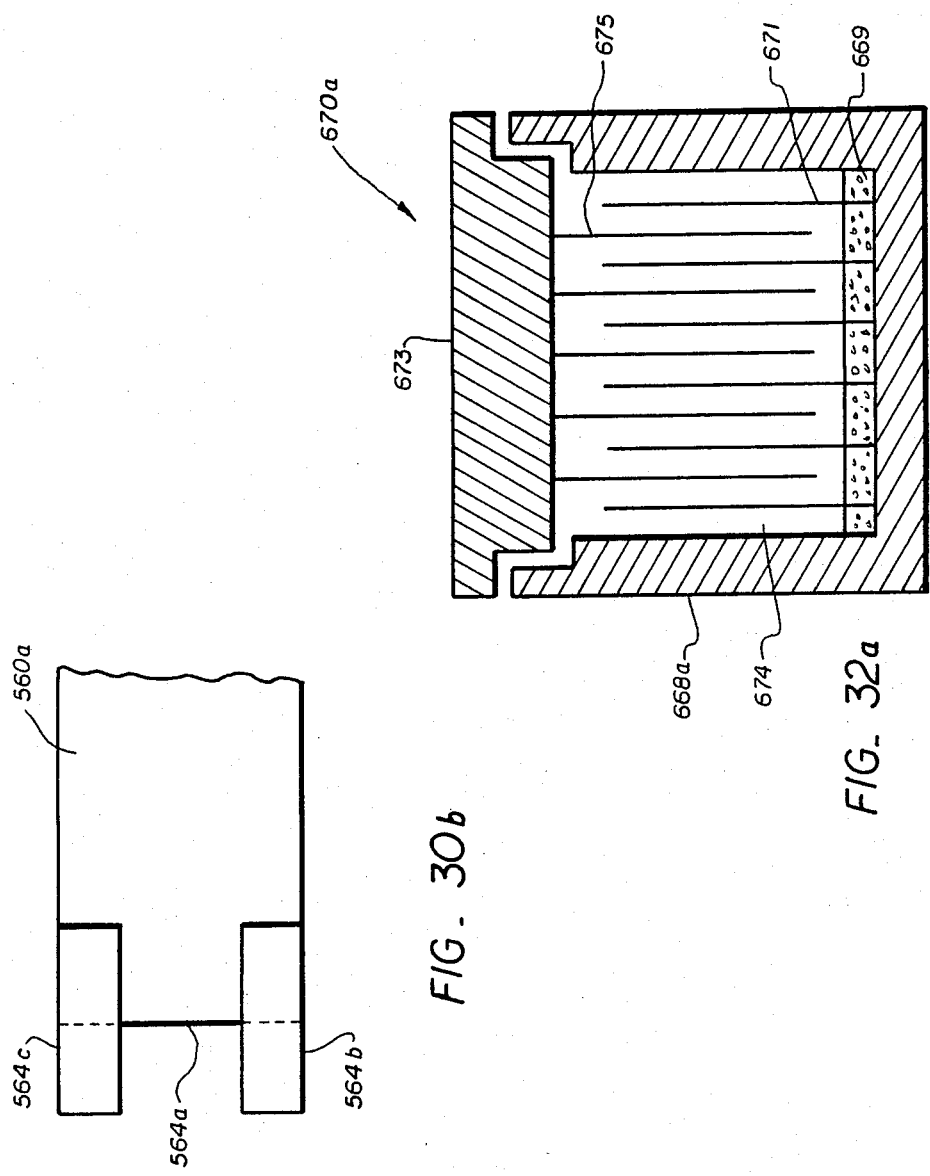

FIG_41

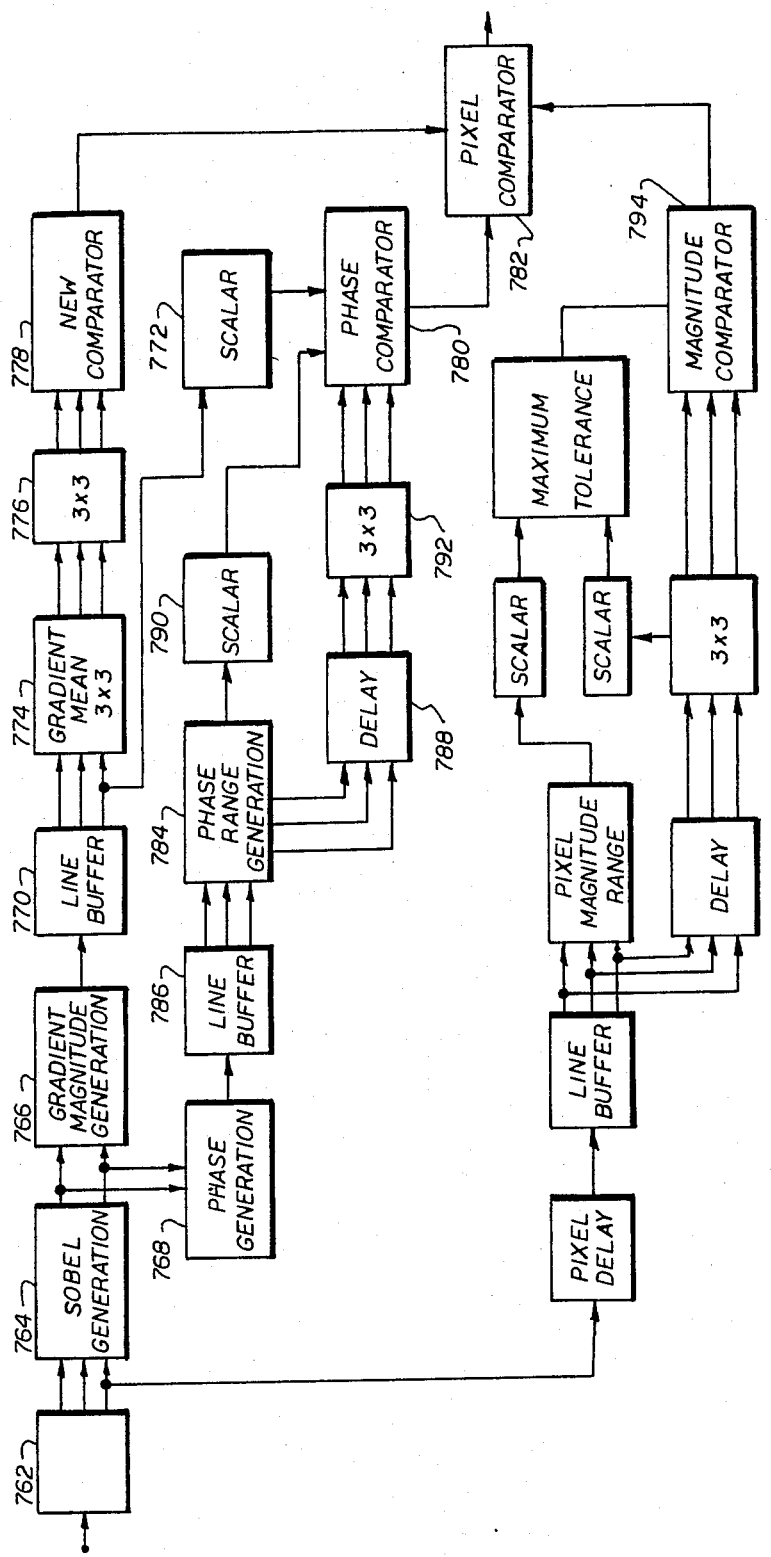
FIG_ 44

ELECTRONIC CONTROL OF AN AUTOMATIC WAFER INSPECTION SYSTEM

BACKGROUND OF THE INVENTION

1. Field of the Invention

This invention relates to the macro and micro inspection of simi conductor wafer for defects, and/or particularly to an electronic control arrangement for automatically performing the inspection process.

2. Description of the Prior Art

Although the inspection of unpatterned wafers for cleanliness has alone been automated, patterned wafers continue to be inspected manually. In this case, a patterned wafer is placed on a wafer chuck under a bright light and is positioned to avoid reflections so as not to blind the viewer. At the same time, the position of the light with respect to the angle of the wafer must be such as to pick up scattered light from particulate contamination. Also, large defects may be detected. The full wafer is inspected and some of the characteristics of the present day manual macro inspection are: a quick check of large defects specifically particulate contamination down to approximately ten microns; checks for non-uniformities of exposure or development, and checks for poor spin; either backsplash, starburst, penumbral effect, contamination, etc.

Typically, micro inspections today are done by an inspection operator using a standard microscope. The areas of inspection include (1) registration checking, (2) pattern check for systematic defects, and (3) point defect checking. The latter can be typified in one of two ways: either (3a) random defects, or (3b) repeating defects. Random defects are common to all photo processes. The resulting defect density is recognized as a major yield limiter and as such must be monitored to provide data for yield control. Typical sources of random defects are random mass defects, defects in films (including resist), air-born and liquid born particulate contamination. Repeating defects from a mask or reticle are a major cause of yield loss; in particular when using stepping lithography, the repeating defect prints everytime the reticle field is printed.

Although manual inspection is rather simple, and requires relatively low cost equipment, the results are somewhat inconsistent because of the subjective nature of the assessment and the attention span of the operator. Further, the time required to process the wafer as well as the limited amount of information that may be readily obtained limits the application of the manual inspection techniques to statistical sampling.

SUMMARY OF THE PRESENT INVENTION

It is an object of the invention to provide an electronic control system which sequentially effectuates the control devices used to automatically perform macro and micro inspection of a patterned wafer.

It is also an object of the invention to provide for selection of those wafers which are to undergo macro and micro test.

It is another object of the invention to provide for the selection of tests to be performed on a particular class of wafer, and for establishing the test criteria for each test during an inspection.

It is still another object of this invention to separately store images developed for a class of wafer so that an image may be used for comparison with a corresponding image of the wafer under test.

It is a further object of the invention to provide for interruption of the inspection for a single wafer whenever the processing of the test results indicated that the wafer defects exceed those considered acceptable.

It is yet a further object of the invention to interrupt the testing of a batch of wafers whenever the failure rate exceeds a pre-established limit.

It is still a further object of the invention to direct the inspected wafer to a pass or fail cassette as appropriate following the inspection.

Briefly, the invention relates to a control system for use with an automatic wafer inspector that is based on a micro processor which provides default criteria for comprehensive macro and micro tests performed during an inspection, and which permits the user to select pass or fail tolerances, the test to be performed and the selection of wafers to be tested for each class of wafers undergoing inspection.

IN THE DRAWING

FIG. 8B is a view along line 8B—8B of FIG. 8A;

FIG. 8C is an elevation view of the garage (81) and associated components used with alignment wafer (79);

FIG. 16 is an elevation view illustrating the drive mechanism for the macro lenses, moveable mirror and pentaprism;

FIG. 19A illustrates darkfield control element (426);

FIG. 19B shows the partialy silvered mirror (428);

FIG. 20 illustrates how stepper motor (434) and pulley (438) drives aperture and pupil stop (420) by belt (440);

FIG. 21 is an isometric view of a lens bracket used in the micro illuminator (408);

Figure 23:
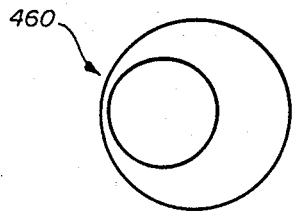
Figure 26:
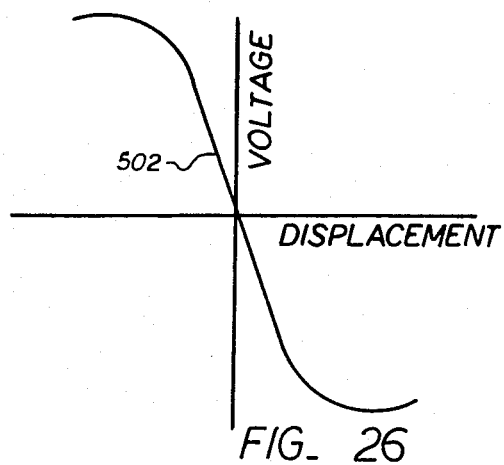
Figure 27:
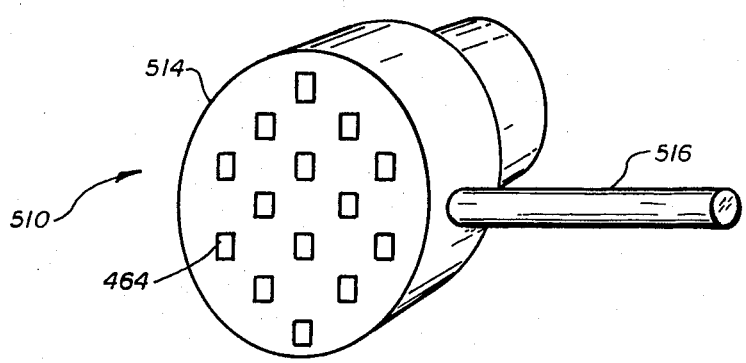
Figure 28:
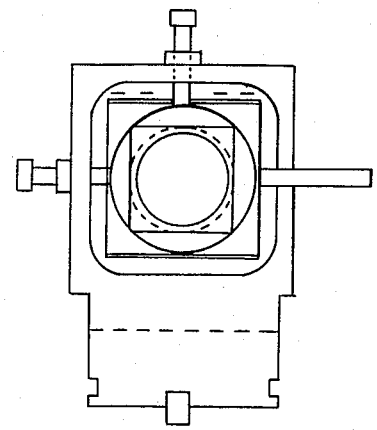
Figure 29:
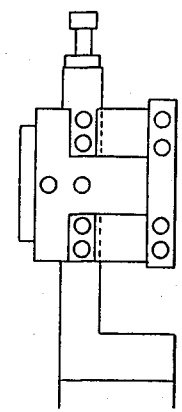
Figure 30A:
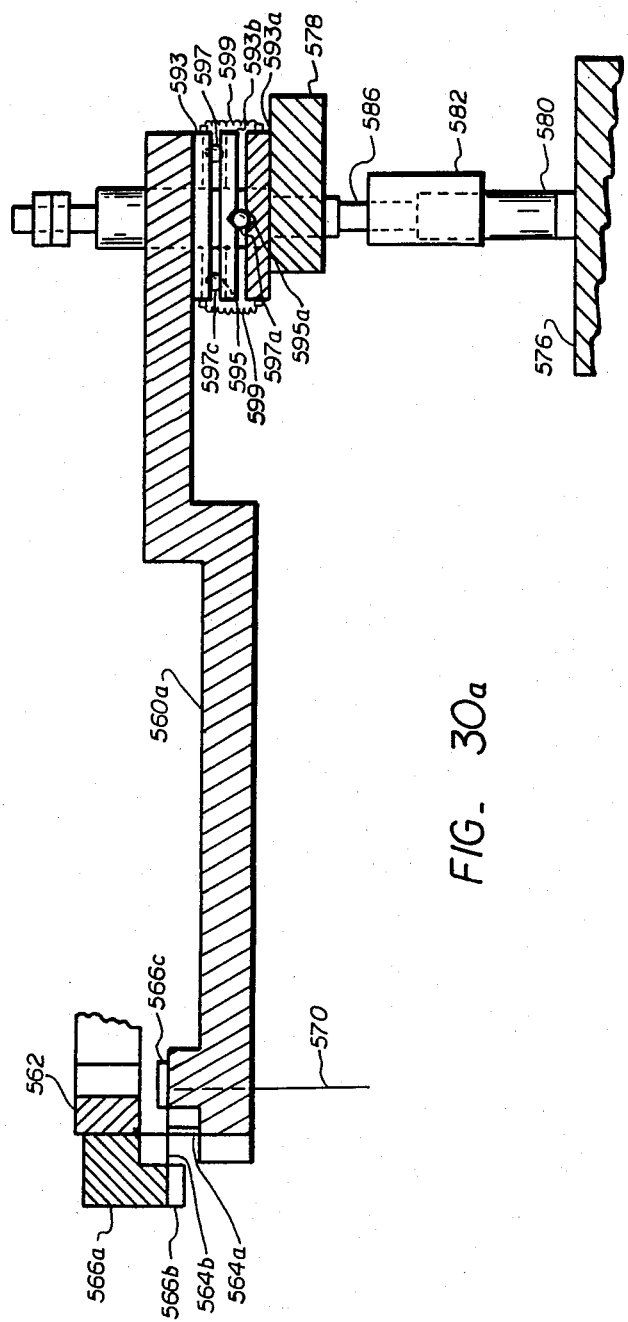
Figure 31:
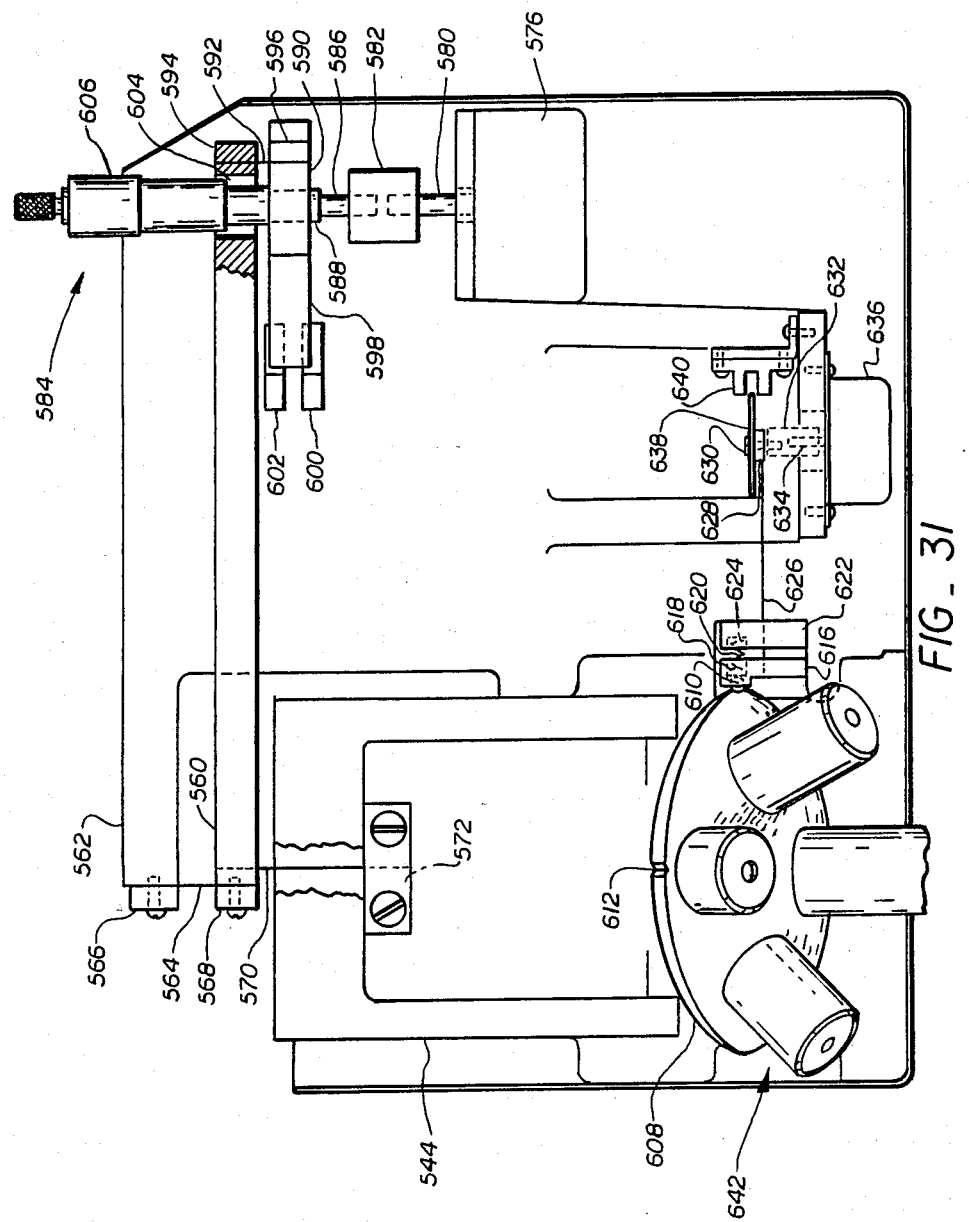
Figure 32:
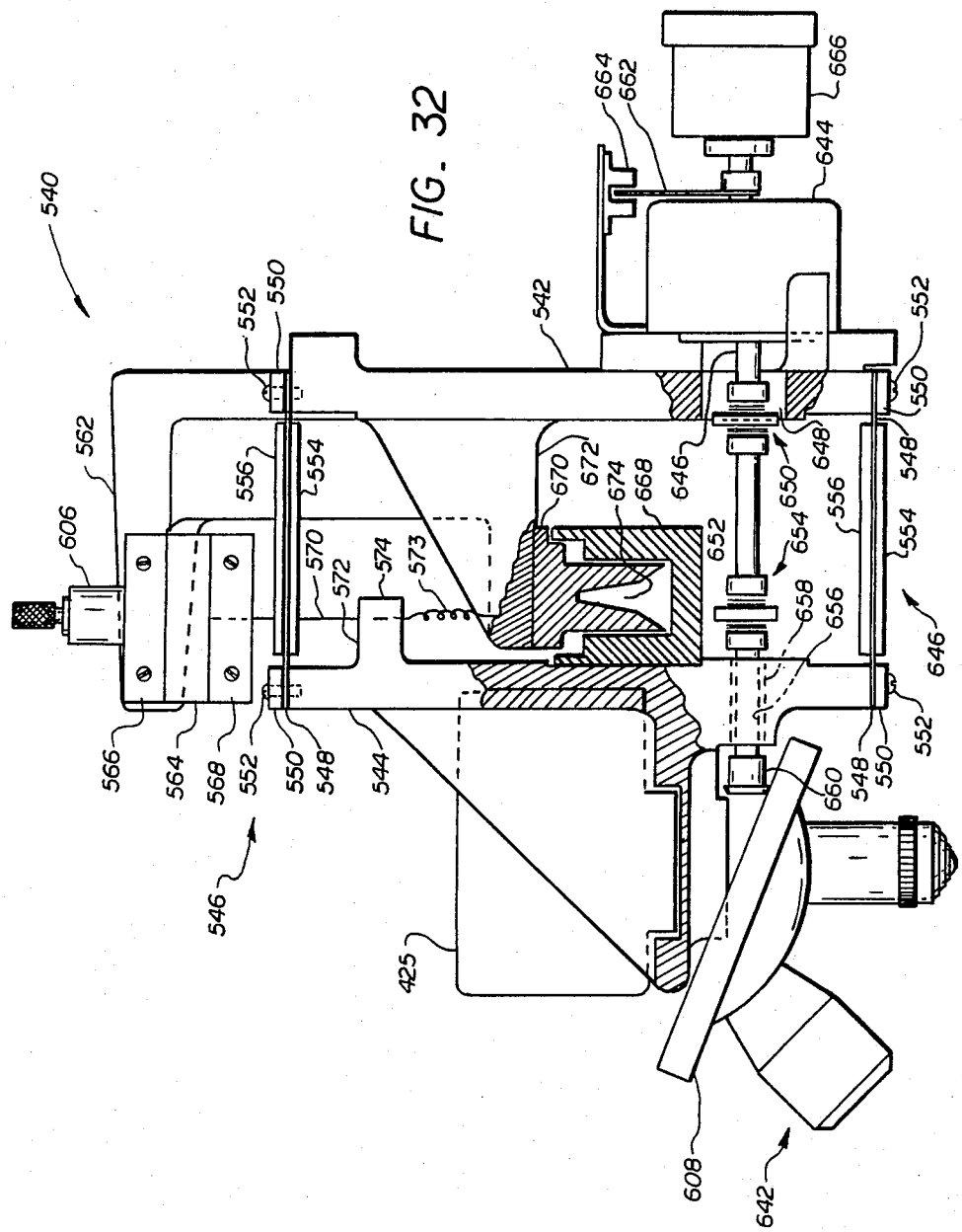
Figure 33:
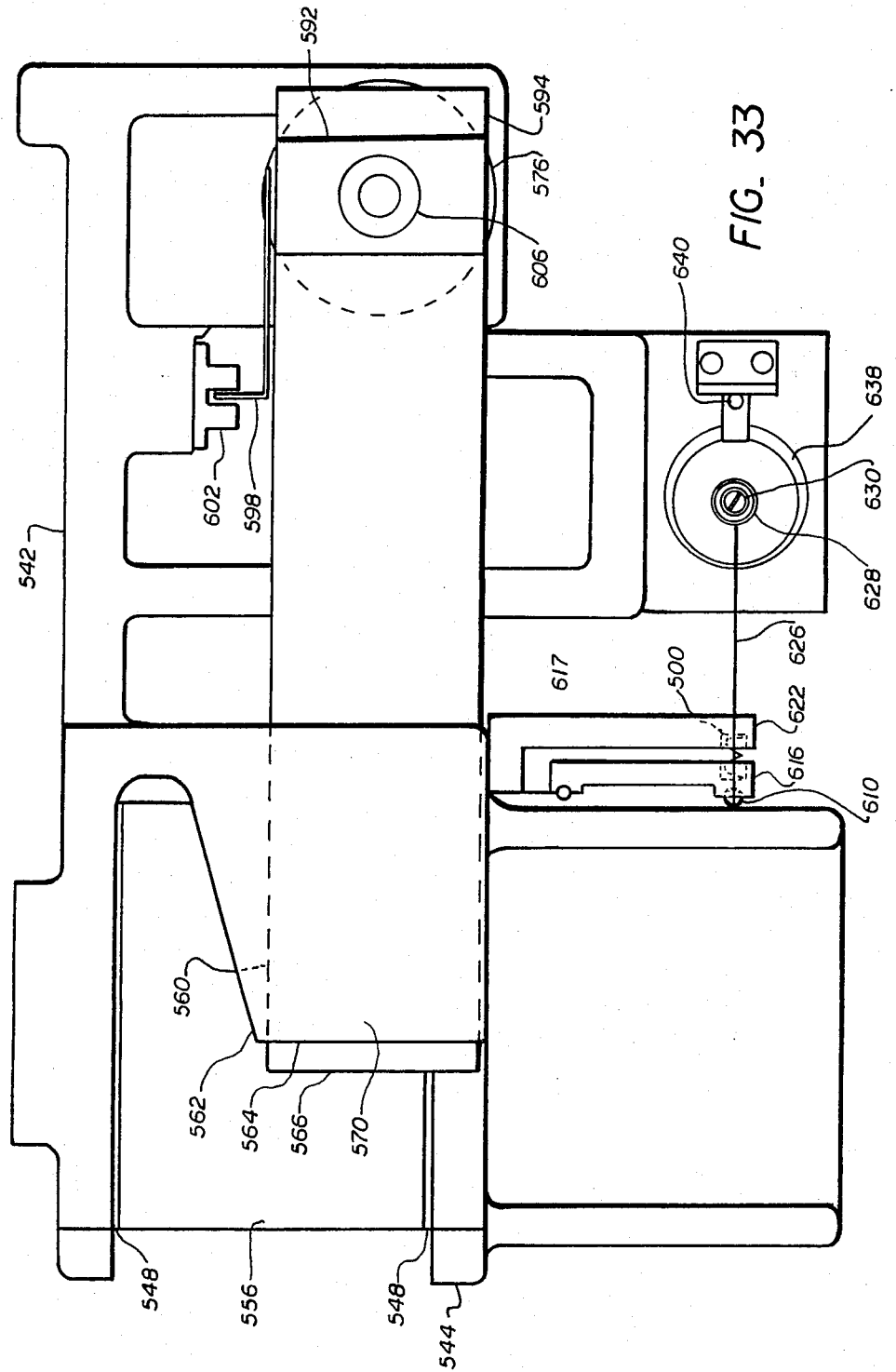
Figure 34:
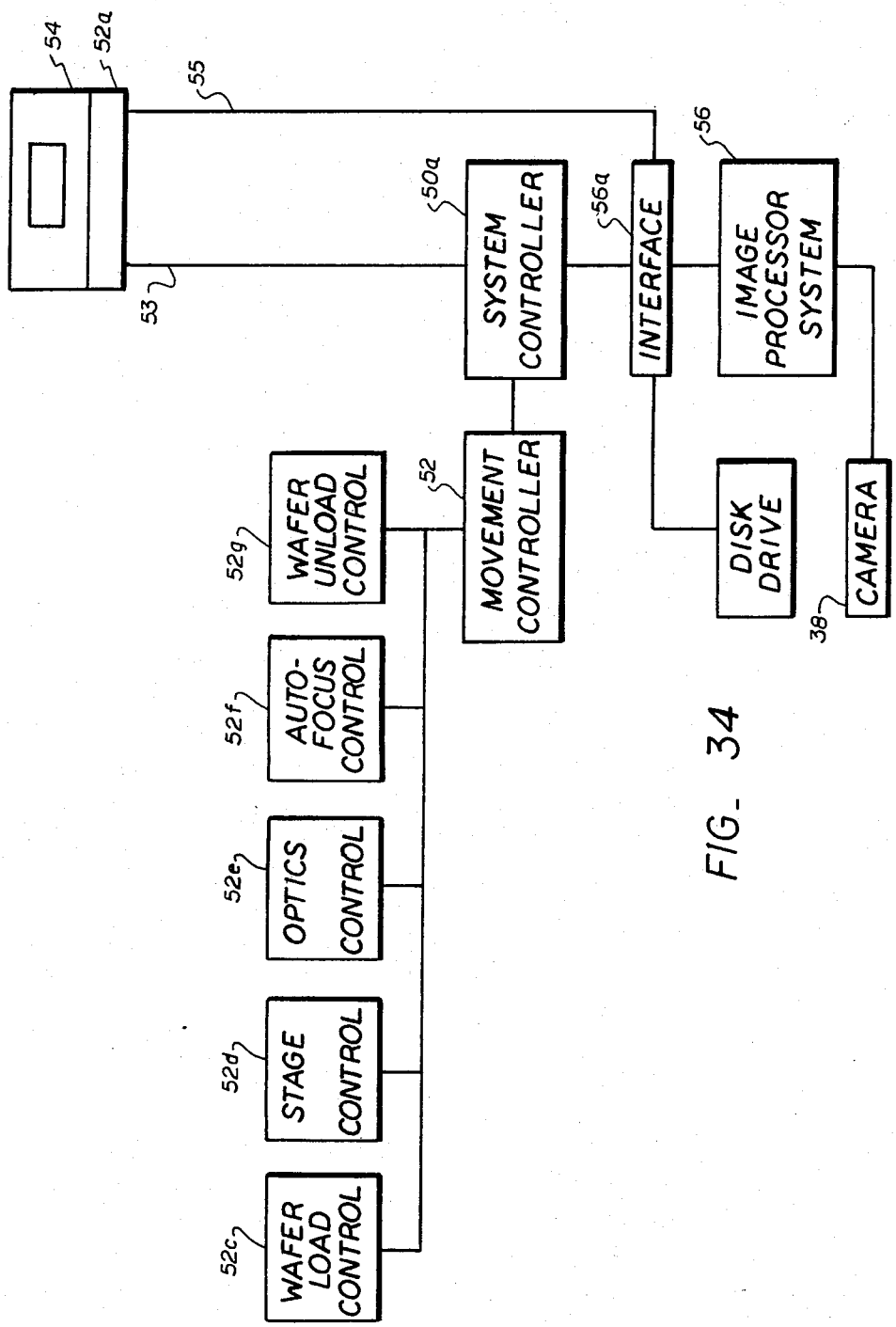
Figure 35:
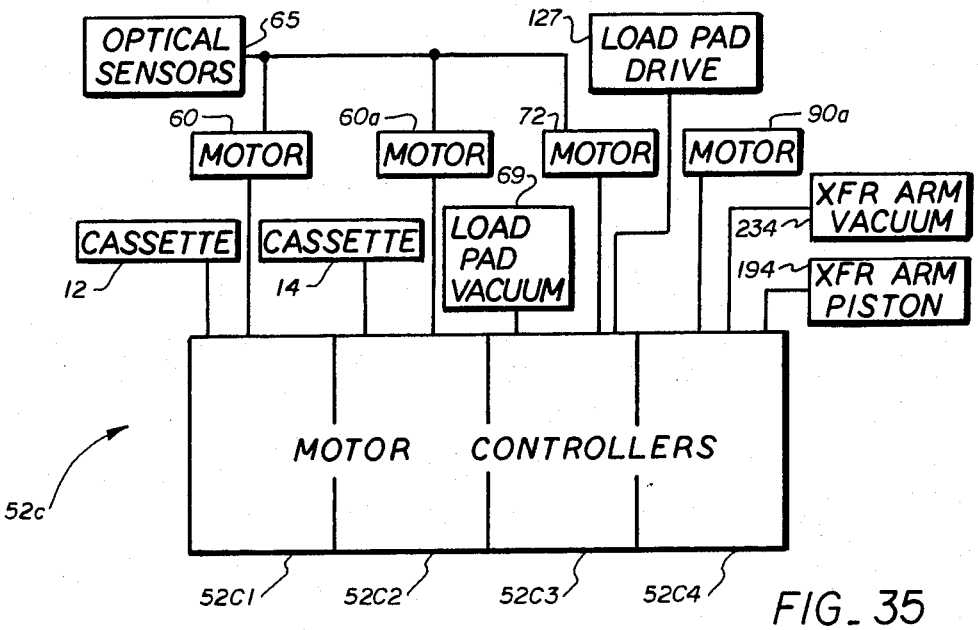
Figure 36:
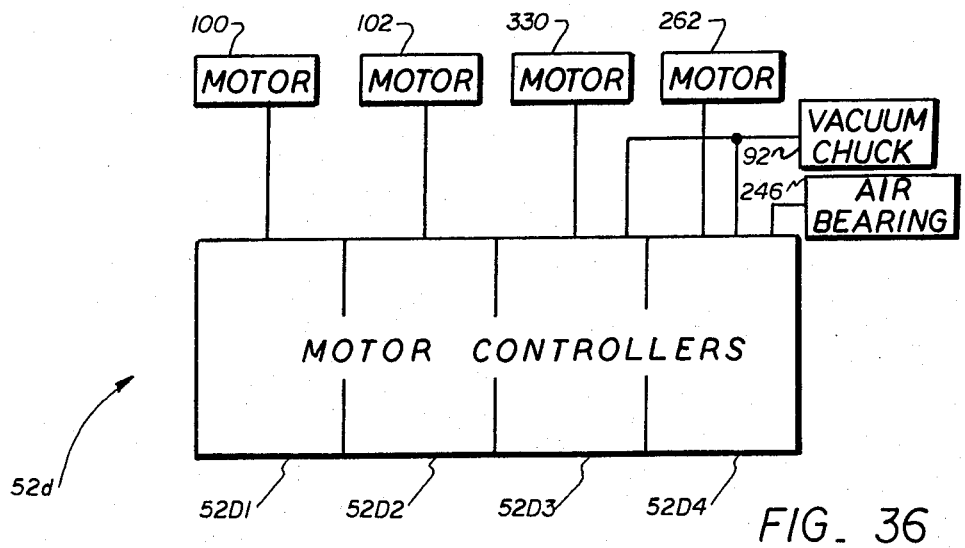
Figure 37:
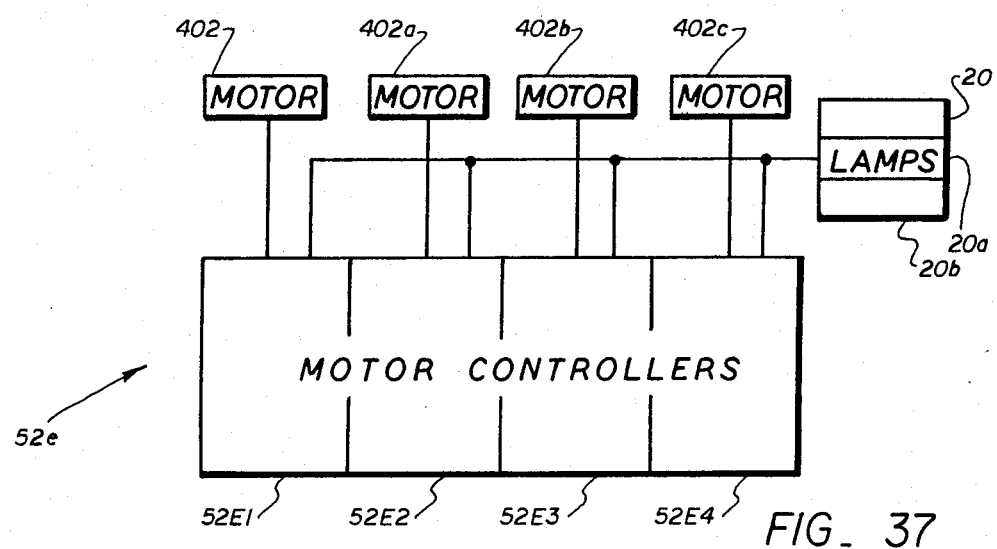
Figure 38:
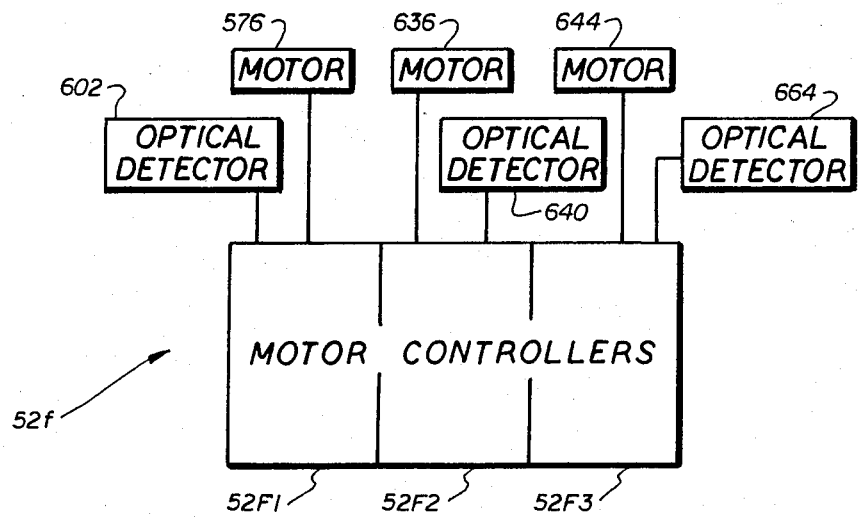
Figure 39:
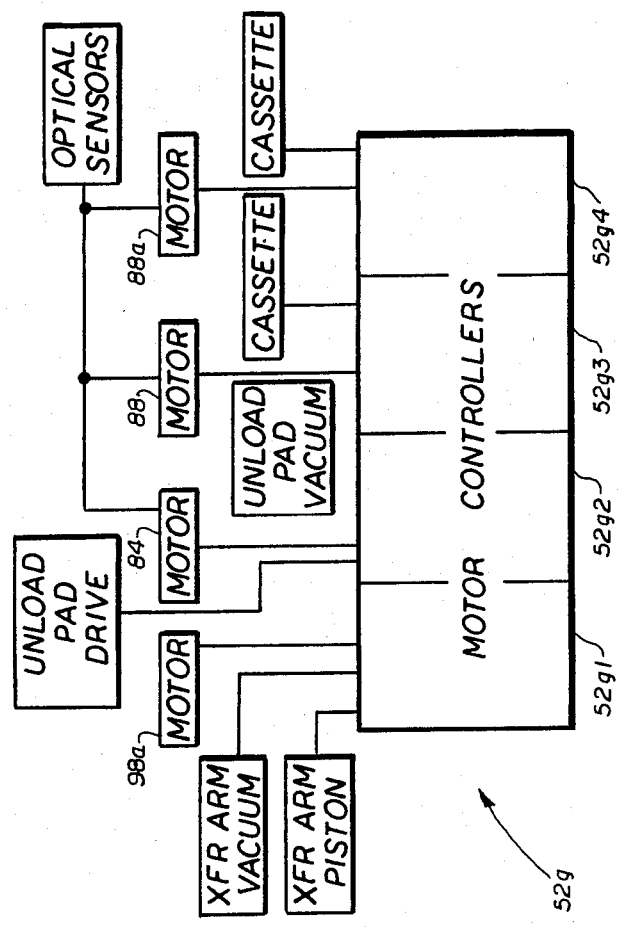
Figure 40:
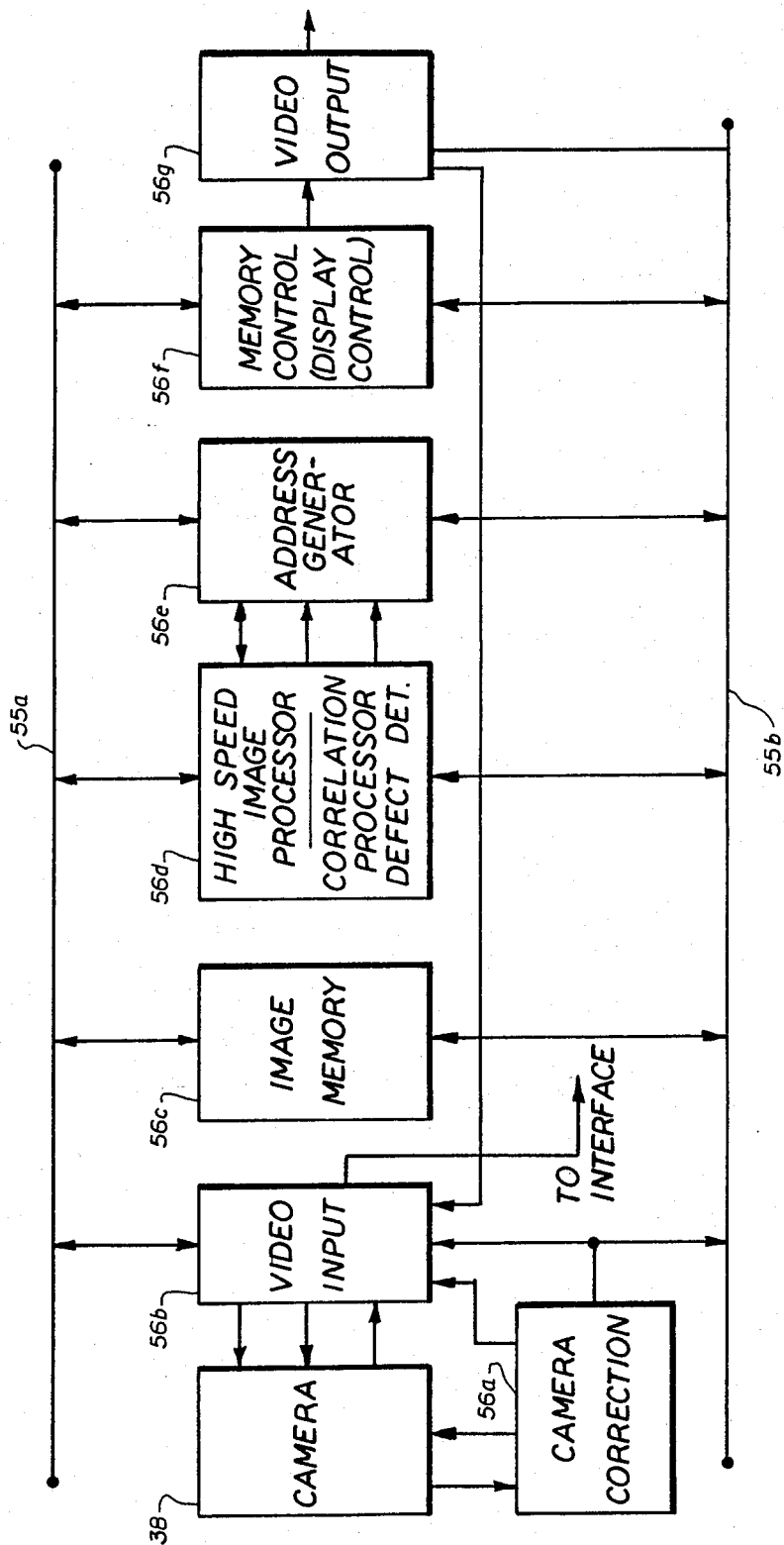
Figure 41:
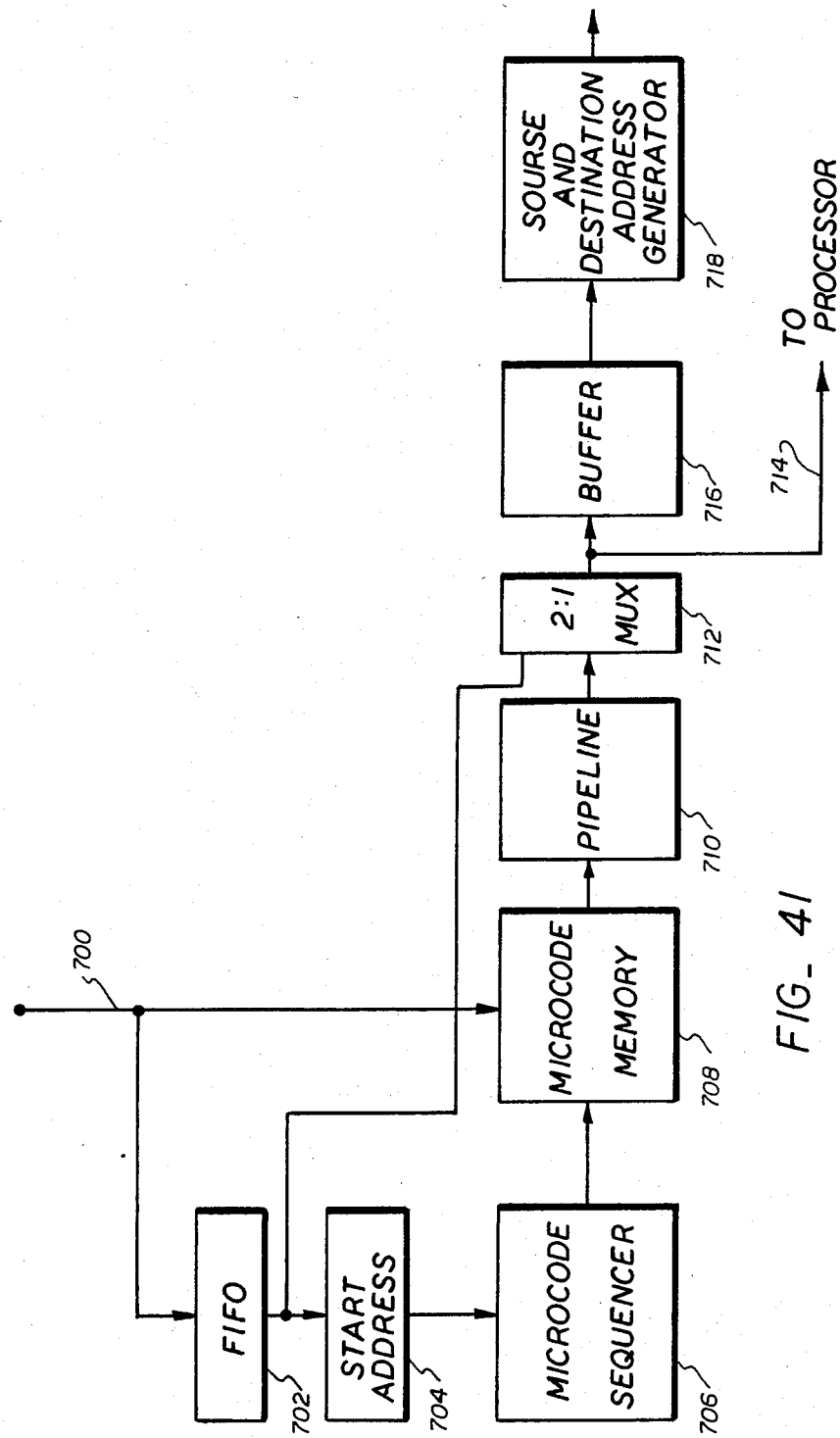
Figure 42:
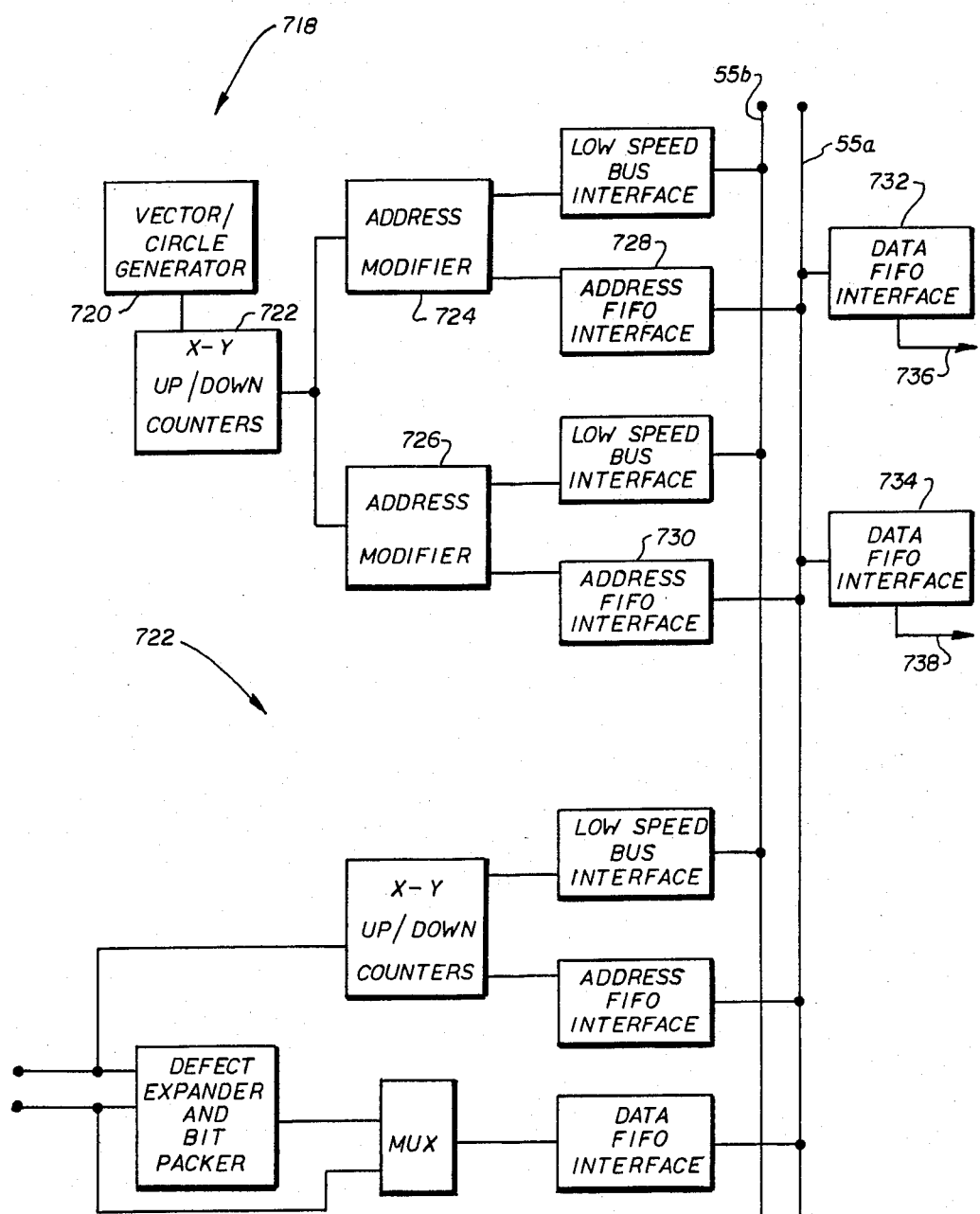
Figure 43:
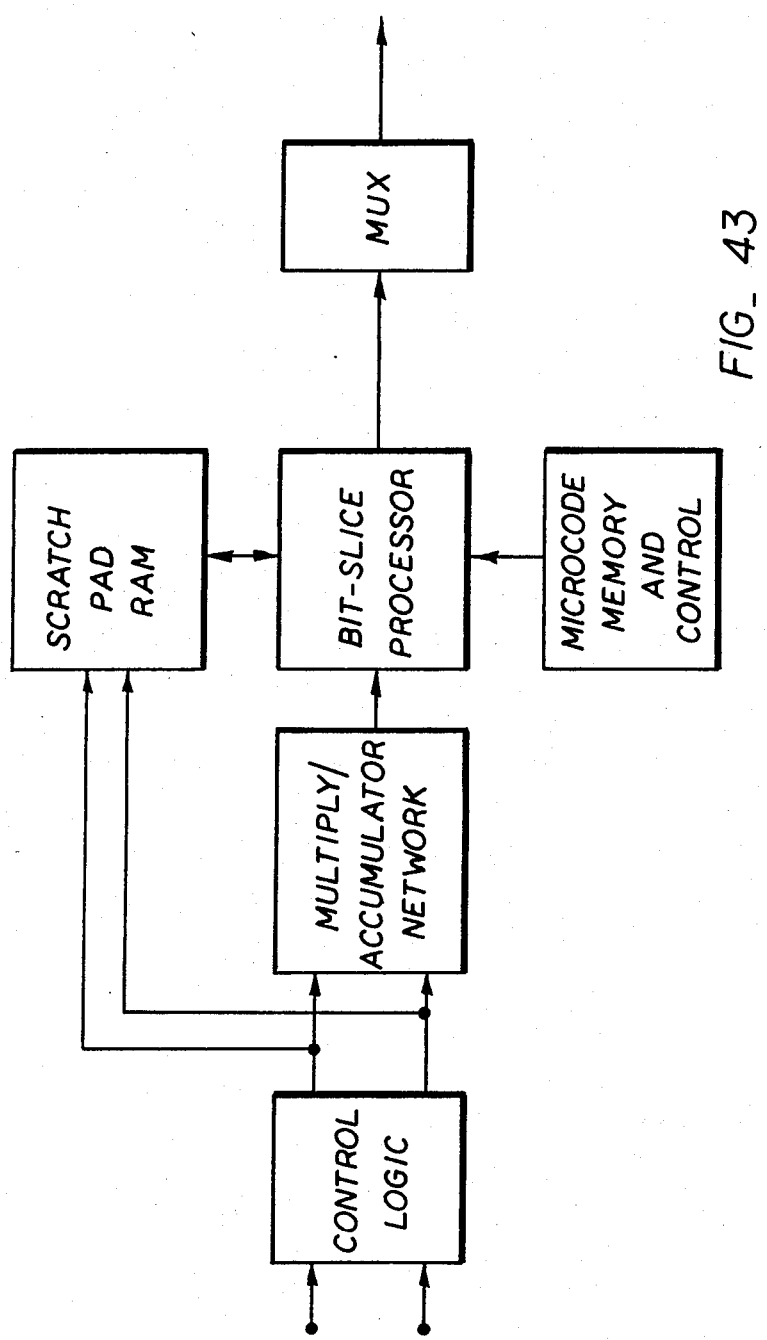

FIG. 23 symbolically illustrates the location of the image of the autofocus pupil stop within the back aperture of microscope objective;

FIG. 24 is a broken view which illustrates the masks and projected image for autofocus control;

FIG. 25 shows graphs of the photodetector output current which would result from different occlusions of each of the masks shown in FIG. 24;

FIG. 26 is a graph of the control voltage obtained by subtracting the output of photodetector (494) from the output of photodetector (488);

FIG. 27 is an isometric view of an adjustable optical module including a reticle pattern;

FIG. 28 is an elevation view of a mount used to permit X, Y, Z and theta adjustment of the lens optical module of FIG. 27;

FIG. 29 is a side view of the mount shown in FIG. 28;

FIG. 30 is an isometric view of a preferred embodiment of the turret mounting assembly of the present invention;

FIG. 30A is a side view of the position control lever arm (560A) used in a preferred embodiment of this invention;

FIG. 30B is a top view of that portion of lever arm (560A) which further illustrates the crossed flexures exployed;

FIG. 31 is a front view of the turret mounting assembly of FIG. 30;

FIG. 32 is a side view of the turret mounting assembly of FIG. 30 and illustrates the well (668) and damper (670);

FIG. 32A shows a preferred embodiment of a damper assembly (670A) used in the instant invention; and FIG. 33 is a top view of the turret mounting assembly of FIG. 30;

FIG. 34 is a simplified block diagram of the electrical control system;

FIG. 35 is a block diagram generally illustrating the wafer loading control (52C);

FIG. 36 is a block diagram generally illustrating the stage control (52D);

FIG. 37 is a block diagram generally illustrating the optics control (52E);

FIG. 38 is a block diagram generally illustrating the autofocus control (52F);

FIG. 39 is a block diagram generally illustrating the wafer unload control (52G);

FIG. 40 is a block diagram which illustrates the general features of the high-speed image processing system;

FIG. 41 is a block diagram of the high-speed address generator;

FIG. 42 is a detailed block diagram of the address generator of FIG. 41;

FIG. 43 is a block diagram of the correlation processor; and

FIG. 44 is a block diagram of the defect processor.

DETAILED DESCRIPTION OF THE PREFERRED EMBODIMENT

System Description

Figure 1:
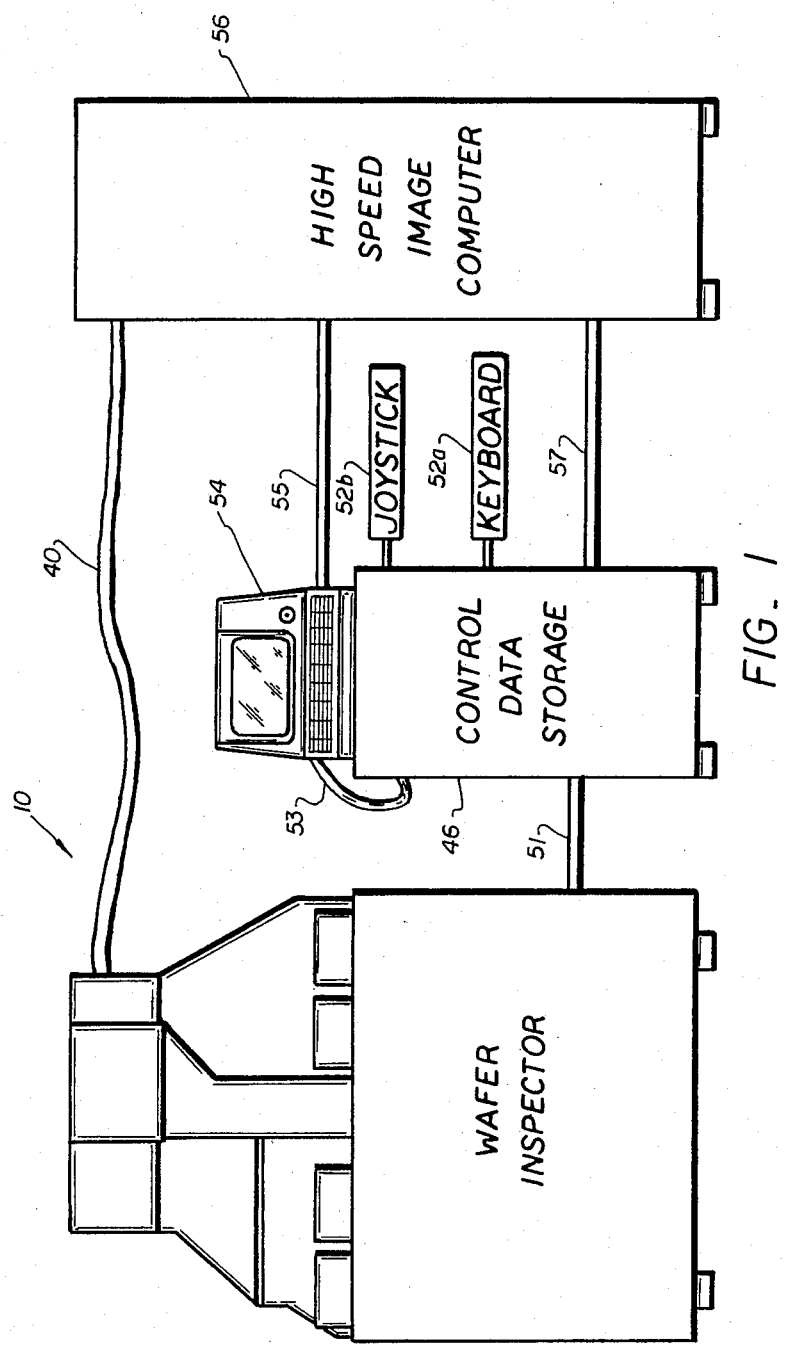
FIG. 1 is a block diagram illustrating the main elements of a wafer inspection system in accordance with a preferred embodiment of this invention.
Figure 2:
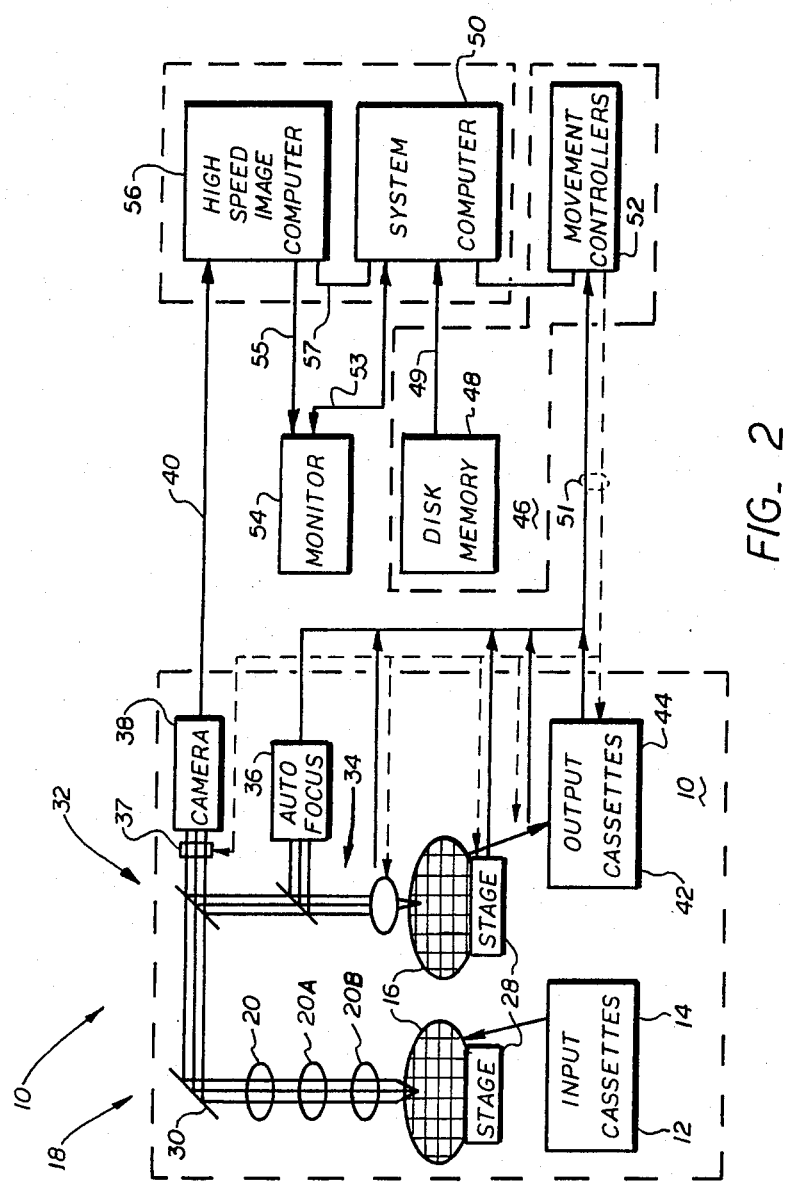
FIG. 2 is a block diagram which generally illustrates the functions performed by the wafer inspector system of this invention.
Figure 3:
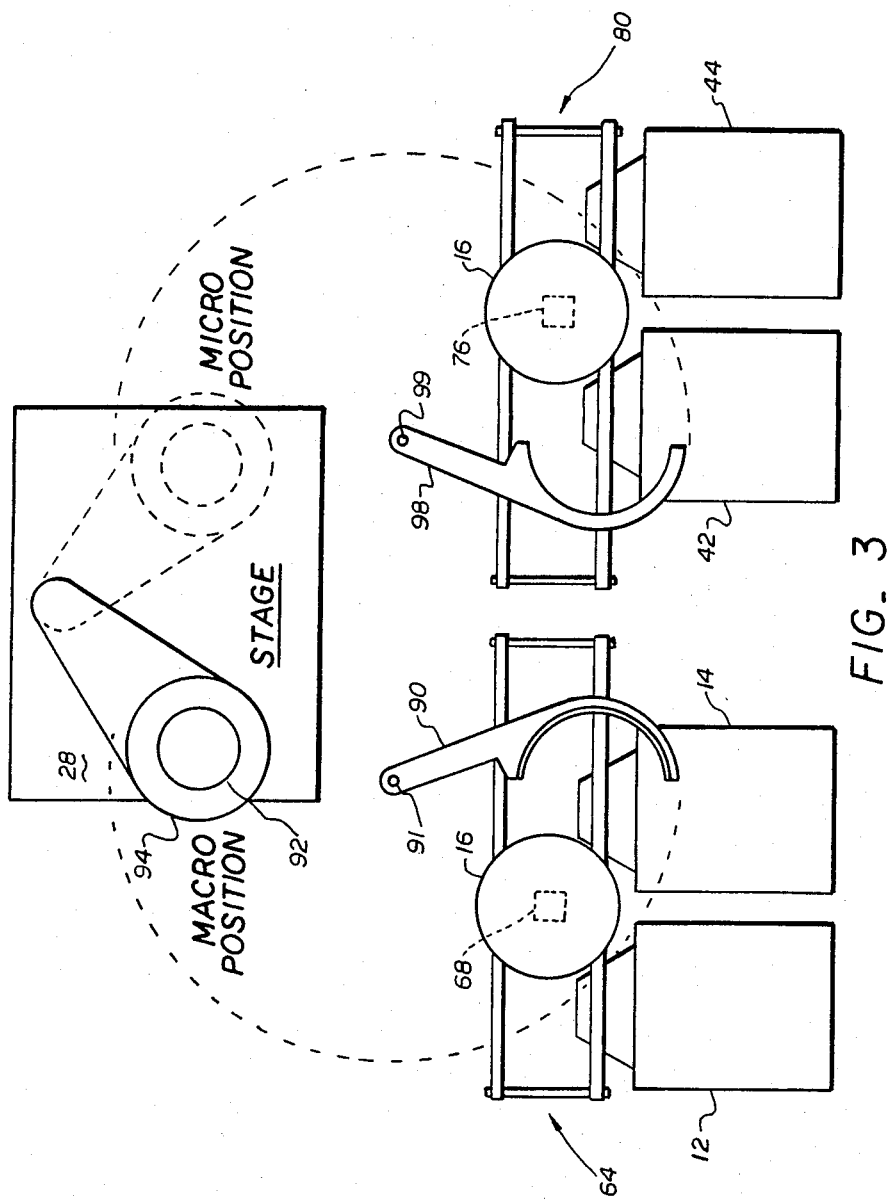
FIG. 3 is a block diagram which symbolically illustrates the automatic handling of a wafer as it passes through micro and macro inspections in accordance with a preferred embodiment of this invention.

Referring now to FIGS. 1 and 2, it may be seen that the wafer inspection system in accordance with this invention comprises three major sub-systems; the wafer inspector 10, the control and data storage 46 and the high speed image computer 56. Electrical interconnection paths are shown and are designated as 40, 49, 51, 53, 55 and 57. A monitor 54 may also be employed. The general functional inter-relationship among the sub-systems comprising the wafer inspection system may be understood by reference to FIG. 2; and the manner in which the wafer is transported from the load pad 68 to vacuum wafer chuck 92 and thence to unload pad 76 is generally illustrated in FIG. 3.

The system program is designed such that interaction with the system will be through a touch screen on monitor 54, an associated joystick 52B and by use of a concealable keyboard 52A. The monitor will display text and graphics from system computer 50 via path 53 as well as wafer pattern images from high-speed image computer 56. The use of joystick 52B is for manual movement of the wafer and for graphics. The system computer program is menu driven and during routine wafer inspection, the operations will be done entirely through the touch screen on monitor 54. The keyboard 52A is also accessible but is for use by the test designer. An entry code is required before parts of the program to be used in an inspection, for a particular class of wafer, may be selected. The procedure allows the designer to change the inspection and parameters of the micro tests. Interactive "menus" will appear on the terminal requesting the necessary input to either create an inspection, to inspect wafer(s), or to obtain data output. The part of the program which the operator routinely sees is designed such that the routine inspection of production wafers can be done with just a few instructions given to the system via the touch panel on the monitor.

Overall control of the system is provided by the system computer 50 which, among other things, insures that the various step sequences and inspection tests are performed in an orderly manner. The various sequences move a wafer 16 from a cassette such as 12 to and through the macro and micro inspection stations and finally outputs the wafer into a cassette such as 42. Each event in the sequence is accomplished in its sequence at the programmed time. However, it should be understood that a number of non-conflicting sequences are performed simultaneously to reduce inspection time to a minimum. The wafers move to and away from the inspection area simultaneously. During inspection, the system is performing the following three major functions in parallel:

(1) moving the wafer into position and focussing on and grabbing the image;

(2) loading the test data from disk storage into RAM; and (3) performing the computation required for the test. Micro inspection includes a micro-measurement and a micro-comparison. The test location is found by the use of a location image which was previously chosen manually during training and is stored in the inspection as a fundamental part of the micro-test. Micro-measurement is performed on preselected geometries. Any field can be compared (micro-comparison) to a reference image, or to the similar field in another die on the same wafer. One source for the reference image is a previously inspected die on a good wafer. The data base which was used to produce the image directly or indirectly by optical or electron beam means can then be used as a reference image. Disk memory 48 can also be programmed to provide a standard reference image from the composite of several die for comparison with the image obtained from the wafer during micro inspection, thus removing random defects from the reference image by comparison.

There are four cassettes 12, 14, 42 and 44 that are shown. The cassettes are standard types and are placed in indexers which permit the transfer of a wafer to the wafer track from the cassette and/or to the cassette from the wafer track. Any of these four cassettes can be configured as an input or output. For purposes of discussion, cassettes 12 and 14, hereinafter, will be considered to be input cassettes and 42 and 44 will be considered as output cassettes. During operation, however, a host input cassette which is empty is used as an output cassette. This is done to accommodate overflow as it is not expected that the number of wafers that pass and fail will be equal in number. These cassettes can be configured to accommodate industrial standard cassette sizes and stepping distances. Wafer sizes of approximately 75 millimeters (3 inch) to 150 millimeters (approximately 6 inch) can be accommodated.

Referring now to FIGS. 2 and 3, it may be seen that a wafer from one of the input cassettes 12 or 14 is positioned in accordance with a control signal input along signal path 51 (FIG. 1) from movement controller 52. At the proper time, the control signal will cause the wafer to be loaded onto wafer track 64. The wafer track 64 moves the wafer 16 to the load pad 68 which is located between the two input cassettes. Wafer transport arm 90 is then swung into the position shown in FIG. 3. As will be explained in detail subsequently, load pad 68 is then caused to move vertically upward so as to position the wafer above the track 64 and transport arm 90 is rotated to a position beneath and arcuately concentric with wafer 68. This places the recessed portion of the arcuate end of the arm 90 in position to accept the wafer. The load pad is next moved downward to an intermediate position so that the wafer is slightly above the shelf which is at the bottom of said recess. The wafer is now positioned to intersect the recessed side wall. The transfer arm is then swung to a position adjacent the load pad. Because the wafer is not precisely positioned on the load pad, the side wall of said recess gently and correctly moves the wafer so as to place the wafer in position above the shelf. Next the load pad is lowered to its original position and is now out of the path of the transfer arm. The wafer transport arm 90 then moves the wafer 16 above the X-Y stage 28 and the wafer is placed on the top surface of a vacuum chuck 92 that is attached to turntable 94. The turntable is in the macro inspection station.

Prior to inspection, the wafer edge and flat are found, the wafer having been loaded onto the chuck in a random orientation and alignment. The images picked up in macro view are first used to correct rotation and positioning of the wafer pattern. The wafer surface is then tested for pattern defects such as for bad spin, scratches, dust, etc., as well as gross image defect variations due to areas being out of focus or not receiving uniform exposure. Light for the macro inspection process is supplied by ring lamps 20, 20A and 20B, and the fixed macro mirror 30 transmits the reflected image to the camera 38. Camera 38 converts the image into electrical signals which are passed along path 40 to high speed image computer 56 and the image appears on the screen of monitor 54.

Once the macro inspection is completed, movement controller 52 causes the macro-micro transfer arm (described below) to shift the assembly containing the vacuum chuck to the micro inspection station on the X-Y stage 28. The wafer 16 is held on the vacuum chuck 92 by pressure caused by a vacuum pulled on the bottom surface of the wafer. As will be explained in more detail later, this handoff between the macro and micro stages is precisely performed so that the wafer is positioned for the micro inspection test. Correction for mechanical positioning errors is under the control of the system computer.

Tests are typically carried out at a number of sites, each of which is positioned automatically by the machine. A stored series of images at each site are used to correlate the image picked up from each wafer under test. Thus, the mechanical stage is not required to position to high accuracy. Correlation is used to select that portion of an approximately positioned image which is to be tested. The machine may be programmed to go to a particular series of test sites and the tests which may be different at each site can also be specified. The system is designed to lead the user through tests by a series of menus and "buttons" on a touch activated screen. This makes the system self-teaching. The sites for tests are selected by the user; subsequent wafers to be tested are simply loaded in a cassette. The machine handles and aligns and tests the wafers and routes each of them to pass or fail cassettes as a result of the test which are done entirely automatically. The sites selected for a test may or may not be unique. If the machine is to find a particular site again, it must use a series of unique references. These are automatically chosen by the program and do not necessarily have to be within the field of view.

Because of the use of objective lenses and the requirement to focus at a precise depth in the wafer pattern, each one of a plurality of objective lenses must be brought into focus prior to the time that the pixel image is recognized. As will be explained in more detail hereinafter, an autofocus unit shown as 36 in FIG. 2 automatically adjusts the focus of each of the objective lenses immediately after they are put into alignment with the optical axis. During stage movement, shutter 37 is closed so that no light reaches the tube face of camera 38 until the X-Y stage is steady and the objective focussed. Then, the shutter is opened so that the image is presented to the input of the camera. The camera beam current is controlled to allow integration of the light received during the entire time the shutter is open. Once the shutter is closed, the signal is read from the camera. The stage can move in parallel with this operation. Next, the picture image is transmitted to the high speed image computer 56 where it is compared against a standard reference, or against an image reference which was obtained from the wafer itself and stored in temporary memory.

Once the micro inspection has been completed, a second wafer transport arm 98 moves into a position adjacent vacuum chuck 92 and beneath wafer 16. The vacuum is removed from chuck 92, arm 98 then lifts up to position the wafer above chuck 92. A vacuum is pulled to hold the wafer on top of arm 98. Next, the arm 98 is caused to swing about a pivot point 99 so as to position wafer 16 above unload pad 76. Once in position, controller 52 actuates the unload pad assembly causing it to move vertically upward and lift the wafer 16 up above the arm 98. Then controller 52 causes the arm 98 to be swung so as to be free of the wafer downward path. Next, the unload pad 76 moves vertically downward to position the wafer 16 for transport on track 80. Because the computational analysis is carried on during the inspection process, the determination as to whether the wafer 16 is a "good" wafer or a "bad" wafer has already been made. The wafer 16 may be classified as "pass" or "fail" and the wafer directed to cassette 42 or 44, depending upon its classification. Movement controller 52 then activates that portion of track 80 that will move wafer 16 to the proper cassette.

Wafer Inspector

Referring now to FIGS. 4–11, in conjunction with the following discussion, the operational features of wafer inspector 10, in accordance with the present invention, may be comprehended. A welded stress frame 104 provides for rigid mounting of its base portion to a floor or other firm mounting surface. The rigid frame provides support for two heavy aluminum castings 108 and 110 which are specially constructed to maximize their damping constants. The base casting 108 sits on three air isolators 106 which rest on the welded stress frame. The upper casting 110 is firmly attached to the top surface of the base casting by means of bolts. (not shown). In this way, critical elements of the inspection stations are isolated from external movements.

Figure 4A:
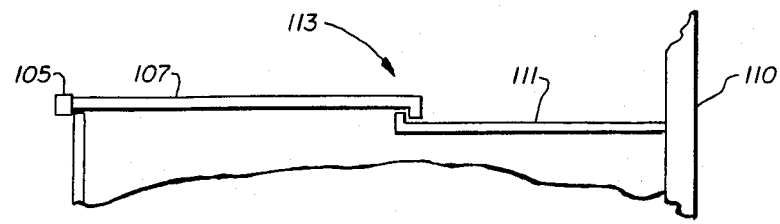
FIG. 4A is a broken elevation view illustrating the air lock at the junction between fixed and floating environmental covers.
Figure 4:
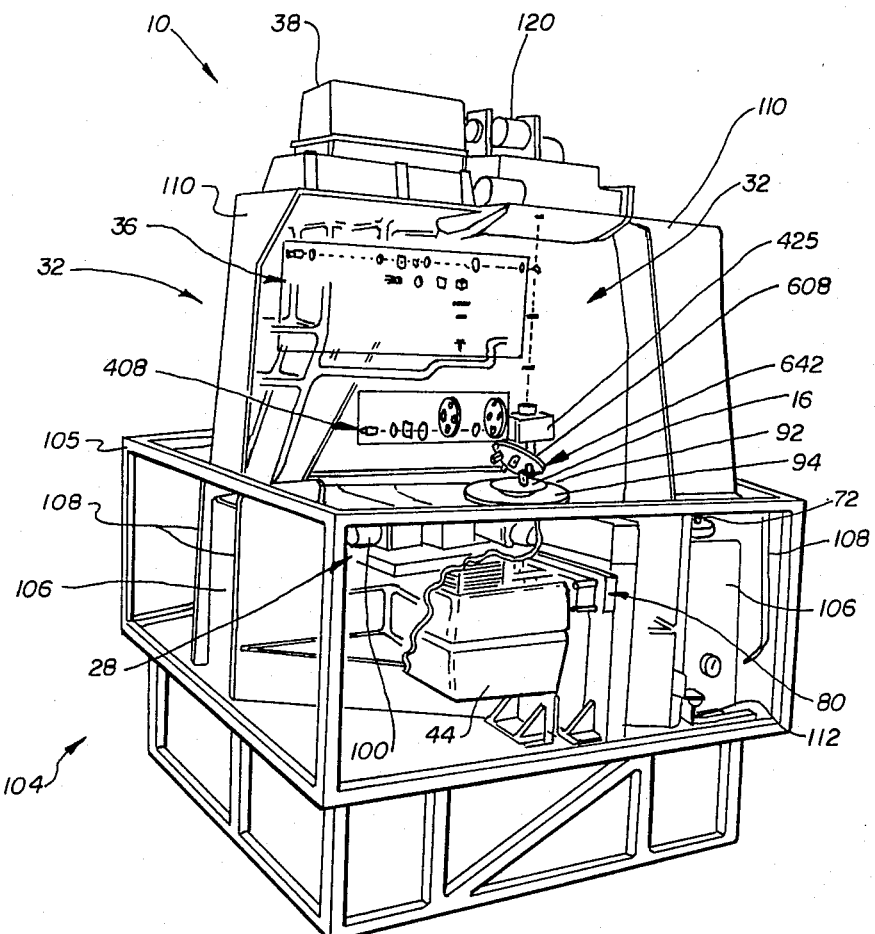
FIG. 4 is a partially broken, front perspective view of wafer inspector (10) in accordance with this invention illustrating the rigid stress frame (104) and portions of the heavy aluminum castings (108) and (110)
Figure 5:
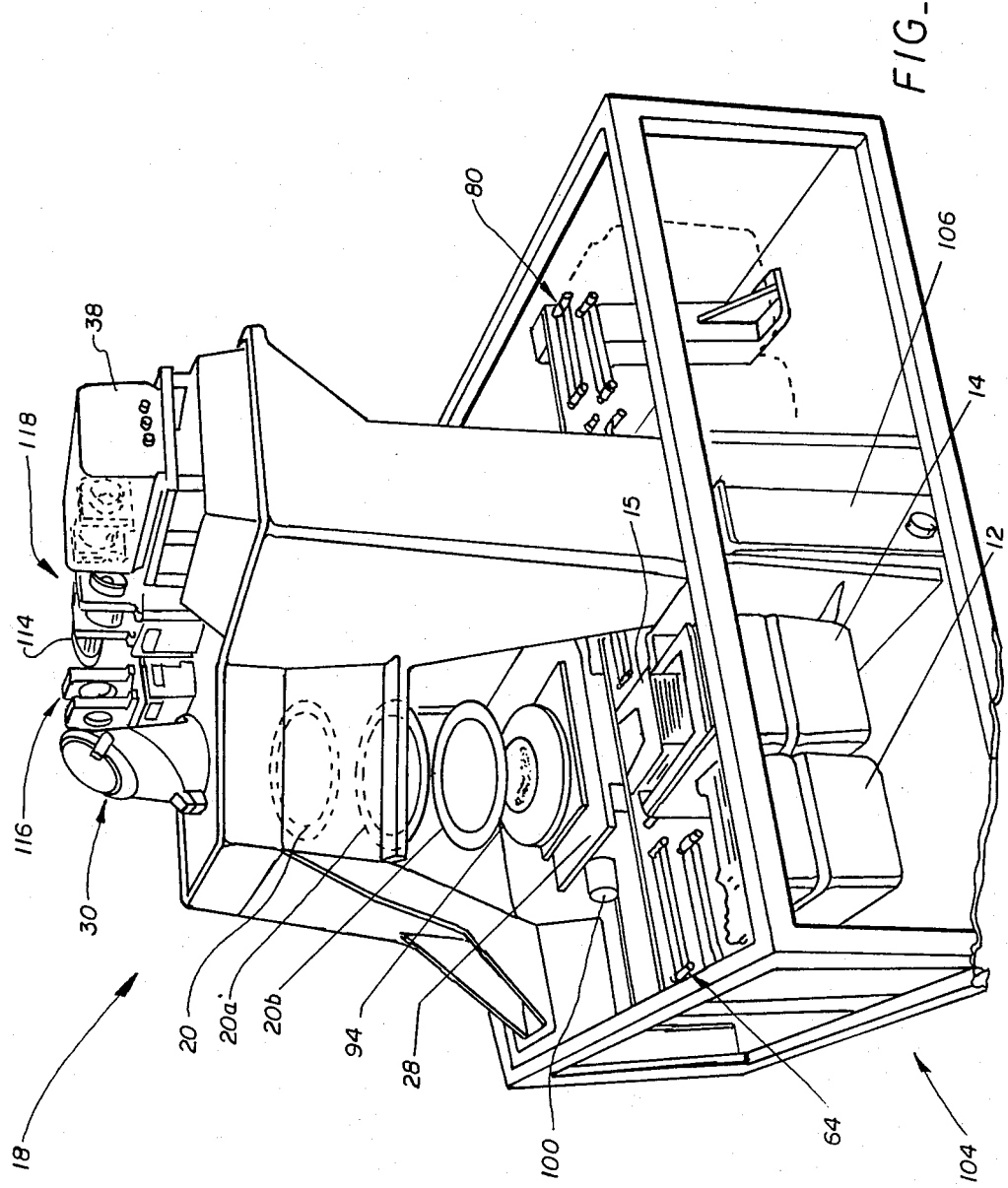
FIG. 5 is a partially broken left front perspective view of wafer inspector (10) which illustrates the macro inspection station (18), input wafer cassette loaders (12) and (14), input wafer track (64), X-Y stage (28), turntable (94), and macro optics.
Figure 6:
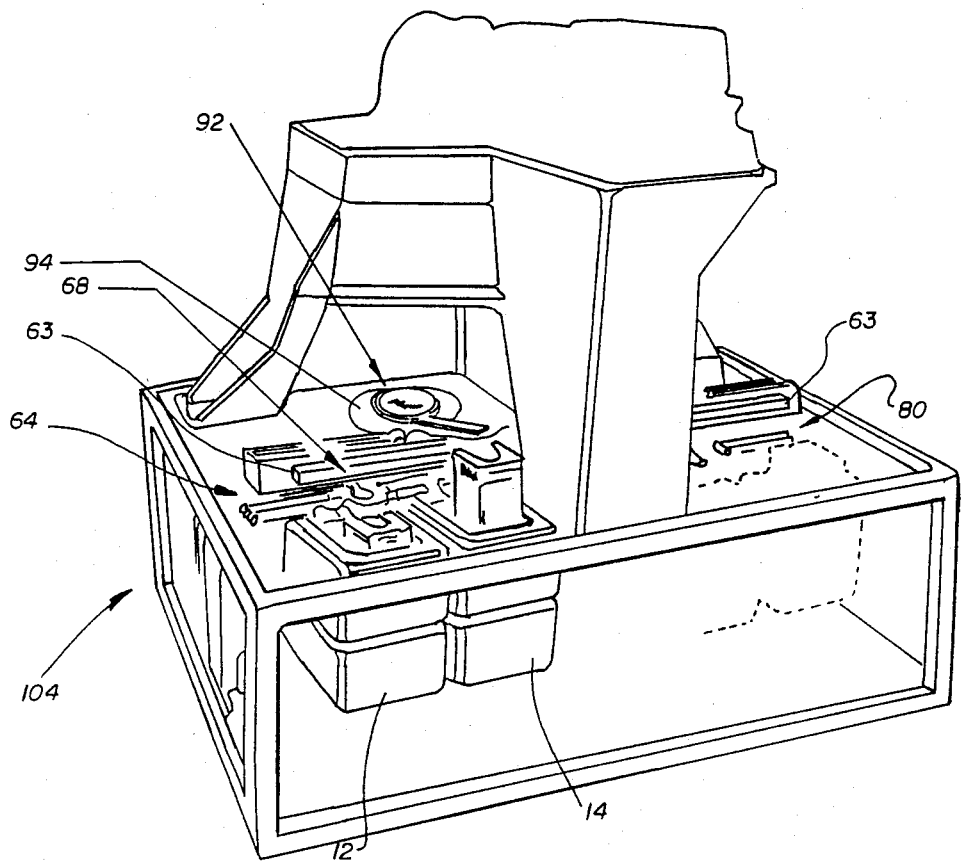
FIG. 6 is a partially broken view of wafer inspector (10) illustrating the input load pad (68) and input wafer arm (90) that are used in moving the wafer from the wafer track (64) to the wafer vacuum chuck (92)
Figure 7:
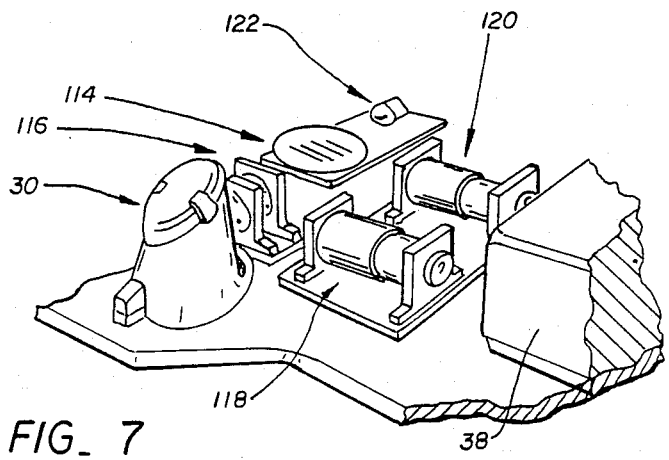
FIG. 7 is a partially broken view of the upper part of wafer inspector (10) which illustrates in more detail the macro optics and the interchangeability of the moveable macro mirror (114) and the pentaprism (122)

Although not illustrated in detail, so as to not clutter the drawing, the welded stress frame provides mounting facilities for the wafer handling system. This isolates the moveable elements from the inspection. The stress frame also provides for the mounting of environmental covers, see FIG. 4A, which surround the area through which the wafer passes during inspection so as to provide environmental control. Environmental covers are also attached to the floating portion of the wafer inspector. In order to maintain isolation between the stress frame and floating inspection station, the environmental covers are not interconnected but lie in different planes, which overlap, and are formed to provide a channel adjacent the edge. One such arrangement is shown in FIG. 4A where a fixed cover 107 is attached to fixed member 105 of stress frame 104, and a floating cover 111 is attached to aluminum casting 110. This creates an air lock 113 between the two overlapping covers because the interior of the wafer inspector is maintained at a positive pressure. Air passing through the air lock under pressure prevents outside contaminants from entering the inspection area.

Wafer Transport

The wafers to be inspected are contained in input wafer cassette loaders 12 and 14 and these cassette loaders are positioned as shown adjacent the input wafer truck 64. If a wafer is to be loaded onto the wafer chuck 92, the enabled loader outputs a wafer 16 onto an "O" ring belt track 64 where it moves to a position midway between the cassette loaders 12 and 14. While an "O" ring belt track has been shown, as a preferred way to move the wafer, it should be understood that other techniques may be used to provide the desired transport. For example, a walking beam may be used, or direct moving arms may be adapted to accept the wafer and transport it to the load pad. It is then raised up off the belt by a load pad 68, and the wafer transfer arm 90 swings underneath the wafer 16.

Figure 8:
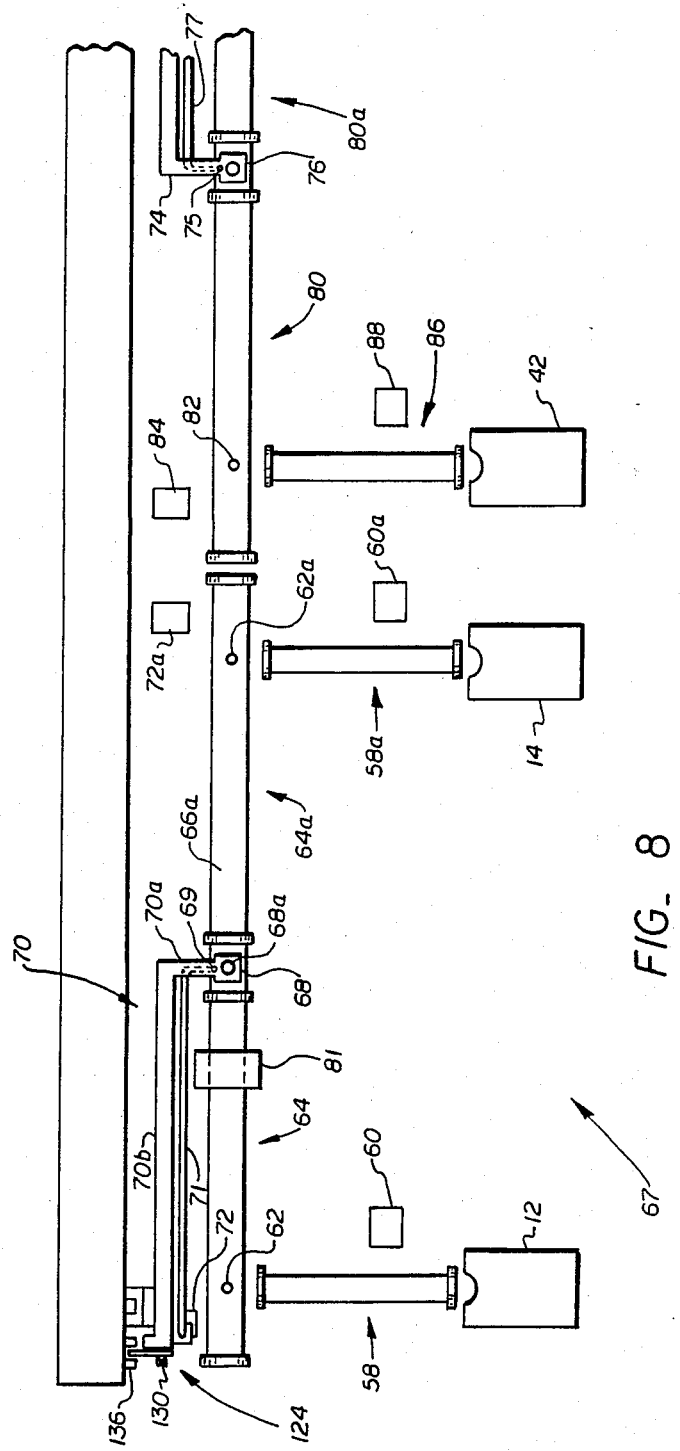
FIG. 8 is a partially broken top view of wafer loading assembly (67), load pad (68) and associated actuator assembly, and illustrates wafer tracks for delivering a wafer to load pad (68) and the vacuum line (71) which provides holding force for the wafer.
Figure 8A:
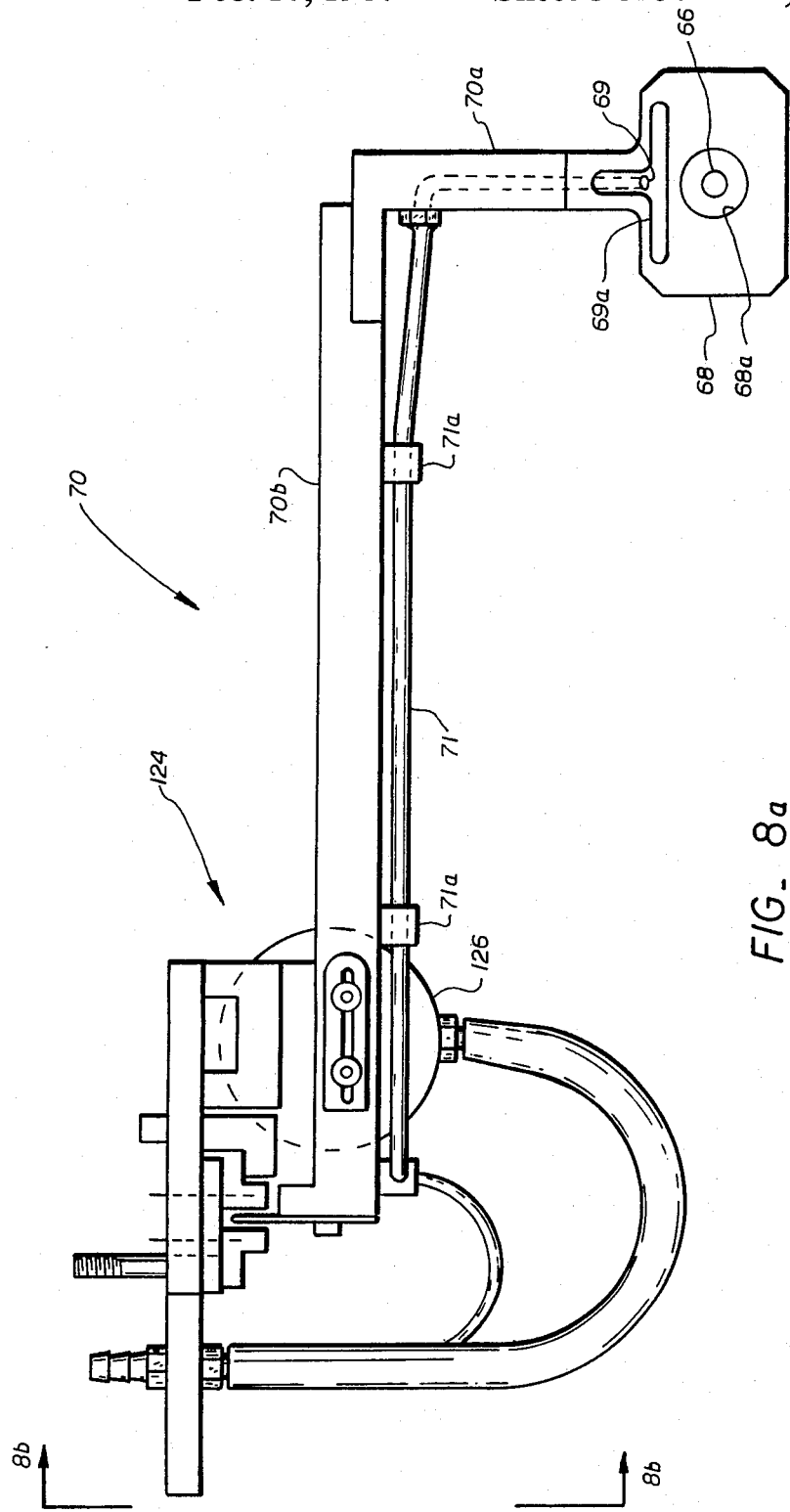
FIG. 8A is a top view of the load pad actuator assembly arm (70) and ball slide assembly (124)

The manner in which wafer transport is accomplished can be better understood by referring to FIGS. 8–11. Referring now to FIGS. 8 and 8A, a loading and unloading assembly 67 is shown which includes, for example, cassettes 12 and 14, "O" ring tracks and the load pad 68 attached to a vertical drive arm 70. A wafer to be loaded from cassette 12 is indexed into "O" ring track 58 which is driven by motor 60. An optical transmitter 62 positioned between and below the upper track 64 sends its optical signal vertically upward to an optical receiver mounted in optical rail 63 (see FIG. 6). Interruption of the light signal by the wafer 16 stops motor 60 and activates motor 72 which drives track 64 so as to carry the wafer toward load pad 68. An optical transmitter 66 is positioned below the load pad aperture 68A and the light signal is transmitted through the aperture 68A to an optical receiver in the rail 63. Interruption of the light signal from transmitter 66 notes the presence of the wafer on the load pad 68 and other programming information is used to determine what is to happen next. For example, if only selected wafers are to be subjected to the inspection, the wafer can be passed on along the track to be deposited in one of the other cassettes. If the wafer is to be subject to inspection, the wafer is stopped on the load pad 68, which is formed as a part of drive arm 70.

The structure of the drive arm and the ball slide and air piston drive arrangement are shown in more detail in FIGS. 8A and 8B. The drive arm 70 is L shaped with load pad 68 attached to the end of the transverse member 70A. A vacuum line 71 is attached to the edge of the longitudinal member 70B by mounting clamps 71A in a well known manner. The vacuum line 71 passes into the transverse member 70A adjacent to the juncture of the transverse and longitudinal members. The vacuum line 71 runs within the transverse member to recess 69 in "T" shaped cut out 69A. Thus, a vacuum can be pulled which is used to hold the wafer 16 on load pad 68 during vertical movement thereof.

The drive arm 70 is held in a horizontally aligned position by a ball slide assembly 124, which is driven vertically up and down by a pair of air pistons 126 and 128. Air piston 126 has air feed lines attached in a well known manner to air lines (not shown) via couplings 138 and 139 and air piston has air feed lines attached to couplings 140 and 141. As air feed lines and air supply sources are well known they are not shown to avoid drawing clutter. The manner in which the air pistons operate is described in more detail hereinbelow. Once a wafer has been selected for inspection it is stopped on load pad 68 by the interruption of the light signal through aperture 68A. This stops the wafer track with the wafer resting on load pad 68. A vacuum is drawn via aperture 69 and vacuum line 71 to hold the wafer in place. The air pressure is applied to the air pistons to drive the ball slide arrangement 124 upward. The amount of upward displacement is controlled by a flag 130 and, in particular, cut outs 132 and 132A, which operate in conjunction with optical detectors 134 and 136, to repeatably set the displacement. It is to be noted that the drive arm 70 and, of course, its associated load pad may rest in any one of three positions. At bottom. At top or maximum displacement. And at an intermediate position. Initially the drive arm is raised to its top position by the application of air to air pistons 126 and 128. Next, the wafer transfer arm 90 is swung under the drive arm 70 and is positioned on the other side of the wafer. Then the drive arm 70 is lowered to its intermediate position which positions the wafer slightly above the recess 232 in the wafer transfer arm 90. As could be expected the wafer setting on the load pad 68 is not aligned so as to fit comfortably in recess 232 without some adjustment. For this reason a sidewall 231 is included on wafer transfer arm 90 to align the wafer as said arm is maneuvered into a position adjacent load pad 68. Thus, it is seen that the drive arm assembly provides a controlled vertical motion upward from a rest position to a predetermined height above the "O" ring track and a motion downward from said predetermined height to a position slightly above the recess 232 in arm 90 and also to a position slightly below the "O" ring track so as to be in position to readily accept a wafer from the track.

The diameter of load pad 68 is smaller than the wafer so that when the wafer transfer arm 90 swings adjacent the wafer, after the load pad is lowered to its intermediate position, the wafer is aligned in the recess 232 without interference from load pad 68. Finally, the load pad can pass through the aperture in the wafer transfer arm 90 as the load pad 68 moves downward. Thus the wafer is transferred to the wafer transfer arm for transport.

In order to ensure that the wafer inspector 10 is properly aligned and ready to perform inspection test 5, an alignment wafer 79 is first run through the inspections. The alignment wafer is stored in garage 81 as shown in FIG. 8C. Garage 81 includes a top 81A, downwardly extending sidewalls 81B and partial floor elements 81C extending inwardly from the lower end of each of the sidewalls. When not in use, the alignment wafer 79 is stored in the garage which is then positioned above the wafer track 64A. When the alignment wafer is to be used, air piston 87 of actuator assembly 85 is disabled and coil spring 89 acts to drive the garage 81 downward to its lowest position. The vertical movement is maintained by guide assembly 83. As may be seen in FIG. 8C, the wafer 79 is deposited on the wafer track 64A and the partial floor elements 81C are below the top surface of the O-ring belts of track 64A. The track 64A, driven by motor 72A (FIG. 8), is enabled to move the wafer toward load pad 68 from which it will be passed through the wafer inspector as the alignments are checked and adjustment made as necessary. Once back to the O-ring track the alignment wafer is directed to a position within the garage. The air piston 87 enabled which raises the garage and wafer above the track so that normal wafer inspections may be effected.

As has been previously noted, it is possible to program the computer so that any one of the cassettes may be used as the input or output, and, of course, the output cassettes can be designated as pass and fail. Further, the inspection can be limited to specifically designated wafers in each cassette. If a wafer is not selected for test, it will be moved past load 68 and along track 64A to track 80. If cassette 42 is designated to accept uninspected wafers, optical detector 82 will detect the presence of the wafer and cause the drive motor 84 to stop. The wafer is then positioned adjacent "O" ring track 86 and motor 88 will then be activated to carry the wafer to cassette 42. Conversely, when wafer 16 has been inspected, wafer transfer arm 98 will move the wafer from the vacuum chuck 92 to a position above unload pad 76. As described for load pad 68, unload pad 76 will be activated to rise vertically and lift the wafer 16 from the transfer arm 98. The vacuum in the arm having been removed so that the wafer readily moves upward with the motion of the unload pad. A vacuum is applied to recess 75 of unload pad 76 via line 77 to hold the wafer on the unload pad 76 during downward motion.

The transfer arm 98 is then moved away and the unload pad actuator arm 74 moves vertically downward. The wafer can then be moved to the left or right on track 80 or 80A, respectively, and the direction of motion will depend upon the results of the inspection and the location of the pass and fail cassettes. Only a part of the track 80A is shown. Further, not any part of cassette 44 and its associated "O" ring track have been shown. It should be understood, however, that operation of these elements will be similar to that described for cassette 42 and its associated optical detector and "O" ring tracks. Consider the wafer to have passed inspection and is to be lodged in cassette 42. Motor 84 will cause track 80 to move the wafer from unload pad 76 past optical transmitter 78 and over optical transmitter 82. Then, belt 80 will stop and motor 88 will activate belt 86 to move wafer 16 into cassette 42.

Wafer Transfer Arm

Figure 9:
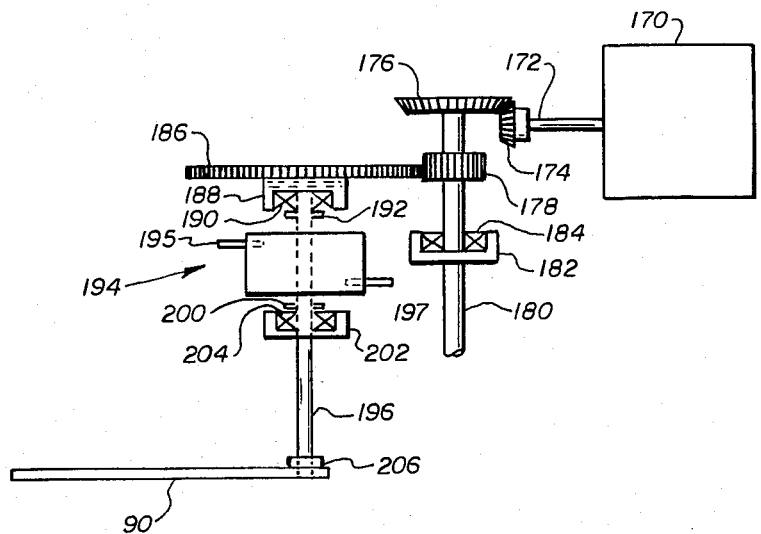
FIG. 9 is an elevation view of the drive assembly for the wafer load transfer arm (90)
Figure 10:
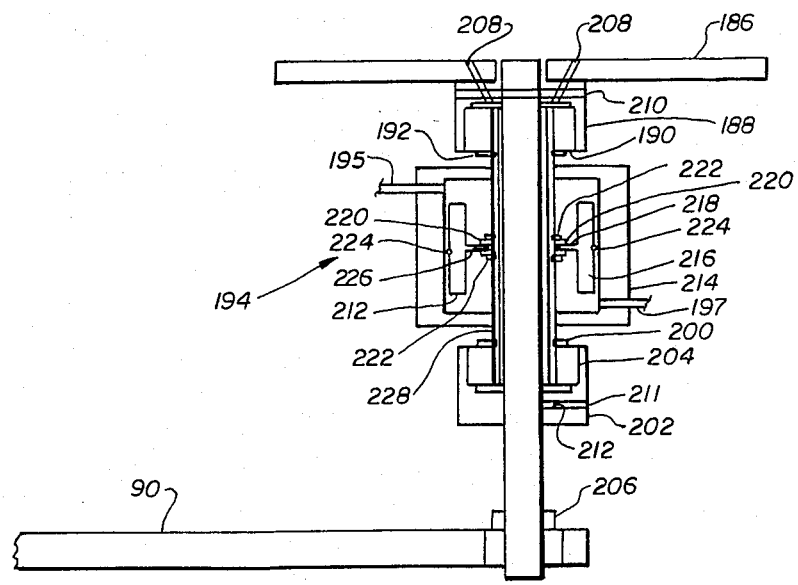
FIG. 10 is a sectioned elevation view of the air piston (194) and drive assembly for wafer transfer arm (90)
Figure 11:
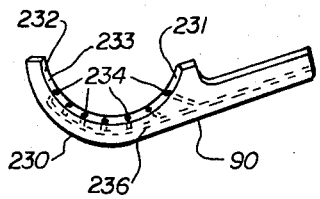
FIG. 11 is a partially broken top view of the distal end of wafer transfer arm (90) illustrating the the recess (232) in wafer holding member (230) and the vacuum holes (234) in the recess.
Figure 11A:
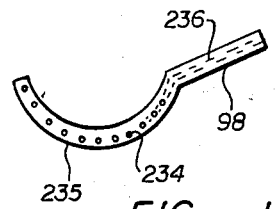
FIG. 11A is a partially broken top view of the arcuate part of wafer transfer arm (98).

The manner in which the wafer transfer arms 90 or 98 are driven to move a wafer between the load pad 68 or unload pad 76 and the vacuum chuck 92 may be understood by reference to FIGS. 9-11. A stepper motor 170 has a shaft 172 connected to a bevel gear 174 which drives a bevel gear 176. A pinion gear 178 is attached to a vertical drive shaft 180 that rotates in bearing 184 that is held in bearing support block 182. The drive shaft 180 is attached to bevel gear 176, thus the motion of the stepper motor 170 causes pinion gear 178 to rotate. A spur gear 186 is driven by the pinion gear 178. It should be noted that the pinion gear 178 is considerably wider than the spur gear 186. Spur gear 186 is connected to an upper bearing support block 188 by pins 208. These pin the gear to the hub. Pin 210 is used to pin the hub to the wafer arm drive shaft 196. A lower bearing support block 202 has a threaded aperture 211 in which a set screw 212 is threaded to lock it to the shaft. Ball bearings in the upper and lower bearing support blocks are designated 190 and 204, respectively, and snap rings 192 and 200 hold the ball bearings in position in the upper and lower support blocks.

Intermediate the upper and lower bearings is an air piston 194 which has an air cylinder housing 214 that encloses an air cylinder piston 216 that includes a piston drive connector 218. The snap rings 222 below and above the piston drive connector 218 lock the air cylinder piston 216 to the air cylinder shaft 228. O rings 224 and 226 minimize leakage around the cylinder 216. Air may be applied via ports 195 or 197 depending upon whether the wafer arm is to be driven down or up, respectively.

Thus, it is seen that the use of the wide pinion gear 178 allows a controlled vertical movement of the wafer tranfer arm 90, for example, while still allowing for drive motion, when the arm is in either the upper or lower vertical position. As will become clear in the subsequent discussion, the transfer arm is driven at its lower vertical height to pass under the load pad prior to accepting the wafer. In order to position the wafer 16 on wafer vacuum chuck 92, the transfer arm 90 moves lateraly at its highest vertical position. Once the transfer arm is positioned above the chuck, the transfer arm is dropped vertically downward to the transfer the wafer 16 to vacuum chuck 92. The transfer arm 90 is then moved out of the macro inspection area.

To pick up a wafer from load pad 63, the load pad is raised to position the wafer at its highest level and to place the load pad actuator arm 70 above the path of transfer arm 90. The wafer arm 90 swings underneath the raised load pad 68. The load pad is dropped down to the intermediate position which positions the wafer 16 a few millimeter above shelf 233 in recess 232. Transfer arm 90 is then moved to a location adjacent the load pad and the side wall 231 of recess 232 gently moves the wafer so that it is correctly positioned as the shelf 233 of recess 232. The vacuum or load pad 68 is released and the load pad is dropped down to its original position. This motion causes the wafer to be deposited in the arcuate recess of arm 90. The arcuate portion is designed to accept the particular size wafer being inspected and as noted hereinabove, the arcuate portion includes a recess 232 that provides a shelf 233 on which the bottom edge of the wafer 16 may rest. Note that there is no gripping action caused by the wafer holding member 230. The recess is sufficient to insure that the edge of the wafer is not forced against the side wall of the recess and the shelf extends radially inward far enough to provide adequate support. In addition to the force of gravity, which tends to hold the wafer in position, a series of vacuum holes 234 are provided in the shelf and these interconnect with vacuum line 236 by which a vacuum pressure is drawn to hold the wafer in position during transport.

Next, the wafer arm 90 is driven by stepper motor 170 until the wafer is positioned over the wafer chuck 92 which at this time is centered in the macro position. Air pressure is then applied via air inlet 195 of air cylinder 214 causing the wafer arm to move vertically downward and deposit wafer 16 on the wafer vacuum chuck 92. It being understood that the vacuum pressure holding the wafer 16 in the recess 232 of wafer arm 90 is released so as to avoid any undue pressure on the wafer 16 when the underside of the wafer encounters the flat upper surface of the chuck 92. The stepper motor 170 than drives the wafer arm into a neutral position between the X-Y stage assembly 28 and the input load pad 68.

In removing a wafer 16 from the micro inspection station, the wafer transfer arm 98 is used. The drive motor moves the arm in its lowermost position to a position adjacent the vacuum chuck 92 and beneath the wafer 16. The chuck holding vacuum is released. The arm moves up and a vacuum is drawn through the vacuum holes 234 in the top of the arcuate position 235. It is to be noted that a recessed position is not required for the arm 98, and therefore the wafer rides on the top surface being held in place by vacuum.

Vacuum Chuck

The wafer vacuum chuck 92 is a cylindrically shaped member having a flat end wall 93 and is positioned on the X-Y stage 28 so as to centrally locate the wafer when the stage is in either the macro or the micro inspection station position. The diameter of the flat end wall 93 of chuck 92 is smaller than the wafer diameter and is small enough to allow the passage of either the wafer holding members 230 or 235 when the wafer is being deposited on or removed from the top surface of the vacuum chuck 92. An example of a size comparison is a 10 centimeter wafer which will be held by a 7.5 centimeter chuck. The chuck flatness, relative to the plane which is perpendicular to the optical axis, is 25 microns. The wafer is held to the chuck by a vacuum. As explained hereinabove, the wafer arm motion causes the holding member 230 to deposit the wafer 16 centrally on the chuck 92. The vacuum on the wafer arm 90 is released and the arm is retracted. Next, a vacuum is pulled on the chuck 92 to hold the wafer in fixed position thereon. The chuck 92 is releasably attached to turntable 94 so that different size chucks may be used to accommodate different size wafers.

X-Y Stage

Referring now to FIGS. 12-15, the manner in which the wafer 16 is positioned for inspection in either the macro or micro optical stations may be understood. The X-Y stage 28 is a crossed roller type stage which is well known. The X-Y stage 28 provides 7 inches of travel in each of two orthogonal axes. The stage is designed to provide sufficient motion to view the entire surface of a 6 inch diameter wafer with the travel centered on either the macro or the micro optical axis. Because these axes are 10 inches apart, a macro-micro transport arm 244 was developed to move the wafer 16 between the optical axes in a minimum of space.

Macro-Micro Transport Arm

The assembly comprises a base plate 240 which is mounted to the top surface of the X-Y stage 28 by means of mounting screws 242. A macro-micro transport arm 244 is supported above the base plate 240 by air bearings 246. The transport arm 244 is arranged to pivot around pivot 248 which is concentric with the central axis of a belt drive motor 330.

Figure 12:
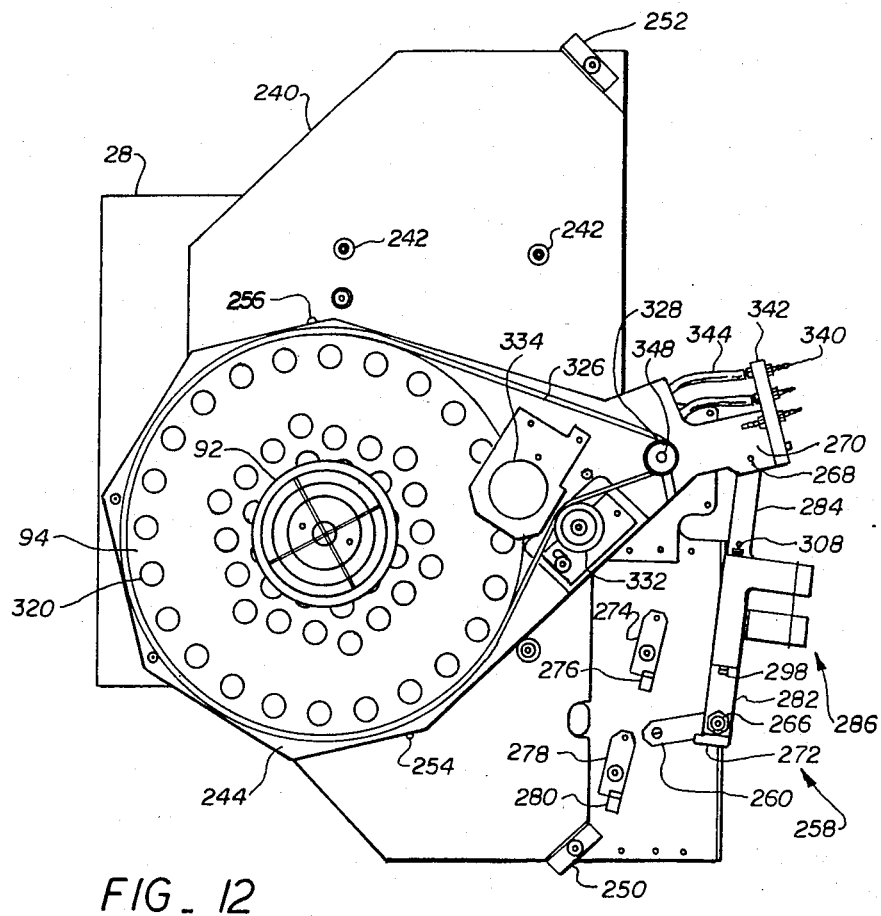
FIG. 12 is a top view of the X-Y stage (28) and shows the turntable (94), vacuum chuck (92), and the flipper drive assembly (258)
Figure 13:
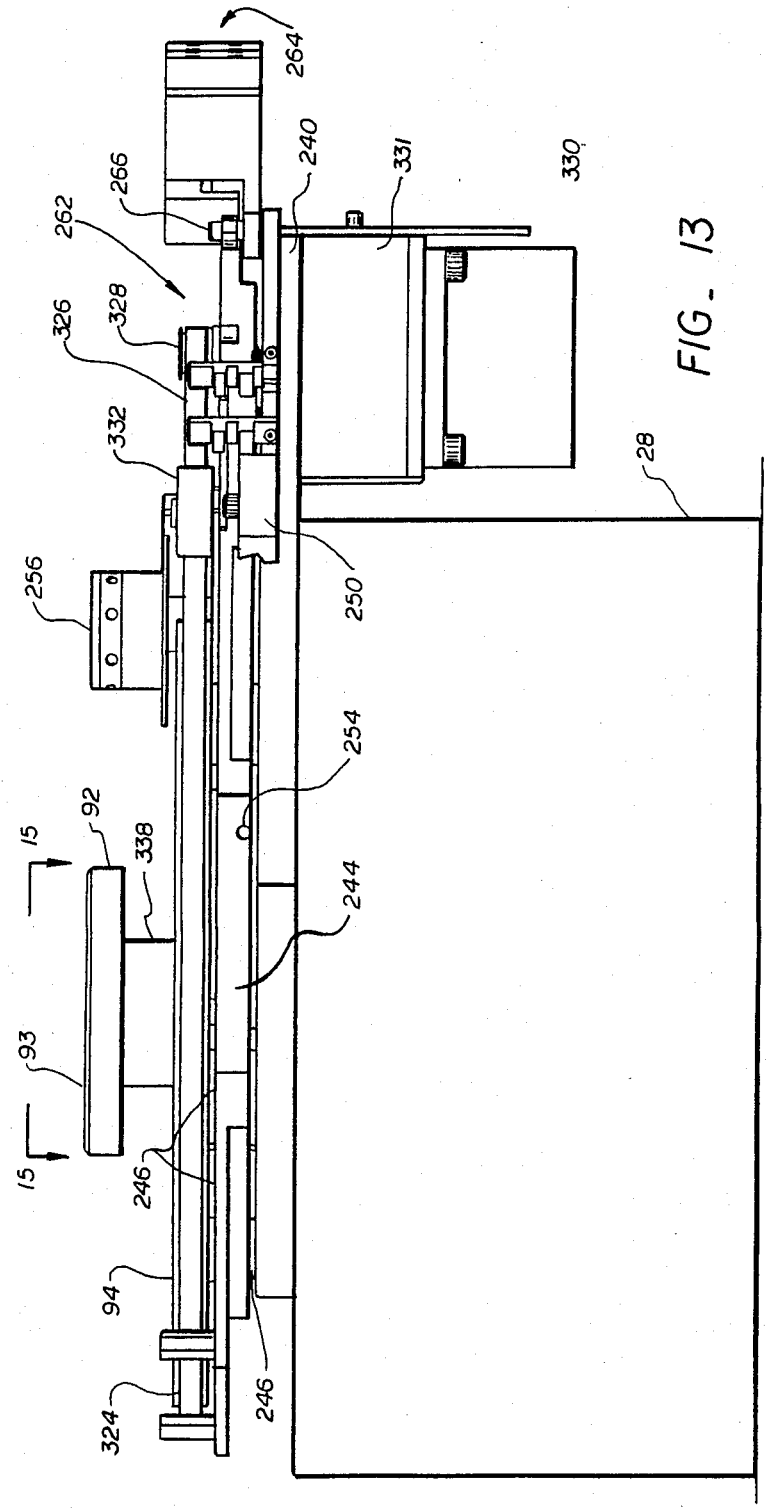
FIG. 13 is an elevation view of the X-Y stage (28), turntable (94), vacuum chuck (92) and the flipper drive assembly (258) shown in FIG. 12.

In FIG. 12, the macro-micro transport arm 244 is seen to be substantially centrally located with respect to the right side stop 250 and the left side stop 252 each of which are securely fastened to the base plate 240. These are hard stops and fixed, hardened ball-shaped bumpers 254 and 256 are positioned on transport arm 244 so as to engage, respectively, stops 250 and 252, depending upon the optical axis to which the mechanism is driven. The transport arm 244 is preloaded against these hard stops which are provided at each end of its travel. The transport arm 244 is moved over its travel range by a motor driven crank arm 260 connected to it by a spring-loaded link 264, with the crank and link forming a straight line at each end of the travel.

The macro-micro transport arm 244 is driven by a flipper type mechanism 258 which consists of crank 260 that is driven at one end thereof by a double-reduction belt contained in housing 261. The double-reduction belt drive is, in turn, driven by stepper motor 330. The other end of the crank arm 260 is connected by means of an eccentric pin 266 to leg 288 of spring-loaded drive link 264. The other leg 284 of the spring-loaded drive link is pivotally attached by pin 268 to the macro-micro transport arm 244 by means of an extension member 270 (drive arm) which is directly attached to the transfer arm 244. Thus, the turning of stepper motor 330 causes the crank arm 260 to rotate, and by means of spring-loaded drive link 264, the macro-micro transport arm 244 is pivoted about pivot 248. Once stepper motor 330 is enabled it will continue to move drive link 264 and, thus, transport arm 244 until sensor flag 272, which is attached to the proximal end of the drive leg 282, intersects a limit sensor, either 276 or 280, depending upon the direction of travel. Limit sensors 276 and 280 are positioned so as to be adjacent limit stops 274 and 278, respectively. These limit stops provide a back-up to insure that the drive mechanism does not attempt to drive the transport arm past the stops 250 or 252 attached to the base plate 240. At the same time, the spring-loaded drive link 264 is designed to insure that the transport arm 244 is forceably held against either stop 250 or stop 252.

The transport arm 244 must be moved so that it is always positioned and spring loaded against one of the hard stops. This is done to obtain a repeatable preload of the transport arm 244 against either stop 250 or stop 252. In order to accomplish such a result, it is necessary that the drive motor 330 drives crank arm 260 from one limit stop to the other. To obtain the desired result, a special drive link has been developed, and the drive link is shown in FIGS. 14 and 14A.

Figure 14:
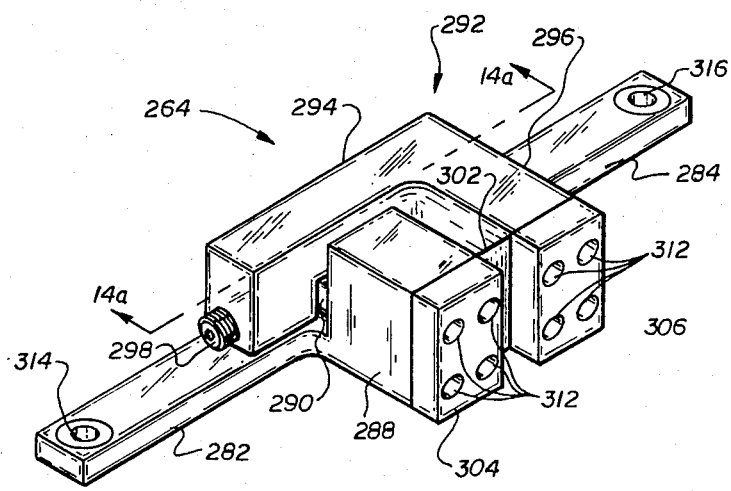
FIG. 14 is an isometric view of spring-loaded drive link (264)
Figure 14A:
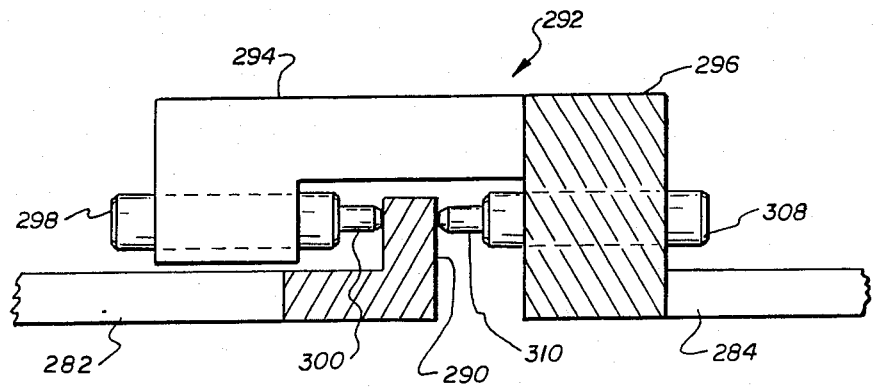
FIG. 14A is a partially broken section view along the line 14A—14A of FIG. 14.
Figure 15:
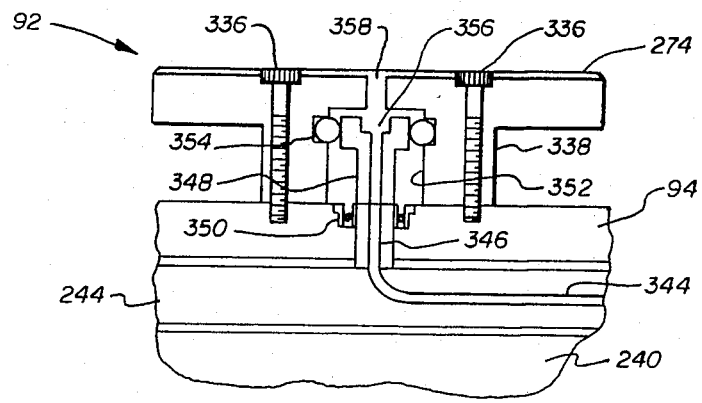
FIG. 15 is a section view of the vacuum chuck (92) and a broken view of turntable (94) and illustrates how the vacuum chuck is mounted and how a vacuum is applied to hold the wafer in place.

FIG. 14 is an isometric view of the spring-loaded drive link 264 and FIG. 14A is a sectional view illustrating the manner in which the mechanical interconnection is provided so as to permit the shortening of the drive arm link while maintaining a constant pressure against the transport arm to hold it hard up against a stop. It should also be noted that the structure is such that the links 282 and 284 are maintained in axial alignment at all times.

Referring now to FIGS. 14 and 14A, it may be seen that link 282 has a spring-stop 290 at the distal end thereof. Formed at the distal end adjacent to the the spring stop 290 is a flexure mounting block 288 which is at right angles to the axial length of leg 282. Leg 284 has an "L" shaped block 292 which includes axially aligned leg 294 and flexure aligned leg 296, the latter being parallel to the block 288. As may be seen in FIG. 14A, axial leg 294 has a cut out which provides space for the spring-stop 290 and movement thereof between the spring contacts 300 and 310 of the Vlier spring plungers 298 and 308, respectively. To prevent excessive axial misalignment of the legs 282 and 284, a flexure member 302 is attached to the end of blocks 288 and 296 by means of flexure retaining blocks 304 and 306, respectively, which are secured by mounting screws 312. An aperture 314 in the proximate end of leg 282 is adapted to accept eccentric pin 266, and the aperture 316 at the proximal end of leg 284 is adapted to accept pivot pin 268. Thus, the spring-loaded drive link 264 is connected between the crank drive arm 260 and the transfer drive arm 270.

While the macro-micro transport arm 244 positions the wafer, which is located on the vacuum chuck 92, in either the macro or micro optical inspection station location, complete alignment of the wafer for inspection purposes may require the rotation of the wafer. For this reason, a turntable 94 is provided. The turntable 94 rest solidly on stage 28 during a test. Prior to rotary movement an air solenoid is operated and the macro-micro transport arm 244 is then supported on air bearings 246 to facilitate rotation. In order to minimize the weight of the stage assembly, a plurality of apertures are formed in the surface of turntable 94. One such aperture is shown as 320 in FIG. 12. The edge of the turntable 94 is crowned in order to keep the drive belt 326 centered on the edge of the turntable. A toothed belt drive pulley 328 is turned by a belt drive motor (not shown) and the pulley and drive motor axis of rotation are positioned at the pivot point of the macro-micro transport arm 244 and is identified as pivot 248. An idler pulley 332 is employed for adjustment of the belt drive tension.

While the use of calibration or alignment wafer is the preferred method, a calibration wafer as the target may also be used to initially align the inspector. A calibration target 334 is shown and is located on the transfer arm 244. The target is employed to effect precise camera and optics calibration prior to inspection. Because the position of the wafer is determined from the camera image before and after each move, the rotational repeatability of the stage need only be sufficient for a single rotation. Long term drift is repeated rotations is unimportant. Since a stepper motor is used for rotation, precise single moves may be made by moving a specified number of steps.

Vacuum chuck 92 is centered on turntable 94 and is securely attached thereto by means of mounting bolts 336 that pass through the top surface 93 of the vacuum chuck through the sides of the recessed cylindrical base 338 and are secured in the turntable 94. In order to supply vacuum to the chuck top surface, a vacuum line (not shown) is attached to chuck vacuum inlet connector 340 which is attached to the connector assembly 342 and is connected to the vacuum line 344 which passes between the transfer arm 244 and the turntable 94 and is connected to the vacuum feed line 346 located in stand pipe 348. Stand pipe 348 is connected to the transfer arm 244 and is not rotatable. Bearings 350 are provided in turn table 94, thus allowing rotation of the turntable as the stand pipe 348 remains stationary. The stand pipe 348 is a shoulder screw which passes through the central aperture 342 and turntable 94. The upper end of pipe 348 terminates below the inside of the top surface of the chuck recess 358. The bottom end of pipe 348 sits on the top surface of macro-micro transport arm 244. Vacuum is drawn through the recess 358 and O ring 354, which is seated in recess 352, provide the necessary sealing against the loss of a vacuum at port 358.

Macro Inspection

The wafer accepted from one of the input cassettes and transferred via wafer arm 90 to the vacuum chuck 92 is initially in the macro inspection station position. The wafer 16 is loaded onto chuck 92 without concern for orientation or precise alignment. Prior to the inspection, the wafer edge and flat are found. The images picked up in macro view are first used to effect correct rotation and positioning of the wafer pattern. The macro inspection employs three different angles of illumination as well as three different levels of magnification to inspect for topological and patterning defects. The full wafer is viewed initially (up to 150 mm in diameter). This requires the lowest magnification 1/16X which gives the largest field of view. Also, the illumination is such as to give appropriate lighting to the full surface under test. The three angles of ilumination are obtained by a vertical array of three ring lamps that are arranged to generate different angles of illumination, from near field to dark field. The range is approximately from 10 degrees to 85 degrees, with different lamps being used to highlight different types of wafer defect, i.e., toplogical or patterning defects. The lamps may be switched on and off under computer control. By viewing the wafer, the flat is first found and the wafer rotated to the approximately correct orientation. A second view of the pattern on the wafer is processed in the computer to determine pattern orthogonality (which may be displaced a few degrees from flat) and a more exact rotation of the wafer performed. A third view of the entire wafer is then used to align to a reference feature selected in X-Y by the user. The reference may be either a test die or the perimeter of a step array. Test areas can then be automatically positioned and inspected in the macro mode. At the end of the macro tests, the computer chooses an area at the highest macro magnification, ¼X, which is unique in its field of view and small enough to be found again in the largest macro objective field. It has to be unique within the area of uncertainty in positioning due to the sum of the errors in macro position and hand-off when seen in the micro field. It must be small enough so that it still resides completely within the micro field allowing for these errors.

The macro inspection requires the sequential use of the three different macro lenses, which means that each one must be separately moved into the optical path. The ¼X lens 116 is positioned to be directly in front of the macro mirror 30 when it is in use but is shifted out of the optical path when not in use. This is also true for macro lenses 118 and 120 although they are positioned adjacent the camera 38. The drive system must be precise and should take a minimum of space.

Figure 17:
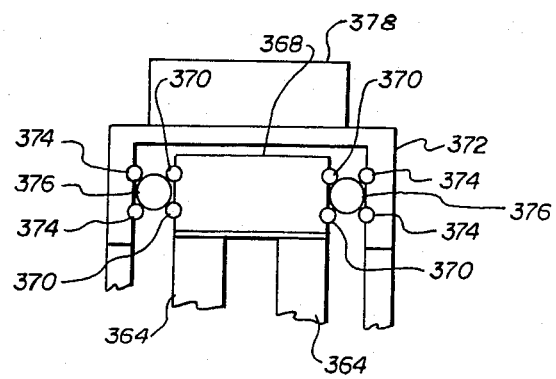
FIG. 17 is an end view along the line 17—17 of FIG. 16 illustrating how slider (372) is slideably attached to guide rail (368)

The preferred technique by which the macro lenses are moved is shown in FIGS. 16 and 17. Referring to the figures, it may be seen that a horizontal guide rail 368 is attached to vertical members 364 that are secured to the top surface of the upper aluminum casting 110 by screws 366. A slider 372 is secured to the top surface of the guide rail 368 by means of rods 370 and 374 which hold the balls 376 in position so as to provide an easy and accurate sliding motion. A drive arm 308 is pivotally attached to slider 372 via downwardly extending member 381 by means of a pivot pin 382. A wall 385 is formed in the space between the vertical members 364 and between the horizontal guide rail 368 and the top surface of casting 110. A stop member 388 is mounted on wall 385 and is positioned to intercept the stop screws 389 and 393 when the slider 372 is in either of its two assigned positions. Stop screws 389 and 393 are installed, respectively, in the lower ends of member 381 and 383. Adjustment is effected by lock nuts 391 and 395 which are adjusted so that the slider is stopped in the asigned position at each end of its travel. Note that drive arm 308 includes a flexible member 384 which includes expansion-compression sections 386 and 390 that allow slider 372 to be spring loaded against the stop in either direction of travel. In one direction the slider is driven until the screw is hard against stop 388. In the other direction, the slider is is driven until screw is against the other side of stop 388. As may be seen, the member 384 drops down to allow slider 372 to move to its other position. Thus, allowing member 383 to pass clear. It should be noted that there is a pad 372 that may contact the upper side of drive arm 380, and may do so on either side of the pressure absorbing member 384. Thus, the lens will always be accurately positioned, because the slider will be driven hard against the stop 388. The drive end of the drive arm 380 is connected to an eccentric arm 392 by means of pivot 394, and it is noted that the other end of eccentric arm 392 is pivotally attached at pivot 398 to spur gear 396 which engages with pinion gear 400 that is driven by stepper motor 402. The drive assembly for positioning a macro lens, the pentaprism or the moveable mirror is selected and is enabled by signals from controller 52. The sinusoidal motion of the crank provides gentle but accurate positioning at the stops while providing rapid movement in the center of travel. This is accomplished by each of the crank arm drive mechanisms.

In addition to the X-Y stage 28, on which the turntable 94 and chuck 92 are supported, the macro inspection station includes the wafer 16 and three ring lamps 20, 20A and 20B, which are selectively illuminated to provide the proper illumination for macro inspections. The reflected light passes upward toward a fixed macro mirror 30 where its direction is changed from vertical to horizontal and the light passes through one of the three macro lenses, 116, 118 or 120. Note that lens 116 which in the preferred embodiment is a ½ X lens is positioned so that it may be placed directly in front of the fixed macro mirror 30. Because the horizontal light direction from mirror 30 is at right angles to the input of camera 38, a moveable macro mirror 114 is positioned to intercept the light from macro mirror 30 so as to redirect it in the horizontal plane to the input of camera 38. In the path between the moveable macro mirror 114 and the camera 38, either the ⅛ lens 118 or the 1/16 X lens 120 may be inserted during the macro inspection process.

Following macro inspection, stepper motor 262 will be enabled by movement controller 52; and motor 262 will move crank arm 260, which, in turn, will move drive link 264 and cause the macro-micro transfer arm 244 to rotate about pivot 248. This moves the wafer from the macro inspection station to the micro inspection station and the X-Y stage will than be moved by drive motors 100 and 102 so as to repeatably position the wafer in the micro inspection station location. The system computer is programmed to provide for coarse adjustment of the wafer position during handoff. Fine adjustment is achieved by correlation of the images with reference images which were automatically selected as being unique in the macro and micro field of view. The same image at different magnifications is used. It should be noted that the turntable 94 is rotated as the X-Y stage 28 is "flipped" from the macro to the micro inspection station. This is done to correct for the rotation of the wafer due to the "flipping" movement and image rotation produced by macro and micro imaging systems. As noted hereinabove, image correlation is used to provide fine rotation adjustment and is accomplished by storing an image at one end of the wafer; moving over one die and finding the same image and correcting for misalignment. The stage is then moved a distance equal to an integral number of die near the other side of the wafer and final rotational adjustment is then made.

A number of the elements involved in the micro inspection are illustrated in FIGS. 4-7. At the time the wafer is being moved from the macro to the micro inspection station position, the moveable mirror 114 is moved out of the optical path and pentaprism 122 is moved into the optical path associated with the micro inspection station 32. The micro inspection system is built around a turret 608 and an imaging lens housing 425 of a Leitz Ergolux microscope. The turret 608 is placed on a special stepper motor driver mount which allows vertical motion of the turret to a resolution of $2 \times 10^{-6}$ inch to focus the microscope. A second stepper motor is used to automatically rotate the turret from one objective lens position to another with a handoff precision between objectives and with a repeatability of one micron. There are five objective lenses on the turret in the preferred embodiment. A discussion in detail of the vertical and rotational motion of the turret will be provided later.

Macro-Micro Optics

Figure 18:
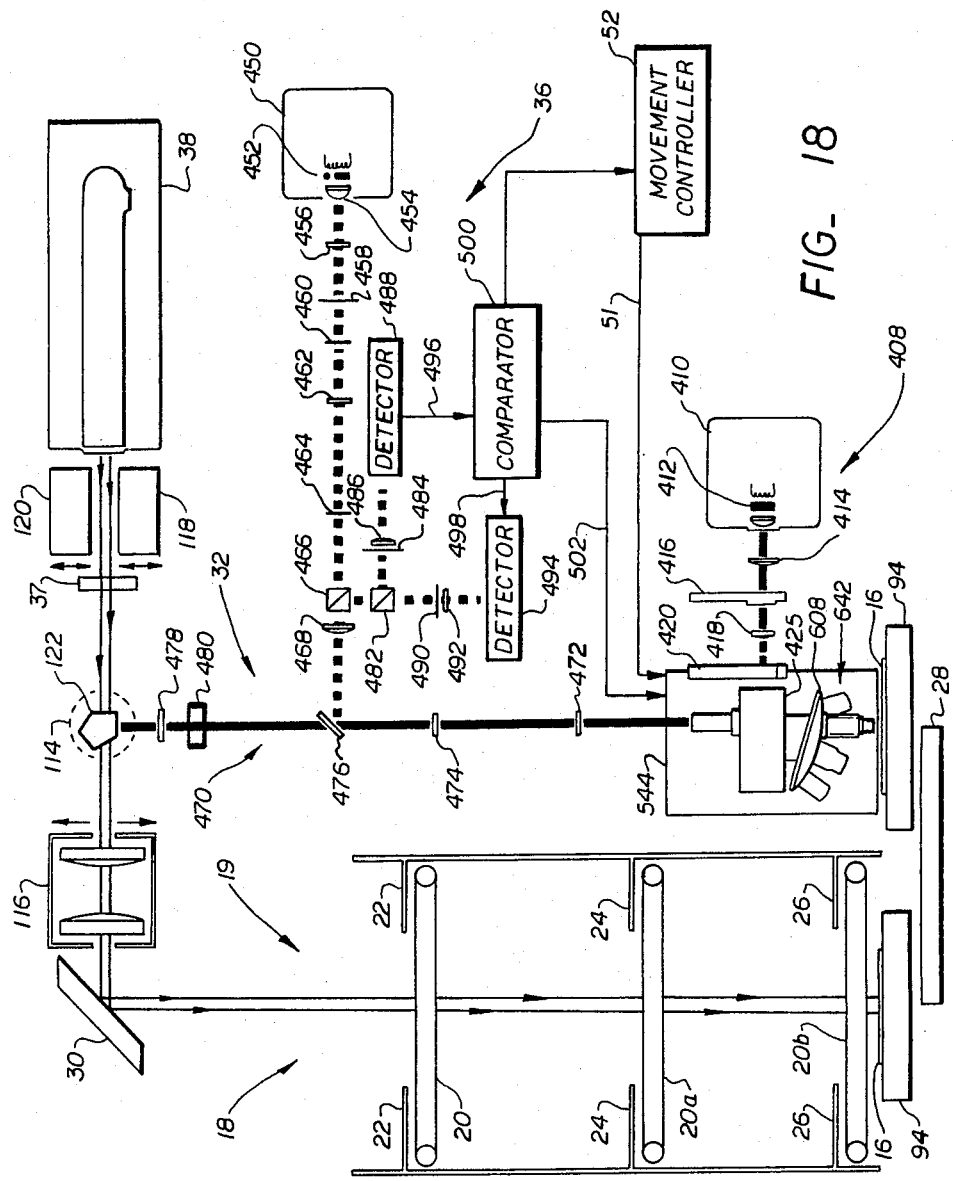
FIG. 18 is a schematic diagram which illustrates the basic optical elements and their interrelationships.

The overall optical arrangement for the macro and micro inspection stations is illustrated schematically in FIG. 18. For the macro inspection station 16, it may be seen that three ring lamps 20, 20A and 20B are vertically spaced one above the other, with each being symmetrically disposed concentrically about the macro optical path 19. The light shields 22, 24 and 26 are circular and positioned above each of the lamps to prevent direct light from the lamps being transmitted vertically upward. It is to be noted that the inwardly extending radial length of each shield increases for the higher positioned shields. The light from ring lamps 20, 20A and 20B illuminate the wafer under test 16 and the reflected light is transmitted to mirror 30 and is then directed to and passed through one of the macro lenses 116, 118 or 120, and moveable mirror 114. Note that mirror 114 appears in the path before either lens 118 or 120. A shutter 37 controls the light images that may be applied to the image input of the camera 38. When the macro-micro transfer arm 244 repositions the wafer 16 into the micro optical axis on X-Y stage 28, the moveable mirror 114 is moved out of the path and the pentapenta prism 122 is moved into position so that light from the micro optical path 470 is redirected via prism 122 to the image input of the camera 38. The images then are obtained using one of the five objective lenses 642 which are mounted on the lens turret assembly 608. Only one of the lenses is positioned so as to view the pattern on the wafer at one time and, as will be explained later, the camera 38 is not enabled to pick up the image prior to the time that the autofocus mechanism automatically insures that the image is in focus. The manner in which this is done will be discussed in more detail hereinafter.

Figure 19:
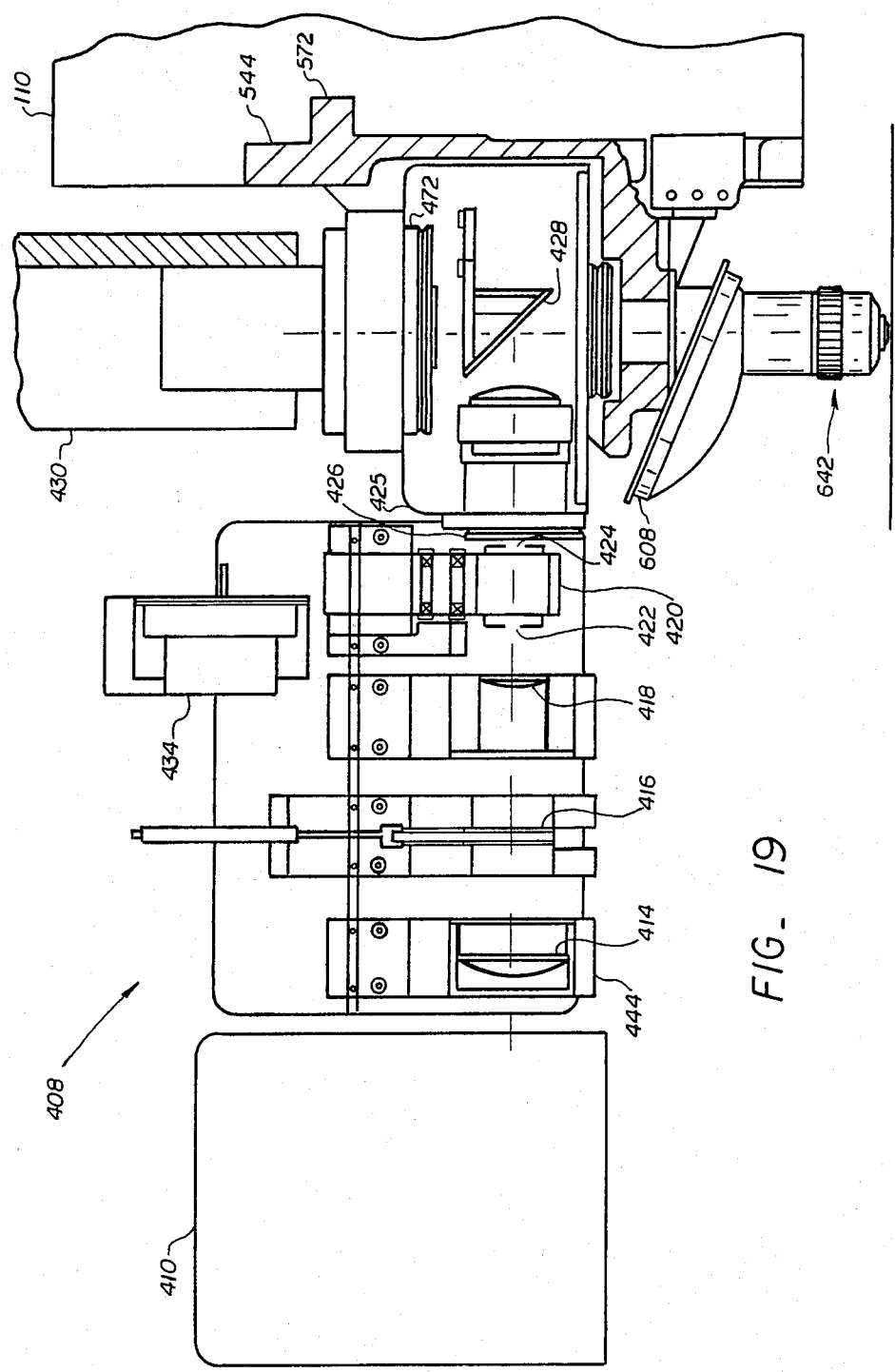
FIG. 19 is an elevation view of some of the micro optical elements and illustrates, in particular, the micro illuminator (408), imaging lens housing (425) and microscope objective lens (642)

In order to provide the appropriate illumination for the image system of the micro inspector, a main illuminator assembly 408 is provided as shown in FIGS. 18 and 19. In a preferred embodiment of the invention, illumination is provided by a modified light illuminator such as is standard on the Ergolux. Referring now to FIGS. 18 and 19, the illuminator assembly 408 for the micro inspection station includes an illuminator housing 410 which includes a lamp 412. The light from lamp 412 is passed through a central aperture to a frosted focusing lens 414. Next, the focused light passes through one light filter of a filter wheel 416 that is mechanically adjustable. A 400 to 550 nanometer filter is used for most micro tests during an inspection. A narrow band filter is employed for line width measurements. A black and white camera is used principally because it has superior resolution as compared with a color camera. The filtered light then passes through a focusing lens 418 to an aperture and pupil stop assembly 420. The manner in which elements such as lenses 414 and 418 are held in position is illustrated in FIG. 21. Referring to FIG. 21 it is seen that a lens 446 is seated in lens holder 444 and is maintained in correct alignment by vlier screw 448.

As it is known, small apertures and narrow band light are needed to illuminate fields where maximum modulation or patterns definition is required, e.g., in line width measurements. Of course, this reduces the incident energy and thus increases the time required to obtain an image with an acceptable signal to noise ratio. Where such a critical measurement is not being made, the incident energy of the light can be greater and the image pickup time reduced. It is also necessary to change the illumination aperture for darkfield measurements.

The light from focusing lens 418 passes through pupil aperture 422 and fixed field stop 424 to the imaging lens assembly 425. The light is first controlled by a dark field control element 426 which may be adjusted to provide a darkfield or brightfield (see FIG. 19A). The bright or dark field light then passes through the annular lens 426 and then strikes the illuminator mirror 428. The partially silvered illuminator mirror 428 (see FIG. 19B) is positioned to reflect the light downward through the objective lens to the surface of the wafer and allows the reflected image to pass up through the micro optical path 470.

The elements in the micro optical path 470 are mounted in the optical rail 430, partially shown in FIG. 19. The optical rail 430 is mounted to the floating aluminum chassis 110.

Three aperture/pupil stop combinations are automatically provided, one for brightfield (5X-50X), one for darkfield, and one for 100X for line width measurements. Referring now to FIG. 20, it may be seen how the filter 416 or pupil stop and aperture assembly 420 may be automatically adjusted to obtain the correct color filter or aperture pupil stop combination. A stepper motor 443 is mounted to the micro illuminator assembly 408 by means of mounting bracket 436. Under control of movement controller 52, stepper motor 443 turns drive shaft 437 which, in turn, causes pulley 438 to rotate. Drive belt 440 transfers the drive motion, e.g., to aperture/pupil stop 420. Means are alo provided to accurately center the stop 420 so as to produce symmetrical images for line width measurement. The illuminator also contains the filter wheel which is used to provide different illumination wavelengths.

Above the turret 608, mounted in the optical rail 430, is the Leitz imaging lens assembly 425. The imaging lens assembly takes collimated light reflected from the wafer through the objective lens and forms an image at the field lens 472. The images at the field lens are relayed to the camera tube of the TV camera 38 via 100 mm focal length collimating lens 474, 200 mm focal length imaging lens 478, filter 480, and the pentaprism 122. By use of the 100 mm lens 474 and 200 mm lens 478 in combination in the optical path, the images at the field lens are magnified two times in passing through this portion of the optical path. Filter 480 has been added to further attenuate the red light used in the autofocus (automatic focusing system).

As noted hereinabove, the light images for the camera 38 are controlled by a shutter 37, and the shutter is closed so that during the time the wafer is being positioned no light reaches the camera. Once the stage 28 is steady and the objective focussed, the shutter is opened so that the image is presented to the input of the camera. The camera beam current is controlled to allow integration of the light received during the entire time the shutter is open. Once the shutter is closed, the signal is read from the camera. The stage can move in parallel with this operation. Thus, the image is converted into an electrical representation on the face of the camera tube. The time during which the shutter is opened is programmable. The system computer program is used to automatically adjust this time so that sufficient light can fall on the tube to provide an adequate signal to noise ratio. It is only after the shutter is closed again that the controller 52 permits the electronics to provide current to scan the tube face of camera 38 and read out the stored image. During the first complete scan (raster) the image is read into high speed memory. Scanning is allowed to continue for several more complete rasters to remove the residual image after the shutter is again closed. In this way, several purposes are accomplished. The light can be integrated for a sufficient time to provide good signal to noise ratios even for low reflecting images or where narrow illumination apertures or bandwidth are employed. Also, the residual image can be effectively removed and does not get added to the wanted image. Further, the image can be read out in parallel with the next movement of the stage thereby increasing the testing speed.

Autofocus Electro-optics

Figure 22:
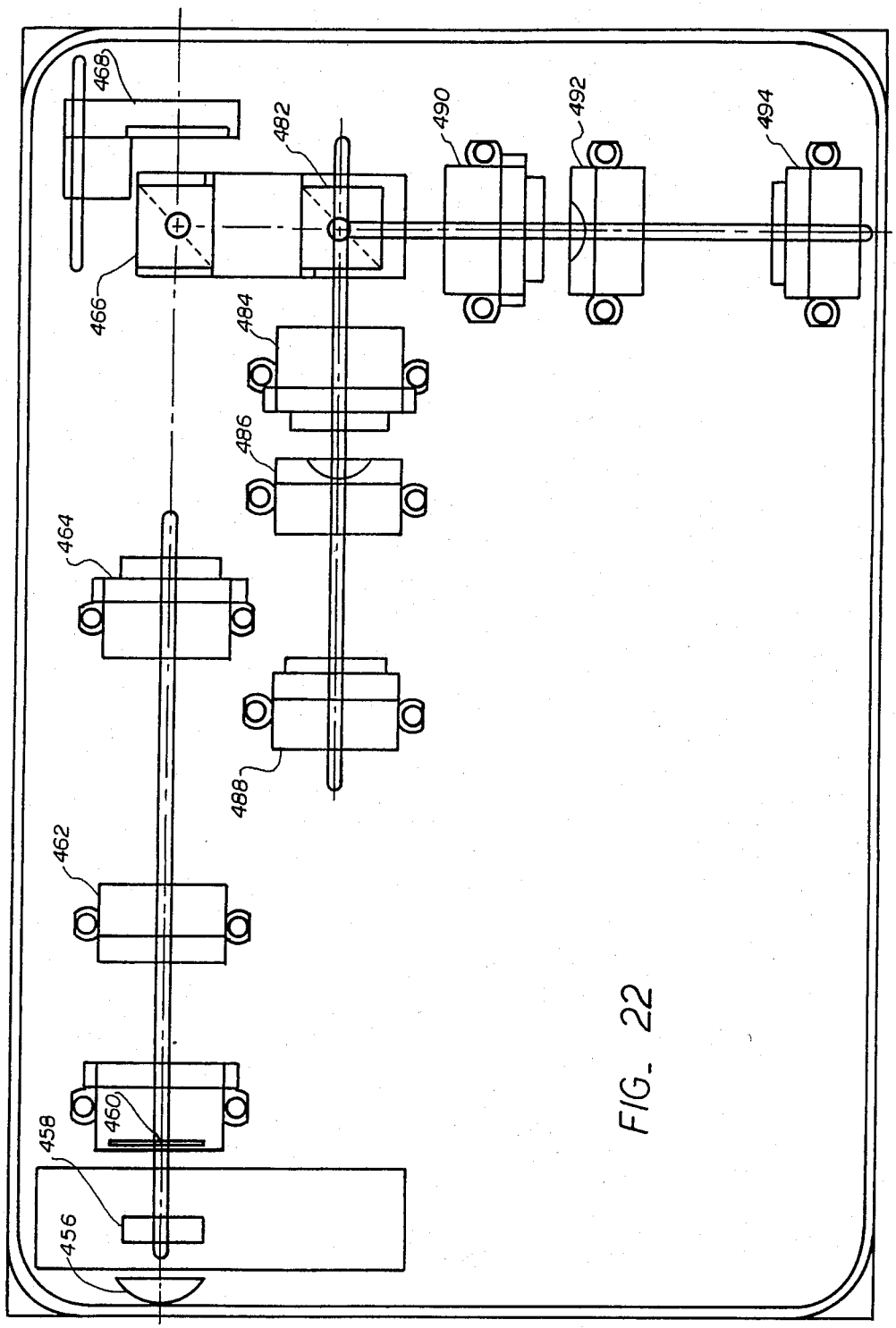
FIG. 22 is a block diagram illustrating the physical arrangement of the elements of the autofocus assembly.

An automatic focusing system for the objective lenses is provided, and comprises an electrical drive circuit, an autofocus optical system which provides a feedback signal to control the drive circuit and a flexure mounted turret assembly. Operation of the autofocus optical system may be understood by reference to FIGS. 18, 22-27. Referring to FIGS. 18 and 22, the general configuration of a preferred embodiment of an autofocus assembly may be seen. A lamp housing 450 includes a quartz halogen lamp 452 which is the light source for the autofocus system. The light is passed through collector lens 454 and condenser lens 456, and through a red filter 458, which passes light having wavelengths longer than 600 nanometers. The use of a red filter is to control the frequency of the light used and, thereby, permit selection of the autofocus optical signal from the optical signal used for the the micro inspection optical path 470.

The light is then applied to a pupil stop 460 which contains an eccentric pin hole aperture which offsets the image location. This offset is illustrated pictorially in FIG. 23. The image of the pupil stop on the objective back aperture is ½ the diameter of the smallest objective back aperture which is 100 X. The position of the pupil is adjusted so that its image is just tangent to the 100 X back aperture as shown in FIG. 23. This causes the returning image of the projection reticle, a schematic example is shown in FIG. 27, to move laterally as the microscope objective is moved up and down, i.e., in and out of focus. Thus, when the microscope is in focus the returning image of the projection reticle will fall on the reticle so that the image of the reticle pattern is coincident with the reticle pattern itself. As the objective lens is moved out of focus, this image will translate laterally relative to the projection reticle.

After passing through the pupil stop 460, the lamp light from lamp 452 passes through the pupil lens 462 (focal length 50 mm) and becomes collimated. It then passes through a projection reticle 464, located 100 mm from the pupil lens. The projection recticle 464 lies at the focal point of the 100 mm focal length autofocus imaging lens 468 which collimates the light coming from the reticle. The autofocus light, containing only wavelengths above 600 nm, then enters the micro inspection system optical path 470 via a dichroic mirror 476 which reflects the light having a wavelength longer than the 600 nm red light and transmits light with shorter wavelengths. Since the light from the reticle is collimated when it enters the optical path 470 in the collimated space between the 100 mm microscope collimating lens 474 and the 200 mm microscope imaging lens 478, the reticle image is focused on the wafer when the microscope is in focus.

The 100 mm autofocus imaging lens 468 is located with the image of the back aperture of the objective at its focal point. This image is than collimated between the 100 mm imaging lens and the 50 mm pupil lens 462 and brought to a focus at the pupil stop 460 located at the focal point of the 50 mm pupil lens 462. Thus, the pupil stop 460 is imaged on the back aperture of the microscope objective and vice versa.

The image of the pupil stop on the objective back aperture is one-half the diameter of the smallest objective back aperture (100X). The position of the pupil is adjusted until its image is just tangent to the 100X back aperture, with it centered vertically above the optical axis. It is not necessary that the aperture be vertically above center, but it is necessary that it be off axis, i.e., in a position to control the direction of rotation of the return image. Thus, proper positioning causes the returning image of the projection reticle to move laterally as the microscrope moves up and down, in and out of focus. The movement of the image of the projection reticle with respect to the projection reticle will depend upon how the image is affected by elements in the optical path. For example, the movement may be vertical with respect to the right mask and horizontal with respect to the left mask. The direction of movement will be such as to increase the occulsion for one while decreasing the occulsion of the other as the objective lens is moved from a position of focus. However, in FIG. 24 only vertical movement is shown, it being understood that this is to illustrate the effect of the translation and is not a limitation. This image movement is such that the right and left masks provide equal light outputs when the lens is in focus. The reflected reticle image is transferred from the micro inspection optical path 470 to the autofocus path by dichroic mirror 476. Fifty-percent of the autofocus red light returning from the wafer is split out of the main beam by beam splitter 466 stationed between the autofocus imaging lens 468 and the projection reticle 464. This splitoff light is then split into two equal beams by a second fifty-percent beam splitter 482 to left and right light sensing circuits.

In the left light sensing circuit, a mask 484 and detector lens 486 provide variable light input to a photodetector 488. The right sensing circuit comprises mask 490 and detector lens 492 which provides a variable light input to a photodetector 494. The detector lenses 486 and 492 each focus the collimated pupil light from the 100 mm lens 468, respectively, on photo defectors 488 and 494, i.e., the pupil is actually imaged onto the surface of the associated detector. Detectors 488 and 494 each separately convert the separate light inputs into electrical signals representative of the light input and these electrical signals are applied to inputs of comparator 500 via paths 496 and 498, respectively. The amplitude of the electrical signals applied to comparator 500 depends upon the amount of light passing through the right or left mask. By substracting the electrical signals, the electrical output signal will be zero when the objective lens is in focus, i.e. the electrical signals are equal. As the objective moves in the negative direction from focus, the reticle images both move down. When in focus, an equal portion of each returned image is occluded, in one image the top portion of the return image is occulded, in the other the bottom portion is occulded. The return masks may be adjusted to provide 30%, 50% or 90% occulsion. Only the 30% occulsion is illustraed in FIG. 24 to avoid confusion in the drawing. The electrical output for the different amounts of occulsion is illustrated in FIG. 25. It is to be understood that as images go out of focus, the light passing through one mask will increase while that passing through the other mask will decrease. The reverse situation occurs when the direction of motion of the objective changes from the direction of focus. The signal output from comparator 500 is essentially linear about zero, as shown in FIG. 26, and is applied to a stepper motor 576 which provides vertical drive through a lever system to the movable turret support member 544.

Because of the difference in focal length of the optical system at the different wavelengths used for the imaging and focusing tasks, the position of focus may be different. This can be partially corrected by positioning the optical components, however, because several different optical objectives are used with different color correction, electronic offset may be required to focus the image on the camera. This may be achieved by first focussing using the normal autofocus system described above and then offsetting the position of the objective to the required focus for the camera. This will be a fixed distance away from the normal focus. This can be achieved by counting pulses on an encoder connected to the mechanical drive as the mechanical system is essentially backlash and friction free. Such an encoder may be included, for example, with motor 576. An offset signal is stored in memory and is applied as a series of digital pulses to operate the encoder. Alternatively, this can be done by setting the necessary electrical offset in the autofocus system. In this latter case, the intensity of the returned signal changes depending upon the reflectivity of the wafer and the focus illumination intensity. The gain, G, of the system near focus is linear and can be measured by stepping (moving away from focus) a fixed distance, d, and measuring the voltage change v over the required target area on the wafer. Circuits for providing the motion and measurement are well known and, in a preferred embodiment, are effecuated by control and data storage 46, in conjunction with the auofocus system. This is based on the variation in the light returning from the wafer and is compensated for by using the sum of the reflected signals with the wafer in place minus the background readings with no wafer in place to normalize the difference signal. If the required offset to obtain best focus is X, the offset voltage Vo is given by Vo=X.v/d.

The autofocus system is capable of tracking focus while the stage 28 moves. However, during motion the focus is positioned to give zero offset. This is because the reflectivity of the wafer is changing, depending upon the geometry, and so the required offset voltage for best focus also changes. The null position remains a fixed distance from the wafer as the signal to both sensors changes at the same rate.

The autofocus system would work with a single hole or occlusion in the projection reticle (and a similar pair, i.e., hole and occlusion in the return path). The purpose of using multiple images is to avoid the defocus problem associated with an image positioned across an edge which has different reflectivity on either side. This would cause some defocussing in a stationary image. Ideally, these images should be randomly scattered across the reticles.

Referring now to FIGS. 22, 27–29, some of the physical characteristics of the electro optical circuit employed in the autofocus mechanism may be understood. The physical arrangement of the elements is shown in FIG. 22 and it is important to notice the eccentricity of the pin hole aperture 460, which is of critical importance to the autofocus optical analysis. Referring to FIG. 27, a typical optical module mount 510 is illustrated. The optical module 514 is shown holding the projection reticle 464 and the assembly includes a theta adjust lever 516. Referring to FIGS. 28 and 29, which are front and side elevation views of the adjustable mounting asembly 518, the manner in which the adjustable lens mounting assembly 518B is flexure attached to assembly 518 may be seen. A parallelogram flexure assembly comprises upper and lower X-axis flexure arms 521A and 521B on either side and Y-axis flexure arms 523A and 523B at the top and bottom. From the drawing, it is apparent that screw 520 provides an X axis adjustment and, screw 522 provides a Y axis adjustment for the optical module 514. The adjustable mounting assembly 518B also includes an aperture 524 which is threaded and includes a theta locking screw (not shown). Access to the locking screw is via an aperture (not threaded) through 518 which is aligned with aperture 524. When the theta locking screw is backed out, the rotational or theta adjustment of the image holder 514 can be obtained by moving the theta adjust lever 516. Once the theta adjustment is proper, the theta locking screw is than tightened and the imge holder is held in position. The attachable mounting assembly 518 rests on a guide member and the base 526 includes guide slots 530 to permit Z axis adjustment. The base is held in position by locking members 528.

Turret Adjust Assembly

Referring now to FIGS. 30–33, the manner in which the turret mounting assembly 540 provides the necessary vertical motion for focusing of an objective lens, and the manner in which the rotational movement of turret 608 is used to select the desired objective lens may be understood. The turret mounting assembly 540 includes a rigid part 542 which provides the fixed support for the non-moveable elements and those moveable elements which are used to provide the vertical motion for focusing and the rotational motions for objective lens selection. A moveable turret support portion 544 is attached to the rigid support part 542 by means of flexure assembly 546. A pair of flexure members 548 and 548A, each comprising a flat sheet of material which exhibits a certain degree of flexibility, provide the interconnection between the fixed and moveble parts of the turret assembly and guide the turret assembly along a nearly vertical path without allowing the objective lenses to tilt. The end portions of the flexure members 548 and 548A are attached by means of clamping plates 550 at the upper and lower ends of the turret assembly and to a corresponding portion of the rigid member back plate 542. Rigid member 542 is attached to aluminum casting 110 by suitable means (not shown). For the lower and upper flexure members, stiffening plates 554 and 556 are employed to sandwich the flexure members 548 and 548A so as to control the degree of flexure that may be readily obtained. It should be understood that the motion of the moveable turret support 544 is to be in the order of 0.015 inch. However, it is necessary to accomplish this motion without hysteresis or any frictional problems that may be associated with other types of drive systems. This is necessary because repeatability within about 0.05 micron is desired. By using the drive technique of this invention, the precision positioning desired is obtained.

As seen in the drawing, although similar stiffening plates 554 and 556 are employed with the flexure member 548 as are employed with 548A, an aperture is formed in the plates associated with flexure member 548 to accommodate support wire 570. The function of this wire will be discussed in more detail later.

As described hereinbelow, turret assembly 608 is mounted on a moveable turret support 544 that allows vertical motion under the control of a motor 576. In a preferred embodiment, a dc motor and an encoder are used to provide controlled drive. To obtain repeatability to within $2 \times 10^{-6}$ inches in the focus of the microscope, the turret support 544 is attached to the rigid member 542 of the inspection assembly by means of flexures. The weight of the assembly causes a downward force on the flexures which would force the turret support downward toward its lowest vertical position, and is augmented by a coil spring 573 which acts in tension to pull the support down. A position control lever lever arm 560 has a wire 570 attached thereto. The other end of the wire is attached to the moveable turret support 544 at the turret lift arm 572 by means of a clamp 574. The wire and lever arm act to pull turret support 544 up against its weight and the force of coil spring 573.

In one embodiment of the invention the position control lever arm is flex supported as shown in FIGS. 30, 31, 32 and 33. At the proximal end, the position control lever lever arm 560 is attached to a cantilever support arm 562 by means of a flexure member 564. Flexure member 564 is attached at one end to cantilever support arm 562 by upper clamping plate 566 and at the other end to position control lever arm 560 by means of lower clamping plate 568. The distal or drive end, of the position control lever arm 560, is driven by vertical position motor 576, which is mounted on horizontal support 578 that is attached to the back plate 542. The shaft 580 from motor 576 is attached to micrometer (or lead screw) 584 at the screw end 586 by means of a rigid coupling member 582. The micrometer frame (or lead screw nut) 588 is connected to drive member 590. Thus, as the motor 576 turns under control of the autofocus signal input, the precise position provided by the motor 576 is, in turn, used to drive a precise instrument so as to provide very small precise almost linear steps for positioning the lever arm 560. This position control lever arm 560 is driven by a flexure drive link 592 which is clamped at one end to the drive member 590 by means of clamping plate 596 and to the distal end of position control lever arm 560 by clamping plate 594. In order to insure that the vertical motion stays within acceptable limits, a limit flag 598 is attached to drive member 590. Lower and upper limit optical detectors 600 and 602, respectively, are positioned to intercept the flag 598 so as to stop the vertical motion when the upper or lower limit is reached.

In a preferred embodiment of the invention, the proximal end of position control lever arm 560A is supported by crossed flexures as illustrated in FIGS. 30A and 30B. A single vertical flexure 564A is used and is positioned intermediate two horizontal flexure 564B and 564C which are each about one-half the width of 564A. The upper clamping plate 566A is L shaped and is designed to accept a horizontal clamping plate 566B which clamps one end of each of the horizontal flexure 564B and 564C. The other end of each horizontal flexure is clamped to position control lever arm 560A by a horizontal clamping plate 566C. At the distal or drive end, a new pivot structure replaces the flexure drive link 592. As shown in FIG. 30A, the pivot structure is positioned between horizontal support 578 and the under side of the distal end of position control lever arm 560A. Horizontal support 578 is clamped to the nut that travels vertically on lead screw 586 as the lead screw is rotated. A bottom plate 593 includes a V-slot 595A which is aligned with V-slot 595B in floating plate 593B. A pair of balls one shown as 597A, are positioned in the aperture formed by V-slots 595A and 595B, and thus permits a small amount of "Y" direction travel. In line with the control lever 560A is a pair of V-slots, one in the upper surface of said floating plate 595B which is aligned with the V-slot in top plate 593C. A pair of balls 597B and 597C are positioned in this upper longitudinal V-slot and permit a small amount of travel in the "X" direction. The asembly is flexibly held together by four coil springs one adjacent each end of the two V-slot formed apertures. The top plate of this pivot structure is atached to the end of position control lever arm, and the movement force is then transmitted from the motor 576 (dc motor and encoder) to the turrent support structure 544 via support wire 570.

It will be understood that, by the use of the turret support flexure members, the cross flexure connection to the proximal end of position control lever arm 560, the use of the pivot structure at of the drive end and the drive wire 570, sidewise motion as well as other motions that might otherwise adversely effect the positioning during focus operation have been substantially eliminated. Further, the manner in which the flexure support members 548 are attached so as to support the moveable turret support 544 in relation to the fixed position 542 is such that the motions other than vertical are substantially prohibited. As a follow-up with the avoidance of any sidewise thrust, the position control lever 560 has an aperture 604 at the distal end which is designed to allow passage of the thimble part 606 of micrometer 584. In a preferred embodiment of the invention, the drive movement for the moveable turret support member 544 provided the following characteristics. The flexure and the wire attachment to the turret assembly 544, in combination with the lever arm arrangement, provided a ratio of 31:1; and the stepper motor had a lead screw with 40 threads to the inch. By the use of this flexure mounting arrangement and drive system, the focusing mechanism exhibited a negligible hysteresis and provided a resolution of $2 \times 10^{-6}$ inch.

Although in a preferred embodiment, a moveable lens assembly has been used in the autofocus system, it should be understood that other arrangements could be employed. For example, the lens position could be held fixed and the stage could be moved up or down to bring the wafer into focus.

Another problem associated with the automatic micro inspection techniques is the handoff between objective lenses. The inspection of a particular location within a die of the wafer requires that the objective lenses that are sequentially used to provide the different magnifications necessarily must be positioned to a repeatability of less than one micron from one objective to the next. While a precise drive system might provide the necessary handoff positioning from one objective lens to the next, a major problem with such a device is the slow speed at which it must operate in order to accomplish the desired result.

In the present invention, a standard turret 608 is modified to mount V-slots such as 612 and 614, which are made of a hardened material and can be adjusted in position to a precise location. One such V-slot is used for each objective lens, however, only two have been shown. The V-slots are positioned on the periphery of the turret 608 as shown and are designed to take a detent alignment ball 610. While the use of detents have been previously employed such use has involved the detent ball riding on the periphery of the device during rotation. In accordance with this invention, the detent ball is separated from the peripheral surface of the turret when the turret is in motion. In fact, the ball is removed from the V-slot prior to the time at which the turret drive stepper motor 644 is actuated. By so doing, the pressure of the detent ball 610 on the peripheral surface of turret 608 is removed, thus allowing the turret to move at a more rapid rate and at the same time the wear on both the turret and the ball is essentially eliminated. Detent ball 610 is bonded to detent lever arm 616 which is attached to the moveable turret support 544 via flexure 617 (see FIG. 33). Flexure 617 allows detent lever arm 616 to pivot about a vertical axis relative to moveable turret support 544. A centering spring 620 is positioned in retaining apertures 618 and 624, the latter being in the detent pressure arm 622. By this arrangement, lever arm 616 is under constant bias pressure to force detent alignment ball 610 against the periphery of the turret 608.

When it is desired to change the objective lens in a handoff arrangement, pressure is applied via the objective alignment wire 626 which pulls the lever arm 616 and consequently detent alignment ball 610 out of a V-slot, such as 614, and away from the periphery of the turret 608. This is accomplished in the following manner. Detent stepper motor 636 provides the drive to motor shaft 634 which is attached via coupling assembly 632 to the mounting screw 630. Mounting screw 630 secures the inner race of ball bearing 628 to assembly 632. In the coupling assembly 632, it is noted that the mounting scew 630 is offset from that of the centered motor shaft 634, thereby providing an eccentric drive. Wire 626 is attached to the outer race of bearing 628. Thus, by rotation of the motor shaft 634 under control of the stepper motor 636, tension may be applied to wire 626 whereby the lever arm 616 is pulled away from the periphery of turret 608. The motor rotates 180 degree to remove the detent ball 610 from V-slot 612. Alternatively, the wire 626 may be in a slack condition which allows the lever arm 616 to force detent alignment ball 610 against the periphery of the turret 608, and avoids affecting the preload of the detent ball 610 as the turret moves up and down to focus.

An eccentric detent flag 638 is attached to the coupling assembly 632 by means of mounting screw 630. When in position such as shown in FIG. 31, wire 626 would be slack allowing the detent ball 610 to rest in V-slot 614. Eccentric 638 is not in position to block optical detector 640 and the assembly is in a "ready" status. When an objective handoff is to be accomplished, the stepper motor 636 is actuated by movement controller 52 causing tension to be applied to wire 626 which forces lever arm 616 away from the periphery of the turret 608. At the same time, flag 638 moves to a position in which it blocks the light flow through the path of the optical detector 640 thereby stopping the stepper motor in a position under which wire 626 is in tension. The motor rotates 180 during this process. As will be explained in detail hereinbelow, the turret is then driven to the next objective lens position. At that time, stepper motor 636 is reactivated causing the tension on wire 626 to be released and moving eccentric 638 so that it no longer blocks the light to optical detector 640. When lever arm 616 comes toward the periphery of turret 408, detent alignment ball 610 strikes a V-slot, such as 612 forcing the turret 608 to move into a precisely aligned position.

The manner in which the turret 608 is driven from one objective position to the next in a hand-off situation may be understood by reference to FIG. 32 in conjunction with the following discussion. Once the detent alignment ball 610 has been withdrawn from the V-slot, stepper motor 644 is actuated and rotates shaft 646 which is coupled to a flexible coupling 650, the rotation being through an aperture 648 of the back plate 542. The motion is then transmitted via drive shaft 652 to a second flexible coupling 654 and thence via shaft 656 which passes through a plain bearing 658 in turret support 544 to a standard bevel drive gear 660 on the turret head or nose piece. The use of the two flexible couplings is to allow for freedom of movement of the moveable turret support member 544 with respect to the rigid support member 542. A flag 662 is attached to an alternate drive output of stepper motor 644 and the gear ratio is such that one full rotation of the stepper motor 644 drives the turret from one objective to the next adjacent objective lens. This is a good approximation and is done rapidly. The detent mechanism provides precise alignment.

Once stepper motor 644 is activated, it will continue to drive the turret until the flag 662 interrupts the light path of optical detector 664. At that time, the drive motion from the stepper motor will cease, the stepper motor 644 is deenergized. However, the detent stepper motor 636 will now be reactivated so as to release the tension on wire 626 and thus allow detent alignment ball 610 to drop into the associated V-slot on the periphery of the turret 608. Because stepper motor 644 is deenergized, the detent can move the turret drive as required to obtain exact positioning. By using this combination for the turret drive and alignment, the turret is allowed to run quickly between adjacent objective lenses. Following this, tension on wire 626 is released and bias or centering spring 620 drives the ball into the V-slot forcing the turret 608 into a precise alignment. This positions the objective lens in the field of view of the previous objective lens and repeats to within 1 micron in position each time. The exact position of each objected lens is adjusted to 2–5 micron, but the position is repeatable to within less than one micron. In an alternative embodiment, the V-slots are fixed and are capable only of accurate repeatability rather than absolute positioning accuracy. The same method of switching objectives is used as described above. However, accurate positioning is obtained by slight adjustment of the X-Y stage 28 based on positioning corrections stored in the computer.

To suppress mechanical resonance in the autofocus system, a damper mechanism has been provided. One embodiment of a damper mechanism is shown in FIG. 32. This comprises a well 668, a damper 670 and a damper support arm 672. The well 668 containing silicon fluid 674 is attached to the moveable turret support member 544. The damper support arm 672 is attached to the inner face of the rigid member 542. Because of the viscosity of the silicon fluid 674, resonances in the focus drive mechanism are suppressed. The damper also helps to decrease motion caused by the drive mechanism for the turret 608 and the other drive mechanism. This is necessary because line width is measured to within 1/20th of a micron and it is, of course, necessary to hold the vibrations to a magnitude which is less than this amount.

A preferred embodiment of a dampen mechanism is shown in FIG. 32A. A well 668A containing silicon fluid 674 is attached to the moveable turret support 544. The damper support arm 672 is attached to the inner face of the rigid member 542 as shown in the embodiment (see FIG. 32). In the bottom of the well 668A is a layer of closed cellfoam 669 which compresses under presure during damping action so as to accomodate displacement of the fluid. There are a plurality of spaced-apart thin plates 671 rising upwardly from the floor of well 668A to a level below the height of the sidewalls of said well. The damper 670A consists of a horizontal plate 673 which is attached to the support arm 672, and a plurality of downwardly extending thin plates 675 which are positioned between the upwardly extending plates 671. This combination provides exceptional damping action following turret movement which results from focus up and down motion or the shifting from one objective to another which includes the up and down as well as rotary motion effects.

Electronic Control System

Up to this point, the emphasis has been upon the mechanical features of the invention and the drive systems therefore. Although some references have been made to the electronic control system, many of the features of this system have not been clearly described. Referring now to FIG. 34, a generalized block diagram of the electronic control system may be seen. System controller 50A has as a main element a Motorola 68000 micro processor system which acts as the overall system controller. A video terminal 54 is a standard DEC VT-100 video terminal which includes a keyboard. The screen portion of the video terminal has been modified by the installation of a touch screen such as is provided by Carroll Touch Technology, and employs a series of vertical and horizontal infrared beams with associated detectors, as is well known, to provide a user interface directly with "buttons" of a menu displayed on the screen. A keyboard is provided to permit the user to select the tests to be run, the wafers in a lot to be inspected, and the tolerances which are to be permit- ted for a wafer to pass the inspection. A joy stick allows for manual movement of a wafer through the inspection process, and is commonly employed during the time at which the user's inspection procedure is entered. The inspection process is menu driven by the system computer 50; and, for a particular class of wafer, the user may select the tests to be run as well as the specific locations of the wafer that specific tests are to be performed. A camera 38 provides a real time image of the area of a wafer under inspection and this information is passed to the high speed image processor 56, which provides video digitization (including camera linearity and shading correction), image memory to store up to 8 full images, display formatting and control, video output look-up tables, and high speed address generation and image processing capability. When required, the image picked up by camera 38 is transferred via interface 56A and path 55 to video terminal 54. Data storage is provided by disk drive 46A which may be a hard disk drive and can be used to mass store the inspection procedure generated by the user for a class of wafers and may be used to store reference images.

In performing the inspection, the system controller 50A provides process control information to movement controller 52 so that the wafers may be moved through the inspection cycle, and be appropriately positioned as specified by the inspection procedure. The various activities that must be controlled have been divided into five different functional groupings as shown in FIG. 34.

The wafer load function 52C is shown in more detail in FIG. 35. As was stated hereinabove, a separate 8031 single chip microcomputer is employed for each motor. Each of the 8031 microcomputers, hereinafter "motor controllers", may also be used to control a plurality of solenoids for operating air and vacuum valves, air pistons and other devices. To load a wafer into the test system, movement controller 52 transmits the control information along path 51 which information is addressed to one of the motor controllers in the wafer load function 52C. A wafer could be selected from either cassette 12 or 14, these being considered the wafer input cassettes so the address must identify which cassette the wafer is to be selected from. If motor controller 52C1 is selected, the 8031 outputs a control signal to cassette 12 which loads a wafer on cassette track 58. Following the loading of the wafer on the track 58, motor controller 52C enables motor 60 to drive the wafer to the load track 64. Because a plurality of optical devices are employed, these are generally classified as optical sensors 65, it being understood that optical transmitters are positioned between the tracks of the wafer load track and the detectors are positioned in an optical rail 63 above the track. Interruption of the transmitted light from optical transmitter 62 signifies the presence of the wafer on wafer track 64 and motor 60 is stopped. Motor 72 is enabled to drive the wafer along wafer track 64 to a position on the load pad 68. An optical sensor signifies the presence of the wafer on load pad 68 and stops motor 72. When motor 72 is stopped, the actuator 127 is enabled driving load pad actuator arm 70 to its uppermost position. Upon completion of this movement, motor controller 52C4 enables a motor 90A which rotates wafer transfer arm 90 to a position that is below and beyond the position of the load pad actuator arm 70. When this mission has been accomplished and acknowledged, actuator 127 is enabled to bring the load pad down to its intermediate position. Next, motor controller 52C4 enables motor 90A to move wafer transfer arm 90 to a position adjacent load pad 68 so as to position the wafer in the recessed portion of the transfer arm 90. Next, the load pad actuator 127 is enabled by mnotor controller 52C3 to drive the load pad actuator arm 70 to its lowermost position and at the same time, the vacuum on load pad 68 is disabled and motor controller 52C2 causes a vacuum to be pulled in the recess of wafer transfer arm 90. Once the load pad arm 70 is clear, motor controller 52C4 enables wafer transfer arm motor 90A to move the selected wafer above vacuum chuck 92. Once in this position, motor 90A stops and wafer arm air piston 194 is actuated to drive the transfer arm 90 vertically downward to deposit the wafer on vacuum chuck 92. Simultaneously, the vacuum in transfer arm 90 is disabled, by controller 52C3. Once the wafer is deposited on the vacuum chuck 92, motor controller 52C4 enables the wafer motor 90A to drive the wafer transfer arm out of the stage area.

It should be understood that a number of the actions can occur simultaneously. For example, if the stage had previously been set for inspection in the micro optical axis, the macro-micro transport arm 244 would not be in a position to accept the wafer from wafer transfer arm 90. Thus, while the selected wafer is moving along the O-ring track a number of things could be occurring. First, the movement controller 52 would recognize that the stage assembly was positioned for micro inspection and as a first step would cause the motor controller 52F1 to enable motor 576 to drive the moveable turret support 544 to its upper position so that the objective lens is clear from the wafer. Then motor controller 52D4 activates a solenoid so that a air bearings 246 would be operational. Next, the movement controller 52 would enable motor controller 52D3 which in turn, would cause motor 330 to be energized and drive macro-micro transport arm 244 to the macro optical station position. While this is being carried on, the stage movement controllers 52D1 and 52D2 could be enabled to move the stage into alignment with the macro optical axis i.e., home position. When the transfer arm 90 deposits the wafer on vacuum chuck 92, movement controller 52 causes the microprocessor 8031 of motor controller 52D4 to pull a vacuum on vacuum line 344 which enables the chuck vacuum. This places the wafer in the approximate position for inspection, but more precise alignment and orientation is required. The manner in which this is accomplished will be described hereinafter.

Referring to FIG. 37, the optical control system may be seen. For alignment of the wafer, movement controller 52 provides a control signal via 51 to the optics controller 52E. First, motor controller 52E1 is enabled to insure that the moveable macro mirror 114 is driven into alignment with the macro optical path by motor 402 and the ring lamp 20A is turned on. The movement controller 52E2 is enabled to cause lens drive motor 402A to place the 1/16X lens in the optical path. Lamps 20 and 20B are turned off. The image is grabbed and the image processor 56 sums the pixels around the circumference to determine a brightness or darkness figure. Because of the differences in reflectivity in the area adjacent the edge in comparison with the patterned area, when the summed figure is a minimum value the wafer edge will have been detected and the wafer centered. Next, the orientation of the flat of the wafer is determined and movement controller 52 directs a control signal to motor controller 52D4 so as to enable air bearing 246 and turntable motor 262 which then rotates the vacuum chuck to bring the flat into the orientation selected by the user. This is a rough orientation. For more precise alignment, movement controller 52 directs control signals to motor controller 52D1 and 52D2 which, respectively, enable motors 100 and 102 so as to move the stage 28 so that it is positioned on a reference area such as a dropout (or the center of the wafer), and the reference is centered to the optical axis. At this same time, a control signal has been directed to optics controls 52E which enable motor 402A to move the lens 120 out of the optical path and enable motor 402B to move lense 118 into the optical path. The image, for example, the dropout reference, is grabbed and is compared with the reference image in the image processor. The image processor than sends, via the system controller, a control signal to movement controller 52 which is passed to motor controller 52D4 and motor drive 262 which causes an additional rotational movement (theta) to position the rotational orientation to within 0.05 degree. Again, an image is grabbed and the image processor compares the grabbed image with the reference to obtain the final X-Y coordinate movements which are to be directed to the stage controls and thus bring the wafer into precise alignment.

The macro inspection is effected by moving the stage to a center position in each of the four quadrants and repeating this with each of the three different lamps selected one at a time to provide illumination. A pair of images are selected from each of the quadrants for each test and the selected images are compared one with the other in the image processor to determine if they are alike or different. The tolerance level for the defects will have been set so as to avoid rejection of a wafer when any single defect is determined. This will be discussed in more detail hereinafter.

Once the macro inspection has been completed, a unique image is selected in the macro field of view prior to moving the wafer to the micro optical axis. In many applications, the centermost dropout is selected and the stage 28 is moved by X-Y motors so as to center the centermost dropout. The optical controls turn off lamps 20 and 20B and turn on lamp 20A and motor 402C drives ½X lens 116 into the macro optical path. When this has been accomplished, the image is grabbed by the image processor and held for comparison with an image that will selected following the transfer between macro and micro optical axis.

Before the stage controller causes the macro-micro transport arm to move the turntable and vacuum chuck into the micro optical station, it is necessary to insure that the objective lenses are positioned so as to not interfere with the movement. System controller 50A then causes movement controller 52 to send a series of control signals to the auto focus controler 52F. Motor controller 52F1 enables motor 576 and drives the moveable turret support 544 to its uppermost position. Motor controller 52F2 enables motor 636 and removes the detent 610 from a V-slot such as 612. Once the detent ball has been removed, motor controller 52F3 enables motor 644 and drives the turret 608 so as to position the lowest magnification lens in the optical path for viewing of the wafer. At the same time, a control signal has been transmitted to optical control 52E and enables motor controller 51E1 so as to move the moveable mirror 114 out of the optical path and move the pentaprism 122 into the micro optical path. Once the objective lenses have been properly positioned, the acknowledgement of the completion of the mission is transmitted to the movement controller 52 which then notifies the stage control 52D to effectuate the transmitted commands. The X-Y motors 100 and 102, respectively, move the stage to the registration position. Motor 330 is enabled to drive the macro-micro transport arm 244 to the micro inspection station. Next, the autofocus is again enabled and the objective lens is brought into a position of focus as described hereinabove. The image is then grabbed and transmitted to the image processor which compares it with that of the unique position selected prior to handoff from the macro inspection station. Stage movement in X, Y and theta is employed to obtain registration with the prestored pattern within two microns. Once this is accomplished, the moveable turret support 544 is again raised the detent is removed from the associated V-slot and the turret 608 is driven to bring the next higher magnification lens (20X) into the micro optical axis. Automatic focus is again effected, and it is to be noted that a slight realignment will be required each time the objective lens is changed because the apparent center of the field of view in one lens is not the same as that in another lens. The stage is moved to adjust for this difference, and this can be placed in memory so that such correction is automatically performed as the objective is being selected. The autofocus again focuses on the image at the new magnification and the image is grabbed for comparison in the image processor with the prestored registration pattern.

This procedure gives a reasonably good alignment but it is known that the patterns layed out on the wafer are not precisely aligned with the flat. To correct for any misalignment in the forming of the patterned wafer, the following procedure is employed. The stage controls are effectuated to move the stage so that it is approximately five milimeters from the leftmost edge and is centered. An image is then grabbed and transmitted to the image processor. Next, the stage is moved so that it is five milimeters from the rightmost edge and centered and the image is grabbed. The second image is transmitted to the image processor where it is compared with the prestored pattern. Based upon any misalignment which would be determined by the comparison, the stage is rotated in theta by control signal from movement controller 52 to motor controller 52D4 and motor 262 which rotates the turntable 94. This process is repeated using the next higher magnification objective lens (50X) so as to obtain precise positioning of the wafer in the micro optical axis prior to performing the micro inspection. This inspection areas and the tests to be performed are selected by the user. These include micro measurements such as critical dimension, micro area and registration; and micro comparison which includes sample inspection repeating defects inspection and random defects inspection. The tests will be done at preselected sites on the wafer and with the use of predetermined objective lens magnifications. In the registration measurement, i.e., the misalignment between patterns which are formed on the wafer, a colored filter is inserted in the illumination system during one of the tests. A drive motor such as 434 (FIG. 20) and an overall drive assembly such as shown in 432 in the figure is employed to position the filer in the illumination system for the micro optics.

Following inspection, the wafer is to be removed from the vacuum chuck 92 on the stage 28, and this is accomplished as follows. The autofocus controls first are effected to move the moveable turret 544 to its uppermost position and to move the lowest magnification lens into the viewing position. This gives the maximum clearance between the top surface of the wafer and the lowest part of the objective lens. Because the wafer is to be raised by the wafer unloaded transfer arm, the next step is to move the stage away from the micro optical axis and to accomplish this the stage controls are effected causing the motors 100 and 102 to drive the stage toward the wafer track. As this movement takes place, the movement controller 52 also sends control signals to wafer unload controls 52G. Motor controller 52G1 enables motor 98 which causes the wafer unload transfer arm 98 to move into position adjacent vacuum chuck 92 and below with the wafer under test. Once in position, an air piston, such as shown in FIGS. 9 and 10 for the wafer transfer arm 90, is turned on and the transfer arm 98 moves vertically upward. At this same time, a vacuum is drawn via vacuum line 236 to the vacuum holes 234 in the arcuate portion 235 of wafer unload transfer arm 98. A control signal to stage controller 52D disables the vacuum on chuck 92 allowing the wafer to be picked up vertically by the unload transfer arm 98. Drive motor 98A is enabled which then pivots the transfer arm about pivot 99 to position the arcuate portion beyond the unload pad 76. Once this position is acknowledged, an actuator assembly, such as 124 shown in FIG. 8A, is enabled driving the unload pad up under the wafer, approximately at the center. At this time, the vacuum on arm 98A is disabled and a vacuum is drawn in the aperture 75 of load pad 76 to hold the wafer thereon. The wafer is then on unload pad 76 and slightly above the arcuate portion 235 of arm 98. Once these missions are accomplished the motor 98A again is enabled to move the wafer arm out of the path and once this mission is accomplished the actuator such as 124 is again enabled but this time to drive the load pad 76 downward to its lowermost position. While the wafer is being moved to the unload position, a determination is made as to whether the wafer has failed or passed the inspection. This information is used to determine the direction of motion of the motor 84. Once the wafer has been placed in the unload track, it will be driven either to the pass or fail cassette as explained hereinabove.

High Speed Image Processing System

The high speed image processing system 56 is the heart of the electronics in this inspection system. A generalized block diagram of the high speed image processing system is illustrated in FIG. 40, and it should be noted that this image processing system can be considered to be made up of a plurality of functional modules. As should clear from the preceding discussion, the overall inspection system is critically dependent upon clear, accurate video images. For this reason, it is important that camera 38 be of high quality. Also, because the system must be capable of doing comparisons of an image against a previously stored image, which may have come from either another inspection system such as the one described herein or from a stored data base, the images must be linear to a tolerance that is higher than the tolerance currently available commercial cameras. Further, the image dimensions must be repeatable to tighter tolerances than the optics allow. Finally, the system must take into account the inherit shading variations in the camera output. A camera correction circuit 56A effects the linearity and tolerance requirements by first reading a test image from a wafer into image memory 56C when there are no corrections applied. This image is then divided into a number of sub images in a correlation process, which measures the X and Y displacements for each sub image. The displacements for each sub image are stored in a memory array. The correction system 56A will subsequently access these stored displacement as the camera scans an image, and effects an interploation, on the fly, to generate analog X and Y correction voltages for the camera sweep generators. In order to accomplish this result, the camera is equipped with yokes and associated circuity to implement the X and Y corrections. The shading correction is implemented in a similar manner. The optical control is implemented to provide alternate dark and bright field images and the camera grabs dark and bright flat field images which are transmitted to the image memory 56C. The correlation processor again processes these as an array of sub images to determine offset and gain correction factors for each sub image. These correction factors are stored and are again accessed during camera scan and interploated on the fly to generate gain and offset adjust signals to the video input circuitry.

The video input controls the analog to digital (A/D) conversion of camera video and the writing of the resultant pixel values into image memory. It has a viewport, window, and inverses zoom capabilities. A 20 megahertz FIFO buffer is included from interface to the video data bus 55A.

The overall structure of the image processing system employes a dual bus architecture. A low speed bus 55B is a 32-bit data, 24-bit address bus and is used to initiate all data transfers within the image processing system. All transactions utilize this bus for addressing, but depending on the type of transaction, data is transferred either on the low-speed bus 55B, or on the high-speed (video data bus) 55A. The low-speed bus 55B is a five megahertz synchronized bus capable of starting a new transaction every 200 nanoseconds. The video data bus is used to transfer video data to and from image memory at 20 megahertz, in packets of between 1 and 16 pixels for each data request on the low-speed bus. The various functions which generate or receive video data are connected to this bus via FIFO memory buffers enabling time sharing of the bus by multiple sub systems. Since most video data is processed at approximately 10 megahertz, this FIFO interface increases effective bus band with by a factor of 2. The FIFO's also enable data to be sent in packets at high speed decoupling the data transfer from the variable rate at which the data may be processed, depending on the particular algorithm and hardward being used. As will be disclosed hereinafter, should a particular FIFO become full, signals are sent back to prevent further data from being sent until the present data has been processed. A VERSABUS (68000 bus) interface permits the system controller 50A to access image memory and image process control registers. It also permits transfer of image data to and from the system disk. The general operation of the image processing system is that the images are loaded into image memory 56C either from the camera and video input 56B or from disk memory. Images in memory are then accessed by the processor and the results written back into image memory. The memory controller 56F is designed so that it may access any part of a memory for image display.

Image Memory

In a preferred embodiment of the invention, the image memory is contained on two boards, each of which holds four images, i.e., one megabyte. Normal low speed bus accesses are 8 bits (one pixel) wide. To increase image transfer rates to and from a disk, a second memory configuration is provided which allows 32 bit access on the low-speed bus. A memory read cycle for video rata data (for display or processing) is achieved by inserting an address and function code on a low-speed bus 55B. The function code specifies that a video data read is to be executed. In this case, the memory address specifies a group of 16 consecutive pixels in the X direction, and all 16 of these are simultaneously accessed and latched into holding registers on a memory board. These 16 pixels are then multiplexed at high speed (20 megahurts) onto the video databus which is part of the high speed bus 55A. By this organization, standard high density low-speed dynamic RAM's may be used for the image memory.

Video data input to the memory is handled in a corresponding fashion. Pixel data at 20 megahertz is latched into holding registers on the memory board then transferred 16 pixels at a time into the memory array.

Memory Controller

The memory controller permits accessing of image memory for display on the video monitor 54. It allows programming of the video's sychronization characteristics, display viewpoint, window and zoom and includes a programmable hardware cursor. A 20 megahertz FIFO buffer is provided so as to be compatible with the video data bus transmission rate.

High-Speed Address Generator

An overall block diagram of the high-speed address generator 56E is shown in FIG. 41 and the separate denstination and source address generators are shown in more detail in FIG. 42. As may be seen from the figures, a command sequencer which includes FIFO 702, start address 704, microcode sequencer 706, microcode memory 708, pipeline 710 and 2:1 multiplexer 712 is used to provide the commands by which the address generator 56C is driven. These commands includes direct load commands, which allow direct initialization of the address generator buffers registers, a start address command, which loads a vector jump address for the microcode sequencer. This then initializes the address generator buffer registers using pre-stored microcode sequences and interrupt commands, which allow the address generator to interrupt the system controller 50A upon completion of a specified task. Using FIFO's for command sequences allows the high-speed processor to be programmed for a chain of future commands comprising source and destination addresses while it continues to execute the current command. This decoupling allows the 68000 to operate independently of the high-speed processor and allows the high-speed processor to go after the next programmed test without having to wait for this to be sent from the system controller.

The address generator provides addresses for each of three image areas within memory. Two of these can be considered source images, i.e., processor inputs, and the third a destination image, i.e., processor output. The source and destination address generator 718 are shown separately as source address generator 720 and destination address generator 722 in FIG. 42. These two different address generators are functionally independent entities as may be seen from the figure.

The source address generator 720 generates what can be considered a base address sequence for the two source images. The address generator consists of X and Y up/down counters which count between predefined X and Y start and end points. These X-Y counters enable rectangular areas of image to be accessed. These X start and end points can be selectively modified by the output of a vector generator 720, which is initialized by loading delta X and delta Y to define the slope of a vector. By so doing, the configuration of the area accessed is modified from the standard rectangular pattern to trapazoidal or triangular patterns, or to address sequences generated along vectors or around circles so as to permit processing along contours rather than over areas. The vector circle generator is a hardware implementation of an algorithim described by P. E. Danielsson, Ihhh Transactions on Computers, Vol. C-19, No. 9, September, 1970. In addition to the configuration developed for the algorithm, a filter function has been added to the basic structure to improve the quality of the circles and the accuracy of on-axis vectors.

The address sequence for each source image is then generated by feeding the base address sequence to an address modifier such as shown at 724 or 726. The address modifier allows the base address to be offset in X and Y on a segment by segment or overall image basis. It also has the ability to automatically step a multiple segment address sequence over a rectangular area for generation of correlation surfaces. To implement convolution, the address sequence can be reversed by either address modifier. The output of each address modifier is fed to a FIFO interface 728 or 730, respectively, which controls accessing of image memory, and cycles pixel data from memory at 20 megahertz into a data FIFO 732 which is accessed by the processor at 10 megahertz. The FIFO memorys are implemented using standard 10 megahertz FIFO chips by connecting them in pairs which are "ping-ponged" to achieved the desired 20 megahertz data rate.

Referring again to FIG. 42, it may be seen that that destination address generator is a simplified version of the source address generator in that it is a single channel and can address only rectangular areas. In addition to the addressing capability, it has the ability to expand defects in the X-axis and to pack single-bit defect data into bytes. The processor output data is loaded into image memory by means of a 20 megahertz FIFO interface that is similar to the one described for the source address generator.

To generate the address sequence for convolution, the basic address generator outputs are subtracted from rather than added to, the programmed offsets. This has the effect of reversing the address sequence.

To implement blur, the basic address sequence can be shifted right by one bit. This effectively halves the frequency of address changes for the output of a blur.

Correlation Processor

Referring now to FIG. 43, it may be seen that the pixel data which is loaded into the data FIFO interface 732 and 734 is transmitted via paths 736 and 738 to input control logic 740 of the correlation processor. The correlation processor unloads data from the data FIFO interfaces and feeds it via input control logic 740 and paths 742 and 744 to a multiplier accumulator network 746. In a preferred embodiment of the invention, the multiply-accumulator network 746 includes three accumulators and two multipliers which can be configured in a variety of ways depending upon the task to be performed on the incoming data.

The output of this multiply/accumulator network 746 is passed to a 32-bit bipolar bit-slice processor 750 via path 749. The bits-slice processor executes directly from microcode at 10 megahertz. The micro code, which is 64-bits wide, is held in a high-speed static RAM 752 and is loaded by the 68000 system controller 50. The bit-slice processor is microcoded to implement the various algorithms handled by this processor. More importantly, it implements the multiply and divide functions required at the end of each pass of a correlation algorithm. In this situation, the bit-slice processor 750 operates independently of the multiply/accumulate network, allowing execution of the time consuming multiply and divide operations to overlap accumulation of pixels for the next pass of the algorithm. The bit-slice processor 750 is augmented by a 1K×16 scratch-pad RAM for temporary storage. This RAM can also be loaded directly from the pixel data in the input data stream. When processing is complete, the output data from the bit-slice processor 750 is multiplexed via output multiplexer 754 to an 8-bit data bus and sent to the destination address generator to be written into image memory.

Defect Processor

Referring now to FIG. 44, the manner in which the defects are detected may be understood. The defect algorithm processor is a high-speed dedicated pipeline processor which implements the defect detection algorithm. Most of the operations involve processing of 3×3 areas of images. The pixel images enter line buffer 762 via path 760, and the line buffer is a to 2-line delay which allows parallel access to the current pixel and the corresponding pixels from the previous two lines. Because the line length is variable, the line buffer is implemented with a RAM and counters forming what is in essence a variable length shift register. The maximum line length is 512 bits. The line buffer 762 is used to produce one column of data three rows high. The data rate at the output is 10 megahertz.

The overall structure of the defect processor dictates that similar processing be carried out between the two input images in both directions. To minimize the hardware required, the input image pixels are read alternately from the two images and the same hardware is used to implement the algorithm in both directions. Such an arrangement does in fact lower the throughput, and should increased speed be desired, separate circuits could be used for each direction.

The three row data output from the line buffer 762 is applied to Sobel generation circuit 764 where it is operated by X and Y Sobel operators to generate Sobel X and Y functions of the source image. These functions are than passed through look-up tables to generate resultant Sobel magnitude and direction. Pixel magnitude circuity encompasses all of those parameter computations and matrix comparisons. Data routed to the So Bel generator is combined with adjacent pixel data to obtain a gradient vector with cartesian coordinates. This resultant will be transformed into a gradient magnitude and phase and is in polar coordinants. At this point, further delays are placed upon the pixel address and data, sychronizing the line buffers and line delays. The gradient information is separated into two parts—phase and magnitude. The phase data is delayed. The magnitude data is used to derive a mean value. The gradient means value is first delayed to sychronize the data for later possible use by the phase range scaler circuit 772. Then the data is converted to column format via a line buffer 770 for input to a 3×3 generator 774. In the 3×3 generator 774, the image values are extracted and transferred to generate tolerance values for the gradient mean comparator 778 and the phase range comparator 780. Resultant information from the gradient mean comparator 778 is on a 1:1 correspondence for matching between of adjacent pixels of the 3×3 matrix. This output is used by the pixel comparator 782.

Phase data is both delayed for the 3×3 generator (phase) 768 and is used by the phase range comparator 784. Phase data after being converted into a column format in the phase line buffer 786 is routed to the front end of the phase range generator 784. After one delay, column information is routed to a delay circuit 788, compensating for computational time needed in generation of the phase range. Column information is also used by the phase range generator to generate a phase range resultant which is adjusted by the phase range scaler circuit 790 and used as a tolerance in the reference from the candidate pixel and phase comparator 780. This tolerance is determined by the maximum tolerance selection either being a scaled phase range value or a scaled gradient mean value, whichever is greater. Output from the column delay of the phase data is also sent to a 3×3 generator 792 after a delay circuit. This 3×3 generator is used to create a 3×3 matrix of phase data for simultaneous sampling by the phase comparator 780. The 3×3 generator 792 also extracts the candidate pixel value which is used as a reference in the phase range scaler 772.

The pixel comparator 782 receives data from the gradient comparator 778 and phase comparator 780, and the result from the pixel magnitude comparator 794. The received data is applied to an AND circuit to determine a defect condition. A defect will occur if an inconsistency is detected for both comparisons, i.e., one with image 1 as a candidate and one with image 2 as a candidate.

While this invention has been described in the light of a preferred embodiment thereof, it is contemplated that modifications will become apparent to those skilled in the art after having read the preceeding description of the preferred embodiment. It is therefore intended that the following appended claims be interpreted as covering all such modifications as fall within the true spirit and scope of this invention.

What is claimed is:

1. A system for automatic micro and macro inspection of patterned wafers, comprising:
    X-Y stage means for supporting wafer at a macro inspection station and a micro inspection station;
    means for storing a plurality of patterned wafers before and after inspection;
    means for transferring a wafer from said storing means to a predetermined location on said X-Y stage means;
    means for centering said wafer in said macro inspection station;
    means for aligning said wafer to obtain a preselected orientation for macro inspection;
    means for effecting macro inspection of said wafer;
    means for grabbing a unique image following macro inspection and storing said unique image;
    means for moving said wafer to said micro inspection station so that the area of said wafer correspondence to said stored unique image is in a micro optical path;
    means for automatically focusing the lowest magnification objective lens on said area of said wafer to derive a real time image;
    means for comparing said stored unique image to said real time image;
    means responsive to the comparison of said stored unique image and said real time image and operative to more precisely position said wafer in said micro optical path;
    means for using areas of said wafer, displaced one from the other, to obtain a more precise alignment;
    means for performing a preestablished micro inspection on selected areas of said wafer; and
    means for transporting said wafer to said storage means.

2. A system as set forth in claim 1 wherein said means for centering comprises:
    means for illuminating said wafer;
    means for processing the reflected light which is adjacent the periphery of the wafer to obtain a summation of the pixels around the circumference; and
    means moving said wafer on said stage to a portion wherein a minimum sum is obtained, whereby said wafer will be centered.

3. A system set forth in claim 2 wherein said means for aligning comprises:
    means for aligning the wafer flat in accordance with the users selected orientation;
    means for moving the stage to a reference area of such as a dropout in the wafer pattern;
    means for comparing the dropout image with a reference; and
    means for moving the stage means so as to align the dropout image with said reference.

4. A system as set forth in claim 3 wherein said means for effecting a macro inspection comprises:
    moving the stage to a center position in each of four quandrants;
    means for selecting a pair of images at each quadrant;
    means for comparing the selected images to determine if they are alike or different; and
    means for determining if the differences, if any, are within or without tolerance for the wafer inspection.

5. A system as set forth in claim 4 wherein said means for grabbing a unique image comprises:
    means for moving the wafer so that the unique image is centered in the field of view;
    means for moving the highest magnification macro lens into the macro optical path; and
    means for storing said unqiue image.

6. A system as set forth in claim 5 wherein said means for moving to said micro inspection station comprises:

an objective lens turret including a plurality of different magnification objective lenses on said turret;
means for moving said turret up and down vertically;
control means for ensuring said turret is in its uppermost position; and
means for transporting said wafer from the macro inspection station to the micro inspection station.

7. Apparatus as set forth in claim 6 wherein said means for automatically focusing comprises:
    means for rotating said turret to bring the lowest magnification objective lens into said micro optical path;
    means for illuminating said micro optical path with a reticle pattern;
    means responsive to said reticle pattern characteristics for focusing said objective lens; and
    means for comparing the stored image with the real time image from the wafer aligned with said stored image.

8. Apparatus as set forth in claim 7 wherein said means for using areas of said wafer comprises:
    means for moving said stage to a position near the right edge of said wafer;
    means for grabbing an image at said right edge;
    means for storing said right edge image;
    means for moving said stage to a position near the left edge of said wafer;
    means for grabbing an image at said left edge;
    means for comparing said right and left images; and
    means for moving said stage to bring said right and left images into alignment.

* * * * *